(12) United States Patent
Nakamura et al.

(10) Patent No.: US 9,643,952 B2
(45) Date of Patent: May 9, 2017

(54) PYRIDONE COMPOUND

(71) Applicant: KYOWA HAKKO KIRIN CO., LTD., Tokyo (JP)

(72) Inventors: Rina Nakamura, Tokyo (JP); Seiji Aratake, Tokyo (JP); Kenji Uchida, Tokyo (JP); Kimihisa Ueno, Tokyo (JP); Maasa Motosawa, Tokyo (JP); Takahiro Kabeya, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 14/650,152

(22) PCT Filed: Dec. 6, 2013

(86) PCT No.: PCT/JP2013/082763
§ 371 (c)(1),
(2) Date: Jun. 5, 2015

(87) PCT Pub. No.: WO2014/088085
PCT Pub. Date: Jun. 12, 2014

(65) Prior Publication Data
US 2015/0315172 A1 Nov. 5, 2015

(30) Foreign Application Priority Data
Dec. 6, 2012 (JP) ................. 2012-267008

(51) Int. Cl.
| | |
|---|---|
| C07D 401/06 | (2006.01) |
| C07D 213/74 | (2006.01) |
| C07D 405/14 | (2006.01) |
| C07D 413/14 | (2006.01) |
| C07D 401/14 | (2006.01) |
| C07D 417/14 | (2006.01) |
| A61K 31/4545 | (2006.01) |
| C07D 213/82 | (2006.01) |
| C07D 401/12 | (2006.01) |
| C07D 409/14 | (2006.01) |
| C07D 491/107 | (2006.01) |

(52) U.S. Cl.
CPC ........ *C07D 401/06* (2013.01); *A61K 31/4545* (2013.01); *C07D 213/74* (2013.01); *C07D 213/82* (2013.01); *C07D 401/12* (2013.01); *C07D 401/14* (2013.01); *C07D 405/14* (2013.01); *C07D 409/14* (2013.01); *C07D 413/14* (2013.01); *C07D 417/14* (2013.01); *C07D 491/107* (2013.01)

(58) Field of Classification Search
CPC .. C07D 213/14; C07D 401/06; C07D 401/14; C07D 405/14; C07D 409/14; C07D 413/14; C07D 417/14; C07D 491/107
USPC .......... 514/210.18, 237.2, 253.12, 278, 318; 544/130, 365; 546/17, 194
See application file for complete search history.

(56) References Cited

U.S. PATENT DOCUMENTS

| | | | |
|---|---|---|---|
| 6,949,571 | B2 | 9/2005 | Nagato et al. |
| 7,115,608 | B2 | 10/2006 | Guillemont et al. |
| 7,563,811 | B2 | 7/2009 | Nagato et al. |

(Continued)

FOREIGN PATENT DOCUMENTS

| | | | |
|---|---|---|---|
| CN | 1439003 A | | 8/2003 |
| CN | 1744899 A | | 3/2006 |

(Continued)

OTHER PUBLICATIONS

Improper Markush, Fed. Reg. 76(27) p. 7162-7175, slide 1, 64-67 (2011).*
Kalindjian et al. "A new series of . . . " J. Med. Chen. 59, 3038-3111(2016).*
Silverman e "The organic chem . . . " p. 65-73 (1993).*
Chen et al., *International Immunology*, 18(8): 1233-1242 (2006).
Duhen et al., *Nature Immunology*, 10(8): 857-863 (2009).
Hijnen et al., *Journal of Allergy and Clinical Immunology*, 113(2): 334-340 (2004).
Hijnen et al., *Journal of Investigative Dermatology*, 125: 1149-1155 (2005).
Homey et al., *Journal of Allergy and Clinical Immunology*, 118(1): 178-189 (2006).
Homey et al., *Clinics in Dermatology*, 26: 539-545 (2008).
Homey et al., *Nature Medicine*, 8(2): 157-165 (2002).
Kagami et al., *European Journal of Immunology*, 38: 647-657 (2008).

(Continued)

*Primary Examiner* — Celia Chang
(74) *Attorney, Agent, or Firm* — Leydig, Voit & Mayer, Ltd.

(57) ABSTRACT

The invention provides a pyridone compound represented by the following formula (I) [wherein, $R^1$ represents cycloalkyl optionally having substituent(s) and the like, $R^2$ represents a hydrogen atom and the like, $R^3$ represents hydroxy and the like, and $R^{4A}$ represents the following formula ($R^{4A}$-1) (wherein, $R^4$ and $R^5$ are the same or different and each represents a hydrogen atom and the like), and the like], or a pharmaceutically acceptable salt thereof, which is useful as a prophylactic and/or therapeutic agent for skin diseases, and the like.

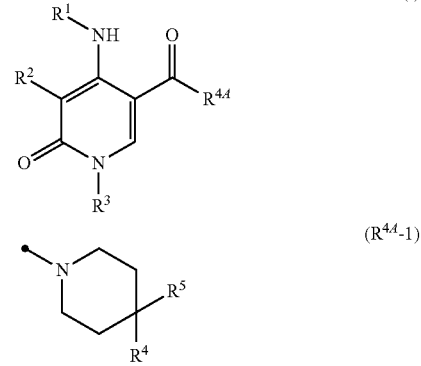

15 Claims, No Drawings

(56) References Cited

U.S. PATENT DOCUMENTS

| | | | |
|---|---|---|---|
| 7,645,771 B2 | 1/2010 | Kazmierski et al. | |
| 7,759,367 B2 | 7/2010 | Smith | |
| 7,915,250 B2* | 3/2011 | Aay | C07D 205/04 514/210.18 |
| 7,939,549 B2 | 5/2011 | Nagato et al. | |
| 8,399,493 B2 | 3/2013 | Bolea et al. | |
| 2003/0187020 A1 | 10/2003 | Astles et al. | |
| 2004/0023973 A1 | 2/2004 | Nagato et al. | |
| 2004/0082619 A1 | 4/2004 | Tada et al. | |
| 2004/0229847 A1 | 11/2004 | Guillemont et al. | |
| 2005/0101590 A1 | 5/2005 | Yasui et al. | |
| 2005/0130943 A1 | 6/2005 | Wallace et al. | |
| 2005/0130976 A1 | 6/2005 | Wallace et al. | |
| 2005/0153942 A1 | 7/2005 | Wallace et al. | |
| 2005/0245581 A1 | 11/2005 | Nagato et al. | |
| 2005/0250782 A1 | 11/2005 | Marlow et al. | |
| 2005/0256123 A1 | 11/2005 | Marlow et al. | |
| 2006/0052411 A1 | 3/2006 | Tada et al. | |
| 2006/0100249 A1 | 5/2006 | Smith | |
| 2006/0229336 A1 | 10/2006 | Kazmierski et al. | |
| 2006/0270709 A1 | 11/2006 | Gray et al. | |
| 2006/0276510 A1 | 12/2006 | Abu-Shakra et al. | |
| 2007/0112038 A1 | 5/2007 | Marlow et al. | |
| 2007/0213323 A1 | 9/2007 | Imogai et al. | |
| 2007/0293544 A1 | 12/2007 | Abel et al. | |
| 2008/0081825 A1 | 4/2008 | Nakai et al. | |
| 2008/0280957 A1 | 11/2008 | Marlow et al. | |
| 2008/0312292 A1 | 12/2008 | Yasui et al. | |
| 2009/0030017 A1 | 1/2009 | Hanada et al. | |
| 2009/0131435 A1 | 5/2009 | Marlow et al. | |
| 2009/0131480 A1 | 5/2009 | Gray et al. | |
| 2009/0143389 A1 | 6/2009 | Blake et al. | |
| 2009/0143579 A1 | 6/2009 | Blake et al. | |
| 2009/0156576 A1 | 6/2009 | Aay et al. | |
| 2009/0209542 A1 | 8/2009 | Marlow et al. | |
| 2009/0215834 A1 | 8/2009 | Marlow et al. | |
| 2009/0275751 A1 | 11/2009 | Nagato et al. | |
| 2010/0063053 A1 | 3/2010 | Marlow et al. | |
| 2010/0081686 A1 | 4/2010 | Tada et al. | |
| 2010/0249096 A1 | 9/2010 | Aay et al. | |
| 2011/0039851 A1 | 2/2011 | Dey et al. | |
| 2011/0178136 A1 | 7/2011 | Marlow et al. | |
| 2011/0183981 A1 | 7/2011 | Marlow et al. | |
| 2011/0263558 A1 | 10/2011 | Aay et al. | |
| 2011/0288092 A1 | 11/2011 | Marlow et al. | |
| 2012/0263679 A1 | 10/2012 | Marlow et al. | |
| 2013/0018075 A1 | 1/2013 | Marlow et al. | |
| 2013/0109652 A1 | 5/2013 | Imogai et al. | |
| 2014/0221340 A1 | 8/2014 | Yamamoto et al. | |
| 2014/0275527 A1 | 9/2014 | Aay et al. | |
| 2015/0141399 A1 | 5/2015 | Aay et al. | |
| 2015/0299214 A1* | 10/2015 | Uchida | C07D 401/14 514/210.2 |

FOREIGN PATENT DOCUMENTS

| | | |
|---|---|---|
| CN | 101365676 A | 2/2009 |
| EP | 1741702 A1 | 1/2007 |
| EP | 2927214 A1 | 10/2015 |
| JP | 2008-520615 A | 6/2006 |
| JP | 2009-511490 A | 3/2009 |
| JP | 2011-500698 A | 1/2011 |
| WO | WO 01/96308 A1 | 12/2001 |
| WO | WO 02/24650 A2 | 3/2002 |
| WO | WO 02/053543 A1 | 7/2002 |
| WO | WO 03/047577 A2 | 6/2003 |
| WO | WO 2003/070277 A1 | 8/2003 |
| WO | WO 2004/054974 A2 | 7/2004 |
| WO | WO 2005/051301 A2 | 6/2005 |
| WO | WO 2005/105743 A1 | 11/2005 |
| WO | WO 2006/030032 A1 | 3/2006 |
| WO | WO 2006/056427 A1 | 6/2006 |
| WO | WO 2006/107860 A1 | 10/2006 |
| WO | WO 2006/109876 A1 | 10/2006 |
| WO | 2007/044515 * | 4/2007 |
| WO | WO 2013/031931 A1 | 3/2013 |

OTHER PUBLICATIONS

Mirshahpanah et al., *Experimental Dermatology*, 17: 30-34 (2007).
Trifari et al., *Nature Immunology*, 10(8): 864-871 (2009).
Japanese Patent Office, International Search Report in International Patent Application No. PCT/JP2013/082763 (Jan. 7, 2014).
European Patent Office, Supplementary European Search Report in European Patent Application No. 13860161 (Apr. 25, 2016).
Liu et al., *Foreign Medical Science (Section of Dermatology and Venereology)*, 28(3): 166-169 (2002).
Liu et al., *Journal of Practical Dermatology*, 3(1): 24-27 (2010).
Qian et al., *Chinese Journal of Dermatology*, 38(6): 351-353 (2005).
Chinese Patent Office, Notification of First Office Action in Chinese Patent Application No. 201380069373.8 (May 31, 2016).

* cited by examiner

PYRIDONE COMPOUND

CROSS-REFERENCE TO RELATED APPLICATIONS

This patent application is the U.S. national phase of International Patent Application No. PCT/JP2013/082763, filed Dec. 6, 2013, which claims the benefit of Japanese Patent Application No. 2012-267008, filed on Dec. 6, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 926 bytes ASCII (Text) file named "720991SequenceListing.txt," created Jun. 3, 2015.

TECHNICAL FIELD

The present invention relates to a pyridone compound or a pharmaceutically acceptable salt thereof useful as an agent for the prophylaxis and/or treatment of skin diseases, and the like.

BACKGROUND ART

Chemokine is a series of families of small inflammatory cytokines having a strong chemotactic activity and being composed of about 70-120 amino acids, and is a chemotactic cytokine released from a wide variety of cells in order to lead various cells such as monocyte, macrophage, T cell, eosinophil, basophil, neutrophil and the like to the inflammatory site. The chemokine family was originally defined by 4 conserved cysteine residues in an amino acid sequence, namely, classified into two subfamilies of CXC-chemokine family and CC-chemokine family based on the configuration of the first cysteine pair (two residues) on the N terminal side. In the CXC-chemokine family including CXCL1, Mig, CX3CL1, IL-8, Gro-α, NAP-2, IP-10 and the like, these two cysteine residues are separated by one of the amino acid residues other than cysteine; on the other hand, in the CC-chemokine family including RANTES(CCL5), MCP-1 (CCL2), MCP-2(CCL8), MCP-3(CCL7), MCP-4(CCL13), MIP-1α(CCL3), MIP-1β(CCL4), Eotaxin(CCL11), Eotaxin-2(CCL24), Eotaxin-3(CCL26), PARC(CCL18), TARC(CCL17), MDC(CCL22), LARC(CCL20), ELC (CCL19), SLC(CCL21), I-309(CCL1), TECK(CCL25), CTACK(CCL27), MEC(CCL28) and the like, these two cysteine residues are contiguous. Thereafter, the C chemokine family having, of the four cysteine residues originally present, only two cysteine residues corresponding to the second and the fourth residues from the N terminal side, and the CX3C chemokine family having a sequence having three amino acid residues different from cysteine between the first two cysteine residues on the N terminal side were found.

Ten kinds of receptors have been reported as the chemokine receptor that CC-chemokine family binds to. That is, CCR1 (alias, CKR1 or CC-CKR-1) bindable with MIP-1α, MIP-1β, MCP-3, RANTES and the like, CCR2A (alias, CKR2A or CC-CKR-2A) and CCR2B (alias, CKR2B or CC-CKR-2B) bindable with MCP-1, MCP-2, MCP-3, MCP-4 and the like, CCR3 (alias, CKR-3 or CC-CKR-3) bindable with Eotaxin, Eotaxin-2, RANTES, MCP-2, MCP-3 and the like, CCR4 (alias, CKR4 or CC-CKR-4) bindable with TARC, MDC and the like, CCR5 (alias, CKR-5 or CC-CKR-5) bindable with MIP-1α, RANTES, MIP-1β and the like, CCR6 (alias, GPRCY4) bindable with LARC and the like, CCR7 (alias, EBI-1) bindable with ELC, SLC and the like, CCR8 bindable with I-309 and the like, CCR9 (alias, GPR9-6) bindable with TECK and the like, and CCR10 bindable with CTACK, MEC and the like are known [Nature Reviews Immunology, 2002, vol. 2, page 106].

Chemokine receptors have different expression cells depending on the kind of the receptor. For example, CCR1 is expressed in various cells such as monocyte, T cell, mast cell, eosinophil, basophil and the like, and CCR2 is expressed in various cells such as dendritic cell, B cell, basophil, eosinophil, vascular endothelial cell, fibroblast, platelet, T cell and the like. On the other hand, some receptors are expressed only in some cells such as CCR3 expressed in eosinophils and basophil, and CCR9 expressed in T cells.

Since involvement of chemokine receptor in various diseases has been reported, a medicament modulating a chemokine receptor activity is expected to be a therapeutic drug for various diseases [Expert Opinion on Investigational Drugs, 2010, vol. 19, page 345]. Heretofore, plural chemokine receptor activity modulators have been used as therapeutic drugs. For example, it has been clarified that, when CD4+T cells are infected with HIV, HIV invades into the cells via CCR5, and therefore, CCR5 antagonist is used as a therapeutic drug for HIV infection. Also, as a medicament for mobilization of stem cells in autologous stem cell transplantation in patients with non-Hodgkin lymphoma and multiple myeloma, a combined use of an antagonist of CXCR4 which is a receptor of CXC-chemokine family with G-CSF has been approved. Besides these, CCR3 antagonist, CCR9 antagonist, antibody to CCR4 and the like are under clinical tests [Expert Opinion on Investigational Drugs, 2010, vol. 19, page 345].

As diseases involving a chemokine receptor, inflammatory diseases such as asthma, rhinitis, dermatitis, allergic disease and the like, immunoregulatory disorders and diseases, autoimmune diseases such as rheumatoid arthritis, lupus erythematosus, generalized scleroderma, Sjogren's syndrome, Celiac disease and the like, and the like are known [Current Opinion in Immunology, 2001, vol. 13, page 670]. Involvement of chemokine receptors such as CCR1; CCR2A; CCR2B; CCR3; CCR4; CCR5; CCR6; CCR7; CCR8; CCR9; CCR10; CXCR3 and CXCR4 which are receptors of CXC-chemokine family; and the like in the onset of these diseases has been reported. Among these, as a disease involving CCR4, CCR8, CCR9, CCR10 and the like, skin diseases and the like are known [Journal of Investigative Dermatology, 2009, vol. 129, page 2552].

As skin diseases involving a chemokine receptor, acne vulgaris, drug eruption, contact dermatitis, pollen dermatitis, urticaria, psoriasis, atopic dermatitis, Candida dermatitis, seborrheic dermatitis, eczema, Stevens-Johnson syndrome, toxic epidermal necrosis, erythema multiforme, pityriasis rosea, lichen planus, lichen pilaris (keratosis pilaris), herpes simplex, lupus erythematosus, keloid, scabies, generalized scleroderma and dermatitis as a side effect of anti-cancer agents and the like are known. In these skin diseases, various chemokines are highly expressed in the skin. For example, it is known that, in psoriasis, expression of chemokines such as MCP-1, RANTES, TARC, MDC, CTACK, CXCL1, Gro-α, IL-8, Mig, IP-10, CX3CL1 and the like increases in the dermatitis site and T cells and neutrophils infiltrate into the skin via CCR4; CCR6; CCR10; and CXCR1, CXCR2 and CXCR3, which are receptors of CXC chemokine family; and the like (non-patent document 1), in atopic dermatitis, expression of chemokine such as 1-309, MCP-1, MIP-1α, MIP-1β, RANTES, Eotaxin, MCP-4, PARC, LARC, MDC, Eotaxin-3, CTACK and the like increases in the dermatitis site and T cells, monocyte, eosinophils infiltrate into the skin via CCR1; CCR2A; CCR2B; CCR3; CCR4; CCR5; CCR6; CCR8; CCR10; CX3CR1 which is the receptor of CX3C chemokine family; and the like (non-patent document 2) and the like. Also, it has been reported that anti-CTACK antibody suppresses dermatitis in various dermatitis models and the like (for example, non-patent documents 3, 4, 5, 6 and the like). As a medicament that modulates chemokine receptor activity in skin diseases and the like in which these chemokine receptors are involved, pyrazolopyrimidine derivatives are known (patent document 12).

CCR10 is a chemokine receptor belonging to the C-C chemokine family [Genomics, 1994, vol. 23, page 609], and mainly expressed in the cells localized in the skin such as Cutaneous lymphocyte-associated antigen (CLA) positive skin-homing T cells, skin vascular endothelial cell, skin fibroblast, skin keratinocyte and the like. As a chemokine whose receptor is CCR10, two kinds of Cutaneous T-cell attracting chemokine (CTACK: alias CCL27) and Mucosae-associated epithelial chemokine (MEC: alias CCL28) are known. CCR10 and ligand thereof are said to be involved in the immunity of epithelial cells [Protein & Cell, 2012, vol. 3, page 571].

In recent years, involvement of CCR10 in atopic dermatitis has been reported. CTACK is selectively expressed in skin keratinocytes, and skin-homing CCR10 positive cells selectively migrate into CTACK. In patients with atopic dermatitis, expression of CTACK in the lesion skin is promoted, and in atopic dermatitis patients, the blood level of CTACK shows a positive correlation with the severity of dermatitis (non-patent document 7). Also, in the lesion skin of atopic dermatitis patients, localization of CCR10 positive T cells is found, and the CCR10 mRNA expression level of peripheral blood CD4 positive T cells of atopic dermatitis patients is higher than that of healthy adult (non-patent document 8). Furthermore, IL-22 is highly expressed in the skin lesion of atopic dermatitis patients, suppresses filaggrin production of the skin and is involved in the destruction of skin barrier. CCR10 is selectively expressed in Th22 cells that highly produce IL-22 (non-patent documents 9 and 10).

The role of CTACK and CCR10 in dermatitis has been studied by using mouse dermatitis model. When chronic contact dermatitis involving type 2 helper T cell is developed in keratinocyte selective CTACK highly expressing mouse, infiltration of CCR10 positive T cells in the skin tissue and skin tumentia significantly increase as compared to wild-type mouse (non-patent document 11).

On the other hand, as pyridone compounds, compounds represented by the following formulas (A), (B) (patent documents 1, 2) and the like are known as compounds having arylamino at the 4-position and monoalkylcarbamoyl at the 5-position, a compound represented by the following formula (C) (patent document 3) and the like are known as a compound having aryloxy at the 4-position and aliphatic heterocyclic carbonyl at the 5-position, a compound represented by the following formula (D) (patent document 4) and the like are known as a compound having dialkylcarbamoyl at the 5-position, a compound represented by the following formula (E) (patent document 5) and the like are known as a compound having monoalkylcarbamoyl at the 5-position, and a compound represented by the following formula (F) (patent document 6) and the like are known as a compound having monoarylcarbamoyl at the 5-position. Besides these, for example, various pyridone compounds represented by the following formulas (G)-(K) and the like are known (patent documents 7-11).

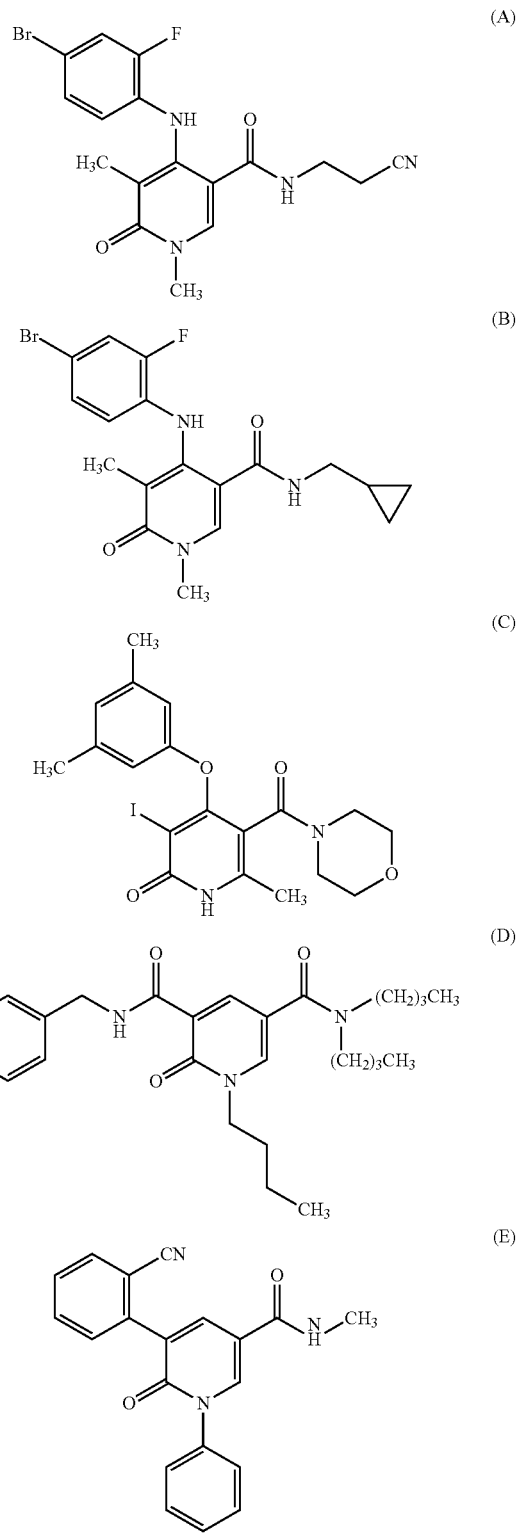

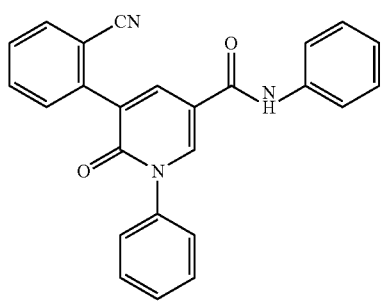

(F)

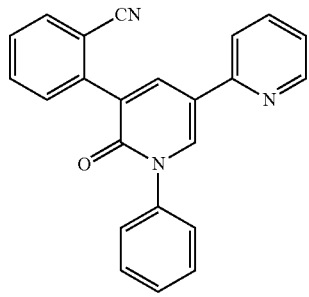

(K)

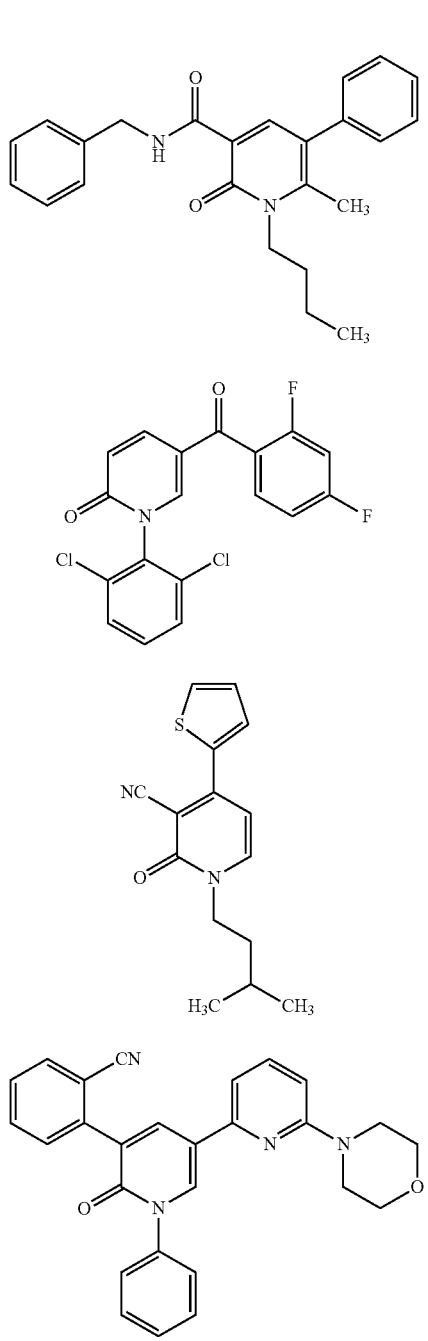

PRIOR ARTS DOCUMENTS

Patent Documents patent document 1: WO 05/051301
patent document 2: WO 06/056427
patent document 3: WO 02/024650
patent document 4: WO 03/070277
patent document 5: WO 01/096308
patent document 6: WO 03/047577
patent document 7: WO 02/053543
patent document 8: WO 05/105743
patent document 9: WO 06/030032
patent document 10: WO 06/107860
patent document 11: WO 06/109876
patent document 12: WO 13/031931

Non-Patent Documents non-patent document 1: "Clinical Dermatology", 2008, vol. 26, page 539
non-patent document 2: "Journal of Allergy and Clinical Immunology", 2006, vol. 118, page 178
non-patent document 3: "Nature Medicine", 2002, vol. 8, page 157-165
non-patent document 4: "International Immunology", 2006, vol. 18, page 1233-1242
non-patent document 5: "European Journal of Immunology", 2008, vol. 38, page 647-657
non-patent document 6: "Experimental Dermatology", 2007, vol. 17, page 30-34
non-patent document 7: "Journal of Allergy and Clinical Immunology", 2004, vol. 113, page 334
non-patent document 8: "Journal of Investigative Dermatology", 2005, vol. 125, page 1149
non-patent document 9: "Nature Immunology", 2009, vol. 10, page 857
non-patent document 10: "Nature Immunology", 2009, vol. 10, page 864
non-patent document 11: "European Journal of Immunology", 2008, vol. 38, page 647

SUMMARY OF THE INVENTION

Problems to be Solved by the Invention

An object of the present invention is to provide a pyridone compound or a pharmaceutically acceptable salt thereof, which is useful as an agent for the prophylaxis and/or treatment of skin diseases, and the like.

Means of Solving the Problems

The present invention relates to the following (1)-(33).
(1) A Pyridone Compound Represented by the Formula (I)

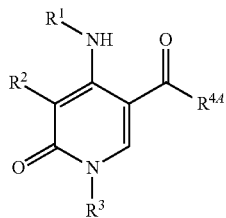

(I)

[wherein, $R^1$ represents cycloalkyl optionally having substituent(s), aryl optionally having substituent(s), an aromatic heterocyclic group optionally having substituent(s), an aliphatic heterocyclic group optionally having substituent(s), aralkyl optionally having substituent(s), or heterocyclic alkyl optionally having substituent(s),
$R^2$ represents a hydrogen atom, cyano, nitro, halogen, lower alkyl optionally having substituent(s), or $-NR^{1a}R^{1b}$ (wherein, $R^{1a}$ and $R^{1b}$ are the same or different and each represents a hydrogen atom, lower alkanoyl optionally having substituent(s), or lower alkylcarbamoyl optionally having substituent(s)),
$R^3$ represents hydroxy, lower alkyl optionally having substituent(s), lower alkenyl optionally having substituent(s), lower alkynyl optionally having substituent(s), lower alkoxy optionally having substituent(s), cycloalkyl optionally having substituent(s), heterocyclic alkyl optionally having substituent(s), or $-NR^{3a}R^{3b}$ (wherein, $R^{1a}$ and $R^{3b}$ are the same or different and each represents a hydrogen atom, lower alkyl optionally having substituent(s), cycloalkyl optionally having substituent(s), aryl optionally having substituent(s), or aralkyl optionally having substituent(s), or $R^{3a}$ and $R^{3b}$ form, together with the adjacent nitrogen atom, a nitrogen-containing heterocyclic group optionally having substituent(s)),
$R^{4A}$ represents any one of the groups represented by the following formulas ($R^{4A}$-1), ($R^{4A}$-2), ($R^{4A}$-3) or ($R^{4A}$-4)

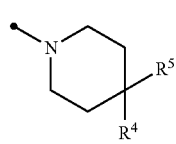

($R^{4A}$-1)

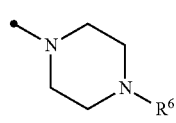

($R^{4A}$-2)

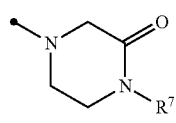

($R^{4A}$-3)

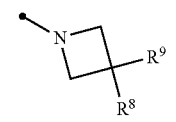

($R^{4A}$-4)

(wherein, $R^4$ and $R^5$ are the same or different and each represents a hydrogen atom, aryl optionally having substituent(s), or lower alkoxy optionally having substituent(s), or $R^4$ and $R^5$ form, together with the adjacent carbon atom, an aliphatic heterocyclic group optionally having substituent(s), $R^6$ and $R^7$ represent aryl optionally having substituent(s), $R^8$ and $R^9$ are the same or different and each represents a hydrogen atom, aryl optionally having substituent(s), or lower alkoxy optionally having substituent(s), or $R^8$ and $R^9$ form, together with the adjacent carbon atom, an aliphatic heterocyclic group optionally having substituent(s))], or a pharmaceutically acceptable salt thereof.

(2) The pyridone compound or the pharmaceutically acceptable salt thereof according to (1), wherein $R^1$ is aryl optionally having substituent(s), an aromatic heterocyclic group optionally having substituent(s), or an aliphatic heterocyclic group optionally having substituent(s).
(3) The pyridone compound or the pharmaceutically acceptable salt thereof according to (1), wherein $R^1$ is aryl optionally having substituent(s).
(4) The pyridone compound or the pharmaceutically acceptable salt thereof according to (1), wherein $R^1$ is a phenyl optionally having substituent(s).
(5) The pyridone compound or the pharmaceutically acceptable salt thereof according to (1), wherein $R^1$ is an aromatic heterocyclic group optionally having substituent(s).
(6) The pyridone compound or the pharmaceutically acceptable salt thereof according to (1), wherein $R^1$ is an aliphatic heterocyclic group optionally having substituent(s).
(7) The pyridone compound or the pharmaceutically acceptable salt thereof according to any of (1)-(6), wherein $R^2$ is a hydrogen atom, halogen or lower alkyl optionally having substituent(s).
(8) The pyridone compound or the pharmaceutically acceptable salt thereof according to any of (1)-(6), wherein $R^2$ is lower alkyl optionally having substituent(s).
(9) The pyridone compound or the pharmaceutically acceptable salt thereof according to any of (1)-(6), wherein $R^2$ is halogen.
(10) The pyridone compound or the pharmaceutically acceptable salt thereof according to any of (1)-(9), wherein $R^3$ is lower alkyl optionally having substituent(s), lower alkoxy optionally having substituent(s), or $-NR^{3a}R^{3b}$ (wherein, $R^{3a}$ and $R^{3b}$ are each as defined above).
(11) The pyridone compound or the pharmaceutically acceptable salt thereof according to any of (1)-(9), wherein $R^3$ is lower alkyl optionally having substituent(s).
(12) The pyridone compound or the pharmaceutically acceptable salt thereof according to any of (1)-(9), wherein $R^3$ is lower alkoxy optionally having substituent(s).
(13) The pyridone compound or the pharmaceutically acceptable salt thereof according to any of (1)-(9), wherein $R^3$ is $-NR^{3a}R^{3b}$ (wherein, $R^{3a}$ and $R^{3b}$ are each as defined above).
(14) The pyridone compound or the pharmaceutically acceptable salt thereof according to any of (1)-(13), wherein $R^{4A}$ is the following formula ($R^{4A}$-1)

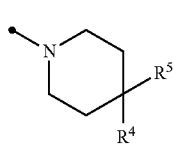

($R^{4A}$-1)

(wherein, $R^4$ and $R^5$ are each as defined above).

(15) The pyridone compound or the pharmaceutically acceptable salt thereof according to (14), wherein $R^4$ and $R^5$ are the same or different and each is a hydrogen atom, or aryl optionally having substituent(s).

(16) The pyridone compound or the pharmaceutically acceptable salt thereof according to (14), wherein $R^4$ and $R^5$ are the same or different and each is a hydrogen atom, or phenyl optionally having substituent(s).

(17) A medicament comprising, as an active ingredient, the pyridone compound or the pharmaceutically acceptable salt thereof described in any of (1)-(16).

(18) A CCR10 receptor antagonist comprising, as an active ingredient, the pyridone compound or the pharmaceutically acceptable salt thereof described in any of (1)-(16).

(19) An agent for the prophylaxis and/or treatment of a skin disease comprising, as an active ingredient, the pyridone compound or the pharmaceutically acceptable salt thereof described in any of (1)-(16).

(20) The agent for the prophylaxis and/or treatment of a skin disease according to (19), wherein the skin disease is a skin disease selected from acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(21) The agent for the prophylaxis and/or treatment of a skin disease according to (19), wherein the skin disease is a skin disease selected from contact dermatitis and atopic dermatitis.

(22) A method of inhibiting a CCR10 receptor, comprising a step of administering an effective amount of the pyridone compound or the pharmaceutically acceptable salt thereof described in any of (1)-(16).

(23) A method for the prophylaxis and/or treatment of a skin disease, comprising a step of administering an effective amount of the pyridone compound or the pharmaceutically acceptable salt thereof described in any of (1)-(16).

(24) The method according to (23), wherein the skin disease is a skin disease selected from acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(25) The method according to (23), wherein the skin disease is a skin disease selected from contact dermatitis and atopic dermatitis.

(26) The pyridone compound or the pharmaceutically acceptable salt thereof described in any of (1)-(16), for use in inhibition of a CCR10 receptor.

(27) The pyridone compound or the pharmaceutically acceptable salt thereof described in any of (1)-(16), for use in the prophylaxis and/or treatment of a skin disease.

(28) The pyridone compound or the pharmaceutically acceptable salt thereof according to (27), wherein the skin disease is a skin disease selected from acne vulgaris, drug eruption, contact dermatitis, dermatitis due to venomous moth, pollen dermatitis, urticaria, psoriasis, atopic dermatitis, Candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(29) The pyridone compound or the pharmaceutically acceptable salt thereof according to (27), wherein the skin disease is a skin disease selected from contact dermatitis and atopic dermatitis.

(30) Use of the pyridone compound or the pharmaceutically acceptable salt thereof described in any of (1)-(16), for the manufacture of a CCR10 receptor antagonist.

(31) Use of the pyridone compound or the pharmaceutically acceptable salt thereof described in any of (1)-(16), for the manufacture of an agent for the prophylaxis and/or treatment of a skin disease.

(32) The use according to (31), wherein the skin disease is a skin disease selected from acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(33) The use according to (31), wherein the skin disease is a skin disease selected from contact dermatitis and atopic dermatitis.

Effect of the Invention

The pyridone compound or the pharmaceutically acceptable salt thereof of the present invention is useful as, for example, a prophylactic and/or therapeutic agent for skin diseases and the like.

According to the present invention, a pyridone compound or a pharmaceutically acceptable salt thereof useful as a prophylactic and/or therapeutic agent for skin diseases, and the like are provided.

MODE FOR CARRYING OUT THE INVENTION

Hereinafter a compound represented by the general formula (I) is referred to as compound (I). Compounds having the other formula numbers are referred to in the same manner.

In a definition of each group in the general formula (I), examples of the lower alkyl, and the lower alkyl moiety of the lower alkoxy, the lower alkanoyl and the lower alkylcarbamoyl include linear or branched alkyl having 1-10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the lower alkenyl include linear or branched alkenyl having 2-10 carbon atoms, and more specific examples thereof include vinyl, allyl, 1-propenyl, butenyl, pentenyl, hexenyl, heptenyl, octenyl, nonenyl, decenyl and the like.

Examples of the lower alkynyl include linear or branched alkynyl having 2-10 carbon atoms, and more specific examples thereof include ethynyl, propynyl, butynyl, pentynyl, hexynyl, heptynyl, octynyl, nonynyl, decynyl and the like.

Examples of the cycloalkyl include cycloalkyl having 3-8 carbon atoms, and more specific examples thereof include cyclopropyl, cyclobutyl, cyclopentyl, cyclohexyl, cycloheptyl, cyclooctyl and the like.

Examples of the aralkyl include aralkyl having 7-16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of aryl include aryl having 6-14 carbon atoms, and more specific examples thereof include phenyl, naphthyl, azulenyl, anthryl and the like.

Examples of the aliphatic heterocyclic group, and the aliphatic heterocyclic group formed together with the adjacent carbon atom include a 3- to 7-membered monocyclic aliphatic heterocyclic group containing at least one atom selected from a nitrogen atom, an oxygen atom and a sulfur atom, a bicyclic or tricyclic fused aliphatic heterocyclic group, in which 3- to 8-membered rings are fused, and which contains at least one atom selected from a nitrogen atom, an oxygen atom and a sulfur atom, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, dihydrooxadiazolyl, isoindolinyl, dihydrobenzodioxinyl, dihydrobenzodioxepinyl, dihydroisobenzofuranyl, and the like.

Examples of the aromatic heterocyclic group include a 5- or 6-membered monocyclic aromatic heterocyclic group containing at least one atom selected from a nitrogen atom, an oxygen atom and a sulfur atom, a bicyclic or tricyclic fused aromatic heterocyclic group, in which 3- to 8-membered rings are fused, and which contains at least one atom selected from a nitrogen atom, an oxygen atom and a sulfur atom, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, benzooxadiazolyl, dioxobenzothiophenyl and the like.

Examples of the nitrogen-containing heterocyclic group, which is formed together with the adjacent nitrogen atom include a 5- or 6-membered monocyclic heterocyclic group (said the monocyclic heterocyclic group may contain other nitrogen atom(s), oxygen atom(s) or sulfur atom(s)), a bicyclic or tricyclic fused heterocyclic group, in which 3- to 8-membered rings are fused, and which contains at least one nitrogen atom (said the fused heterocyclic group may contain other nitrogen atom(s), oxygen atom(s) or sulfur atom(s)), and the like, and more specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl, dihydroisobenzofuranyl and the like.

Examples of the heterocyclic group moiety in the heterocyclic alkyl include the groups recited in the definitions of the aforementioned aliphatic heterocyclic group and the aforementioned aromatic heterocyclic group and the like.

Examples of the alkylene moiety in the heterocyclic alkyl include the groups recited as examples of the aforementioned lower alkyl from which one hydrogen atom has been removed, and more specific examples thereof include methylene, ethylene, propylene and the like.

Halogen means each atom of fluorine, chlorine, bromine or iodine.

Examples of the substituent in the lower alkyl optionally having substituent(s), the lower alkoxy optionally having substituent(s), the lower alkenyl optionally having substituent(s), the lower alkynyl optionally having substituent(s), the lower alkanoyl optionally having substituent(s), and the lower alkylcarbamoyl optionally having substituent(s), which may be the same or different and in number of 1 to 3, include substituents selected from the group comprising halogen, hydroxy, mercapto, nitro, cyano, carboxy, hydroxyimino, carbamoyl optionally having substituent(s) (examples of the substituent in the substituted carbamoyl include 1 to 2 substituents selected from cyano, $C_{1-10}$ alkyl, $C_{1-10}$ alkylsulfonyl and the like), $C_{3-8}$ cycloalkyl, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl and the like), $C_{2-11}$ alkanoyl, $C_{7-15}$ aroyl, $C_{1-10}$ alkoxycarbonyl, $C_{6-14}$ aryloxycarbonyl, aliphatic heterocyclic carbonyl optionally having substituent(s) (examples of the substituent in the substituted aliphatic heterocyclic carbonyl include 1 to 3 substituents selected from cyano and the like) and the like.

Examples of the substituent in the aryl optionally having substituent(s), the phenyl optionally having substituent(s), the aromatic heterocyclic group optionally having substituent(s), and the aralkyl optionally having substituent(s), which may be the same or different and in number of 1 to 3, include substituents selected from the group comprising halogen, hydroxy, mercapto, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy optionally having substituent(s) (examples of the substituent in the substituted $C_{1-10}$ alkoxy include 1-3 substituents selected from halogen and the like), $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, $C_{1-10}$ alkylsulfonyl, —$NR^{Xa}R^{Ya}$ (wherein $R^{Xa}$ and $R^{Ya}$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl and the like), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

The substituent of the aryl optionally having substituent(s) also includes phenyl fused with $C_{5-8}$ cycloalkyl in addition to the aforementioned substituents. Examples of the phenyl fused with $C_{5-8}$ cycloalkyl include cycloalkyl-fused phenyl having 9-12 carbon atoms, and more specific examples thereof include dihydro-1H-indenyl, 1,2,3,4-tetrahydronaphthalenyl and the like.

Examples of the substituent in the cycloalkyl optionally having substituent(s), the aliphatic heterocyclic group optionally having substituent(s), the nitrogen-containing heterocyclic group optionally having substituent(s), which is formed together with the adjacent nitrogen atom, the aliphatic heterocyclic group optionally having substituent(s), which is formed together with the adjacent carbon atom, and the heterocyclic alkyl optionally having substituent(s), which may be the same or different and in number of 1 to 3, include substituents selected from the group comprising oxo, thioxo, halogen, hydroxy, mercapto, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-3}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xb}R^{Yb}$ (wherein $R^{Xb}$ and $R^{Yb}$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl or the like), $C_{2-11}$ alkanoyl, $C_{7-15}$ aroyl, $C_{1-10}$ alkoxycarbonyl, $C_{6-14}$ aryloxycarbonyl, alkylcarbamoyl, di-$C_{1-10}$ alkylcarbamoyl and the like.

Examples of the $C_{1-10}$ alkyl shown herein and the $C_{1-10}$ alkyl moiety in the $C_{1-10}$ alkoxy, the $C_{2-11}$ alkanoyloxy, the $C_{1-10}$ alkylthio, the $C_{1-10}$ alkylsulfonyl, the $C_{2-11}$ alkanoyl, the $C_{1-10}$ alkoxycarbonyl, the $C_{1-10}$ alkylcarbamoyl, and the di-$C_{1-10}$ alkylcarbamoyl shown herein include the groups recited as examples of the aforementioned lower alkyl. The two $C_{1-10}$ alkyl moieties in the di-$C_{1-10}$ alkylcarbamoyl may be the same or different.

Examples of the $C_{3-3}$ cycloalkyl and the cycloalkyl moiety in the $C_{3-8}$ cycloalkoxy include the groups recited as examples of the aforementioned cycloalkyl. Examples of the $C_{5-8}$ cycloalkyl include cycloalkyl having 5-8 carbon atoms, and more specific examples thereof include cyclopentyl, cyclohexyl, cycloheptyl, cyclooctyl and the like.

Examples of the $C_{6-14}$ aryl and the aryl moiety in the $C_{6-14}$ aryloxy, the $C_{7-15}$ aroyl, the $C_{7-15}$ aroyloxy and the $C_{6-14}$ aryloxycarbonyl include the groups recited as examples of the aforementioned aryl.

Examples of the $C_{7-16}$ aralkyl and the aralkyl moiety in the $C_{7-16}$ aralkyloxy and the $C_{7-16}$ aralkyloxycarbonyl include the groups recited as examples of the aforementioned aralkyl.

Examples of the aliphatic heterocyclic group and the aliphatic heterocyclic group moiety in the aliphatic heterocyclic carbonyl include the groups recited as examples of the aforementioned aliphatic heterocyclic group.

The aromatic heterocyclic group and the halogen are as defined for the aforementioned aromatic heterocyclic group and the aforementioned halogen, respectively.

In each group of compound (I),
as $R^1$, phenyl optionally having substituent(s), an aromatic heterocyclic group optionally having substituent(s), or an aliphatic heterocyclic group optionally having substituent(s) is preferable, and more preferably, phenyl optionally having substituent(s) is selected, and as the substituent in the phenyl optionally having substituent(s), $C_{1-10}$ alkyl or halogen is preferable, and the number thereof is preferably 1 or 2. Also, $R^1$ is more preferably an aromatic heterocyclic group.

As $R^2$, a hydrogen atom, halogen or $C_{1-10}$ alkyl optionally having substituent(s) is preferable, and more preferably, halogen or $C_{1-10}$ alkyl is selected, and more preferably, halogen is selected.

As $R^3$, $C_{1-10}$ alkyl optionally having substituent(s), $C_{1-10}$ alkoxy optionally having substituent(s), or —$NR^{3a}R^{3b}$ (wherein $R^{3a}$ and $R^{3b}$ are each as defined above) is preferable, and more preferably, $C_{1-10}$ alkyl optionally having substituent(s) is selected, and as the substituent in the $C_{1-10}$ alkyl optionally having substituent(s), halogen, cyano, hydroxy or $C_{1-10}$ alkoxy is preferable, and the number thereof is preferably 0 or 1. Also, $R^3$ is more preferably $C_{1-10}$ alkoxy optionally having substituent(s), and as the substituent in the $C_{1-10}$ alkoxy optionally having substituent(s), halogen, hydroxy or $C_{1-10}$ alkoxy is preferable, and the number thereof is preferably 0 or 1.

When $R^{4A}$ is the following formula ($R^{4A}$-1),

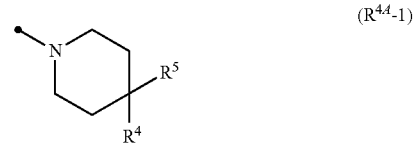

as $R^4$, a hydrogen atom is preferable.
As $R^5$, a phenyl optionally having substituent(s) is preferable, and as the substituent in the phenyl optionally having substituent(s), halogen is preferable, and the number thereof is preferably 0 or 1.

As compound (I), a compound wherein one or more of the above-mentioned preferable substituents are respectively combined is preferable. Furthermore, compounds obtained by limiting compounds (I) described in (2)-(16) in "Means of Solving the Problems" with preferable substituents shown above are preferable. Compounds obtained by limiting compounds (I) described in (2)-(16) in "Means of Solving the Problems" with a combination of two or more preferable substituents shown above are more preferable.

The pharmaceutically acceptable salt of compound (I) comprises, for example, pharmaceutically acceptable acid addition salts, metal salts, ammonium salts, organic amine addition salts, amino acid addition salts and the like. Examples of the pharmaceutically acceptable acid addition salt of compound (I) include, but are not limited to, inorganic acid salts such as hydrochloride, hydrobromide, nitrate, sulfate, phosphate and the like, organic acid salts such as acetate, oxalate, maleate, fumarate, citrate, benzoate, methanesulfonate and the like, and the like. Examples of the pharmaceutically acceptable metal salt include, but are not limited to, sodium salt, potassium salt, magnesium salt, calcium salt, aluminum salt, zinc salt and the like. Examples of the pharmaceutically acceptable ammonium salt include, but are not limited to, salts such as ammonium salt, tetramethylammonium salt and the like. Examples of the pharmaceutically acceptable organic amine addition salt include, but are not limited to, addition salts of morpholine, piperidine and the like. Examples of the pharmaceutically acceptable amino acid addition salt include, but are not limited to, addition salts of lysine, glycine, phenylalanine, aspartic acid, glutamic acid and the like.

Also, the pharmaceutically acceptable salt of compound (I) comprises quaternary ammonium salt. The quaternary ammonium salt is a compound wherein a nitrogen atom is quaternized by Rx (Rx is, for example, lower alkyl or aralkyl and the like, wherein lower alkyl and aralkyl are as defined above).

Further, the pharmaceutically acceptable salt of compound (I) includes N-oxide form. The N-oxide form is a compound wherein a nitrogen atom is oxidized. An N-oxide form of compound (I) can be obtained from compound (I) wherein it is not N-oxide by any oxidation method and using an oxidation reagent such as m-chloroperbenzoic acid, air oxidation, liver extract and the like.

The skin disease in the present invention refers to a disease with a lesion appearing on the skin. Specific examples include acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies, linear dermatitis and the like. However, the skin diseases in the present invention are not limited to these.

The treatment in the present invention refers to conversion, mitigation or inhibition of the progression of the disease or condition to be applied, or one or more symptoms of such disease or condition. It further includes application for inhibition of the progression of symptoms before remission of the disease, or when they are mild. In skin diseases, aggravation and remission may repeat periodically and chronically. The therapeutic agent and/or prophylactic agent of the present invention are/is also used for prolongation of the remission period or prevention of aggravation. The prophylactic agent is also used for the prevention of the m onset of the disease.

The aggravation used in the present specification refers to exacerbation of the symptoms of a disease.

The remission used in the present specification refers to temporary or permanent mitigation or disappearance of the symptoms of a disease. Time of remission refers to a remission state, and remission length means a period when the state of remission continues.

The present invention also comprises prodrugs of compound (I). The prodrug of compound (I) is a compound converted to compound (I) as a result of a reaction with an enzyme, gastric acid and the like in the body. As prodrug, many kinds of prodrugs are known, and a suitable prodrug can be selected from a known document (for example, Development of Pharmaceutical Product, Hirokawa Publishing INC., 1990, vol. 7, page 163) and synthesized by a known method. Examples of the prodrug of compound (I) when compound (I) has amino include a compound wherein the amino is acylated, alkylated or phosphorylated; examples thereof when compound (I) has hydroxy include a compound wherein the hydroxy is acylated, alkylated, phosphorylated or borated; and examples thereof when compound (I) has carboxy include a compound wherein the carboxy is esterified or amidated and the like. Also, the prodrug of compound (I) may be any of hydrate, non-hydrate and solvate and, like compound (I), may form a salt with a pharmaceutically acceptable acid or base.

A preferable compound used in the present specification is a compound having not only pharmacological activity but also desirable properties in one or more items from various evaluation items requested for pharmaceutical products such as a prophylactic and/or therapeutic agent for skin diseases and the like, such as physical stability, stability under physiological conditions, safety for living organisms and the like.

Compound (I) or a pharmaceutically acceptable salt thereof of the present invention sometimes shows an unpreferable action on living organisms. Even in such case, it can exhibit usefulness as a prophylactic and/or therapeutic agent for skin diseases or as a pharmaceutical product, by employing an appropriate dose and administration method, while reducing the unpreferable action.

Among compound (I) of the present invention, stereoisomers such as geometric isomer, optical isomer and the like, tautomer and the like may exist. The present invention comprises all possible isomers and mixtures thereof including them, and the mixing ratio thereof may be any value.

Compound (I) or a pharmaceutically acceptable salt thereof of the present invention is sometimes present as an adduct with water or various solvents, and such adduct is also comprised in the present invention.

A part or all of the respective atoms in compound (I) may be replaced by corresponding isotope atom(s), respectively, and the present invention also comprises such compounds replaced by such isotope atom(s). For example, a part or all of hydrogen atoms in compound (I) may be a hydrogen atom having an atomic weight of 2 (deuterium atom). A compound incorporating a radioisotope such as $^3$H (tritium) or $^{14}$C from among the isotopes is useful for examining the tissue distribution of a compound and screening for an agent for the prophylaxis and/or treatment of skin diseases.

For example, a compound wherein a part or all of the respective atoms in compound (I) is/are replaced by corresponding isotope atom(s), respectively, can be produced by using a commercially available building block and in the same manner as in each of the production methods described in the following. Also, a compound wherein a part or all of the hydrogen atoms in compound (I) is/are replaced by deuterium atom(s) can be synthesized by, for example, 1) a method using deuterium peroxide, to deuterate carboxylic acid and the like under basic conditions (U.S. Pat. No. 3,849,458), 2) a method using an iridium complex as a catalyst, to deuterate alcohol, carboxylic acid and the like by using deuterium oxide as a deuterium source [J. Am. Chem. Soc., Vol. 124, No. 10, 2092 (2002)], 3) a method using palladium carbon as a catalyst, to deuterate fatty acid by using only a deuterium gas as a deuterium source [LIPIDS, Vol. 9, No. 11, 913(1974)], 4) a method using a metal such as platinum, palladium, rhodium, ruthenium, iridium and the like as catalysts, to deuterate acrylic acid, methyl acrylate, methacrylic acid, methyl methacrylate and the like by using deuterium oxide, or deuterium oxide and deuterium gas, as a deuterium source (JP-B-5-19536, JP-A-61-277648 and JP-A-61-275241), 5) a method using a catalyst such as palladium, nickel, copper or chromite copper and the like, to deuterate acrylic acid, methyl methacrylate and the like by using deuterium oxide as deuterium source (JP-A-63-198638) and the like.

The isotope atom used in the present specification refers to an atom having an atom value or mass number different from the atom value or mass number generally found in nature. Examples of the isotope atom in the compound of the present invention include $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$ and the like.

Next, production methods of compound (I) are explained.

Incidentally, in the production methods shown below, when a defined group changes under the conditions of the production methods or is inappropriate for performing the production methods, the desired compound can be produced by using the methods for introducing and removing a protecting group conventionally used in the synthetic organic chemistry (for example, methods described in Protective Groups in Organic Synthesis, third edition, T. W. Greene, John Wiley & Sons Inc., 1999 and the like) and the like. Also, if necessary, the order of the reaction steps such as substituent introduction and the like, can be changed.

Production Method 1

Among compounds (I), compound (Ia) wherein $R^2$ is halogen can be produced according to, for example, the following steps.

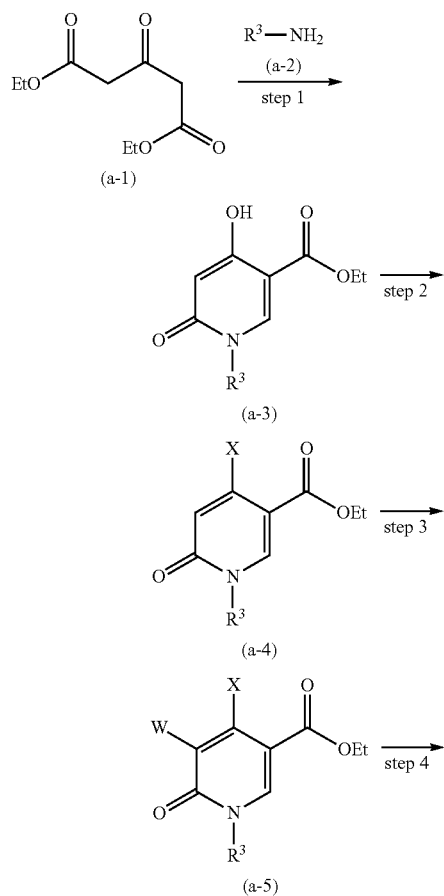

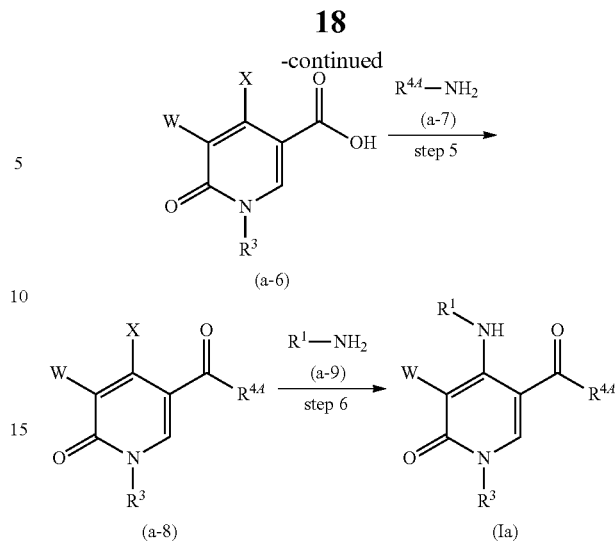

[wherein $R^1$, $R^3$ and $R^{4.4}$ are each as defined above, W represents halogen, Et represents ethyl, X represents halogen or a leaving group such as sulfonate (for example, methanesulfonyloxy, p-toluenesulfonyloxy, trifluoromethanesulfonyloxy or the like) or the like]

step 1

Compound (a-3) can be produced by reacting commercially available diethyl 3-oxopentanedioate (a-1) in the presence of 1-5 equivalents of trialkyl orthoformate and 1-10 equivalents of acetic anhydride at a temperature between 80° C. and 150° C. for 5 min to 72 hr, concentrating same under reduced pressure, adding a solvent and 1-10 equivalents of compound (a-2), and reacting the mixture at a temperature between −20° C. and 100° C. for 5 min to 72 hr.

Examples of the trialkyl orthoformate include trimethyl orthoformate, triethyl orthoformate and the like.

Examples of the solvent include acetonitrile, tetrahydrofuran (THF), 1,2-dimethoxyethane (DME), methanol, ethanol, N,N-dimethylformamide (DMF), water and the like, and these are used singly or in a mixture.

Compound (a-2) can be obtained as a commercially available product, or can be obtained by a known method [for example, Jikken Kagaku Kouza, 5th ed., vol. 14, p. 351, Maruzen Company, Limited (2005) and the like] or a method analogous thereto.

Incidentally, depending on the kind of compound (a-2), the reactivity is poor and the reaction up to compound (a-3) may not be completed. In such a case, the compound can be produced by once isolating the reaction intermediate, adding a solvent and, if necessary, preferably 1 equivalent to a large excess amount of an additive, and reacting the mixture for 5 min to 72 hr at a temperature between −20° C. and the boiling point of the solvent to be used.

Examples of the additive include pyridine, triethylamine, diisopropylethylamine, 1,8-diazabicyclo[5.4.0]undec-7-ene (DBU) and the like.

Examples of the solvent include dichloromethane, chloroform, 1,2-dichloroethane, acetonitrile, toluene, diethyl ether, THF, DME, dioxane, DMF, N,N-dimethylacetamide (DMA), N-methylpyrrolidone (NMP) and the like, and these are used singly or in a mixture.

step 2

When X is halogen, compound (a-4) can be produced by reacting compound (a-3) in a solvent or without solvent in the presence of 1 equivalent to a large excess amount of a halogenating agent and, if necessary, a catalytic amount to 1 equivalent of an additive, at a temperature between −20° C. and 150° C. for 5 min to 72 hr.

Examples of the halogenating agent include phosphorus oxychloride, phosphorus pentachloride, phosphorus trichloride, thionyl chloride, phosphorus oxybromide, phosphorus tribromide and the like.

Examples of the additive include DMF, pyridine, diisopropylethylamine and the like.

Examples of the solvent include dichloromethane, chloroform, 1,2-dichloroethane, acetonitrile, toluene, diethyl ether, THF, DME, dioxane, DMF, DMA, NMP, pyridine and the like, and these are used singly or in a mixture.

When X is sulfonate, compound (a-4) can be produced by reacting compound (a-3) in a solvent or without solvent in the presence of 1-10 equivalents of a sulfonylating agent and 1-10 equivalents of an additive at a temperature between −78° C. and 150° C. for 5 min to 72 hr.

Examples of the sulfonylating agent include methanesulfonyl chloride, p-toluenesulfonyl chloride, trifluoromethanesulfonic anhydride and the like.

Examples of the additive include pyridine, triethylamine, diisopropylethylamine, DBU and the like.

Examples of the solvent include dichloromethane, chloroform, 1,2-dichloroethane, acetonitrile, toluene, diethyl ether, THF, DME, dioxane, DMF, DMA, NMP and the like, and these are used singly or in a mixture.

step 3

Compound (a-5) can be produced by reacting compound (a-4) in a solvent or without solvent in the presence of 1-5 equivalents of a halogenating agent, at a temperature between −30° C. and 150° C. for 5 min to 72 hr.

Examples of the halogenating agent include chlorine, bromine, iodine, N,N,N,N-tetra-n-butylammonium tribromide, N-chlorosuccinimide, N-bromosuccinimide, N-iodosuccinimide, 1-(chloromethyl)-4-fluoro-1,4-diazoniabicyclo[2.2.2]octane-bis(tetrafluoroborate) and the like.

Examples of the solvent include acetone, 1,4-dioxane, acetonitrile, chloroform, dichloromethane, THF, DME, ethyl acetate, methanol, ethanol, DMF, acetic acid, water and the like, and these are used singly or in a mixture.

step 4

Compound (a-6) can be produced by treating compound (a-5) with 1 equivalent to a large excess amount of a base in a solvent for 5 min to 72 hr at a temperature between 0° C. and the boiling point of the solvent to be used.

Examples of the base include potassium carbonate, lithium hydroxide, potassium hydroxide, sodium hydroxide, sodium methoxide and the like.

Examples of the solvent include solvents including water, and examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine and the like. These are used by mixing with water, or by mixing them and adding water thereto.

step 5

Compound (a-8) can be produced by reacting compound (a-6) and 1-5 equivalents of compound (a-7) in a solvent in the presence of 1-5 equivalents of a condensing agent and, if necessary, 1-5 equivalents of an additive, for 5 min to 72 hr at a temperature between −20° C. and the boiling point of the solvent to be used.

Examples of the condensing agent include 1,3-dicyclohexanecarbodiimide (DCC), 1-ethyl-3-(3-dimethylaminopropyl)carbodiimide hydrochloride (EDC), carbonyldiimidazole (CDI), 2-chloro-1-methylpyridinium iodide, O-(7-azabenzotriazol-1-yl)-N,N,N',N'-tetramethyluroniumhexafluorophosphate (HATU) and the like.

Examples of the additive include 1-hydroxybenzotriazole monohydrate (HOBt), N,N-diisopropylamine and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine, water and the like, and these are used singly or in a mixture.

Compound (a-7) is obtained as a commercially available product, or can be obtained by a known method [for example, Jikken Kagaku Kouza, 5th ed., vol. 14, p. 537, Maruzen Company, Limited (2005) and the like] or a method analogous thereto.

step 6

Compound (Ia) can be produced by reacting compound (a-8) and 1 equivalent to a large excess amount of compound (a-9) in a solvent, preferably in the presence of 1 equivalent to a large excess amount of a base at a temperature between −78° C. and 150° C. for 5 min to 72 hr.

Examples of the base include n-butyllithium, sec-butyllithium, tert-butyllithium, phenyllithium, lithiumdiisopropylamide, hexamethyldisilasanelithium, potassium tert-butoxide, potassium carbonate, sodium hydride and the like.

Examples of the solvent include dichloromethane, chloroform, 1,2-dichloroethane, toluene, diethyl ether, THF, DME, dioxane, hexane and the like, and these are used singly or in a mixture.

As an alternative method, compound (Ia) can also be produced by reacting compound (a-8) and 1 equivalent to a large excess amount of compound (a-9) in a solvent, preferably in the presence of 0.1 equivalent-10 equivalents of an acid for 5 min to 72 hr at a temperature between 20° C. and the boiling point of the solvent to be used.

Examples of the acid include hydrochloric acid, sulfuric acid, formic acid, acetic acid, trifluoroacetic acid, p-toluenesulfonic acid, methanesulfonic acid and the like, and these are used singly or in a mixture.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Also, as an alternative method, compound (Ia) can be produced by reacting compound (a-8) and preferably 1-10 equivalents of compound (a-9) in a solvent, preferably in the presence of 0.1-10 equivalents of a base and preferably 0.001-1 equivalent of a palladium catalyst, and 0.001-1 equivalent of a phosphine compound, if necessary, for 5 min to 72 hr at a temperature between −20° C. and the boiling point of the solvent to be used.

Examples of the base include potassium carbonate, cesium carbonate, potassium phosphate, potassium tert-butoxide, sodium tert-butoxide, sodium disilazide and the like.

Examples of the palladium catalyst include palladium acetate, palladium trifluoroacetate, tris(dibenzylideneacetone)dipalladium and a chloroform adduct thereof, tetrakis(triphenylphosphine)palladium, 1,1'-bis(diphenylphosphino)ferrocenedichloropalladium dichloromethane 1:1 adduct and the like.

Examples of the phosphine compound include 2,2'-bis(diphenylphosphino)-1,1'-binaphthyl, o-tolylphosphine, tributylphosphine, di-tert-butyldiphenylphosphine, 2-(di-tert-butylphosphino)biphenyl, 2-(dicyclohexylphosphino)biphenyl and the like.

Examples of the solvent include toluene, xylene, ethyl acetate, acetonitrile, diethyl ether, THF, DME, dioxane and the like, and these are used singly or in a mixture.

Compound (a-9) can be obtained as a commercially available product, or can be obtained by a known method [for example, Jikken Kagaku Kouza, 5th ed., vol. 14, p. 351, Maruzen Company, Limited (2005) and the like] or a method analogous thereto.

Production Method 2

Among compounds (I), compound (Ib) wherein $R^2$ is a hydrogen atom, cyano or lower alkyl optionally having substituent(s) can be produced according to the following steps.

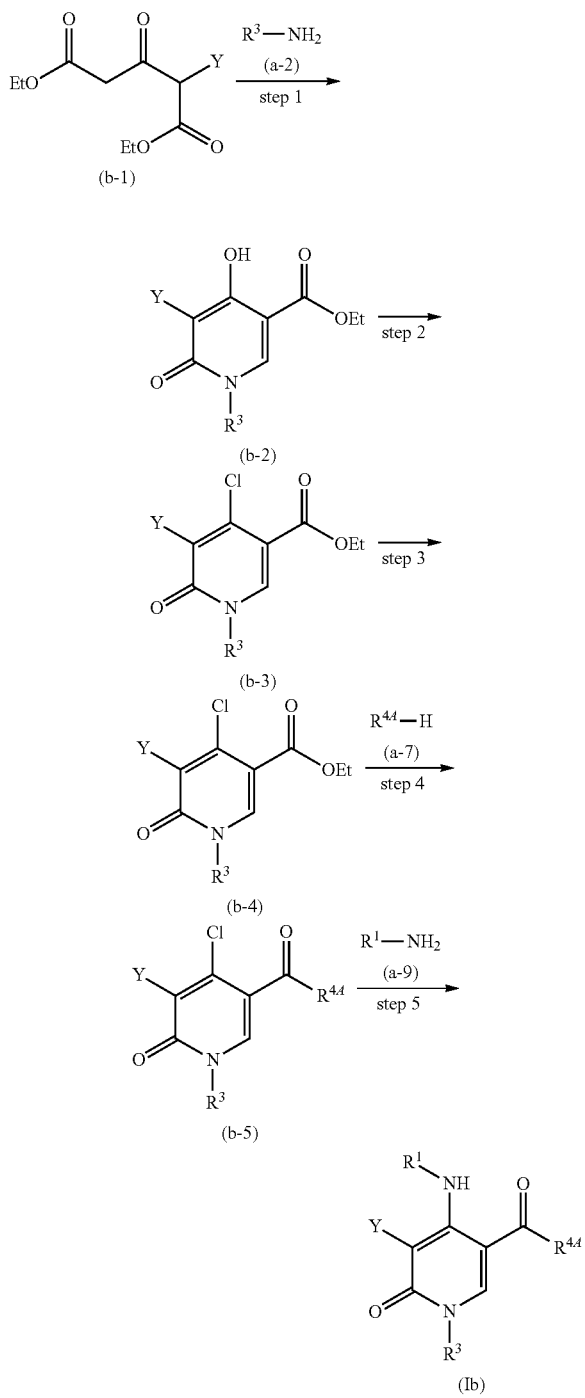

(wherein $R^1$, $R^3$, $R^{4A}$ and Et are each as defined above, Y represents a hydrogen atom, cyano or lower alkyl optionally having substituent(s))

step 1

Compound (b-2) can be produced using compound (b-1) and compound (a-2) by a method similar to that of Production method 1, step 1.

Compound (b-1) is obtained as a commercially available product, or can be obtained by a known method [for example, the method described in Journal of the Chemical Society, vol. 85, p. 1760 (1904), the method described in Australian J. of Chemistry, vol. 52, p. 1013 (1999), and the like] or a method analogous thereto.

step 2

Compound (b-3) can be produced using compound (b-2) by a method similar to that of Production method 1, step 2.

step 3

Compound (b-4) can be produced using compound (b-3) by a method similar to that of Production method 1, step 4.

step 4

Compound (b-5) can be produced using compound (b-4) and compound (a-7) by a method similar to that of Production method 1, step 5.

step 5

Compound (Ib) can be produced using compound (b-5) and compound (a-9) by a method similar to that of Production method 1, step 6.

Production Method 3

Among compounds (I), compound (Ia) wherein $R^2$ is halogen can also be produced according to the following steps.

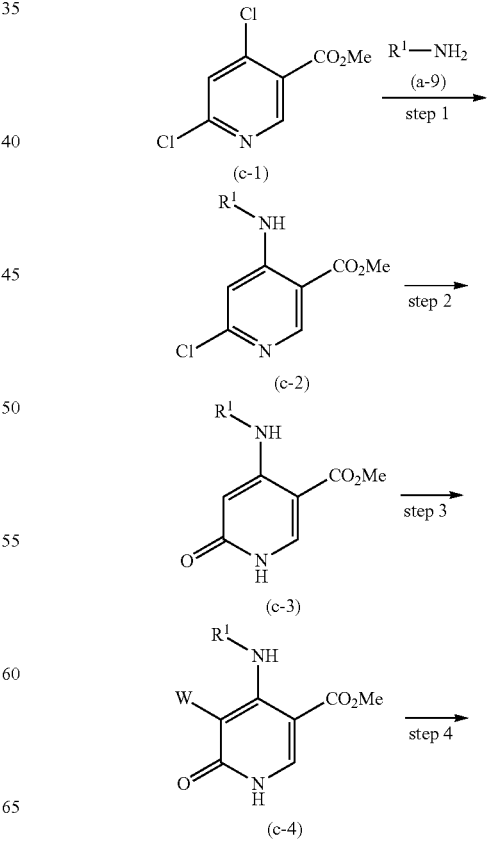

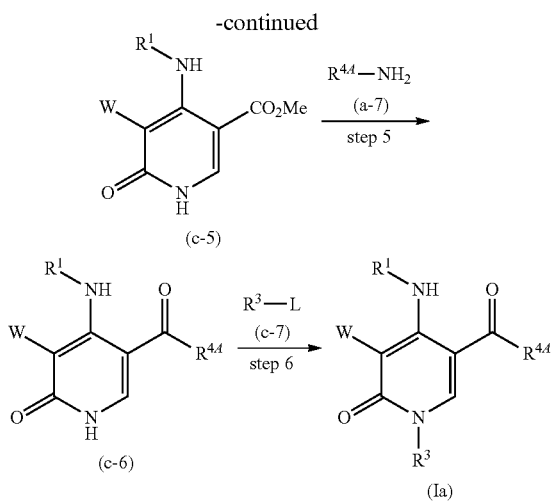

[wherein $R^1$, $R^3$, $R^{4A}$ and W are each as defined above, L represents halogen, or a leaving group such as sulfonate (for example, methanesulfonyloxy, p-toluenesulfonyloxy, trifluoromethanesulfonyloxy or the like) or the like, and Me represents methyl]

step 1

Compound (c-2) can be produced using commercially available methyl 4,6-dichloronicotinate (c-1) and compound (a-9) by a method similar to that of Production method 1, step 6.

step 2

Compound (c-3) can be produced by treating compound (c-2) with 1-10 equivalents of an additive, if necessary, in a solvent for 5 min to 100 hr at a temperature between 0° C. and the boiling point of the solvent to be used.

Examples of the additive include ammonium acetate, sodium methoxide and the like.

As the solvent, water, or a mixed solution of water and organic solvent is used. Examples of the organic solvent include acetic acid, methanol and the like, and these are used singly or in a mixture.

As an alternative method, compound (c-3) can also be produced by treating compound (c-2) in a solvent with 1 equivalent to a large excess amount of a base for 5 min to 72 hr at a temperature between 0° C. and the boiling point of the solvent to be used.

Examples of the base include potassium carbonate, lithium hydroxide, potassium hydroxide, sodium hydroxide, sodium methoxide and the like.

Examples of the solvent include solvents including water, and examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine and the like. These are used by mixing with water, or by mixing them and adding water thereto.

step 3

Compound (c-4) can be produced using compound (c-3) by a method similar to that of Production method 1, step 3.

step 4

Compound (c-5) can be produced using compound (c-4) by a method similar to that of Production method 1, step 4.

step 5

Compound (c-6) can be produced using compound (c-5) and compound (a-7) by a method similar to that of Production method 1, step 5.

step 6

Compound (Ia) can be produced by reacting compound (c-6) and 1 equivalent to a large excess amount of compound (c-7) in a solvent in the presence of 1 equivalent to a large excess amount of a base at a temperature between −78° C. and 150° C. for 5 min to 72 hr.

Examples of the base include n-butyllithium, sec-butyllithium, tert-butyllithium, phenyllithium, lithiumdiisopropylamide, hexamethyldisilasanelithium, potassium tert-butoxide, potassium carbonate, sodium hydride and the like.

Examples of the solvent include dichloromethane, chloroform, 1,2-dichloroethane, toluene, diethyl ether, THF, DME, dioxane, hexane and the like, and these are used singly or in a mixture.

Also, as an alternative method, compound (Ia) can be produced by reacting compound (c-6) and 1 equivalent to a large excess amount of compound (c-7) in a solvent in the presence of 0.1-10 equivalents of an acid, if necessary, for 5 min to 72 hr at a temperature between 20° C. and the boiling point of the solvent to be used.

Examples of the acid include hydrochloric acid, sulfuric acid, formic acid, acetic acid, trifluoroacetic acid, p-toluenesulfonic acid, methanesulfonic acid and the like, and these are used singly or in a mixture.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Compound (c-7) can be obtained as a commercially available product, or can be obtained by a known method [for example, Jikken Kagaku Kouza, 5th ed., vol. 14, p. 351, Maruzen Company, Limited (2005) and the like] or a method analogous thereto.

Production Method 4

Among compounds (I), compound (Id) wherein $R^2$ is a hydrogen atom or fluorine atom can be produced according to the following steps.

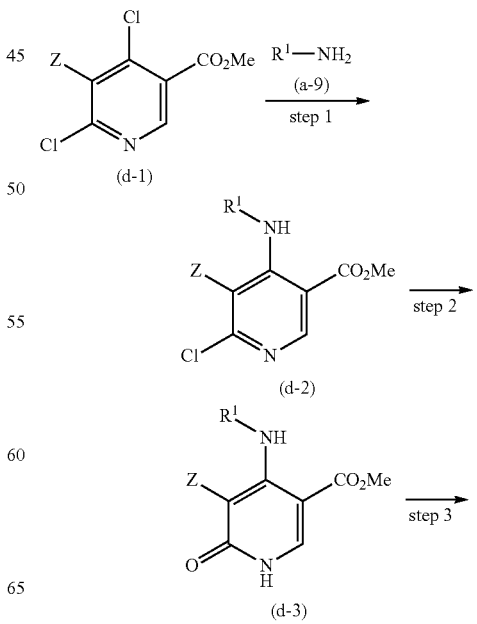

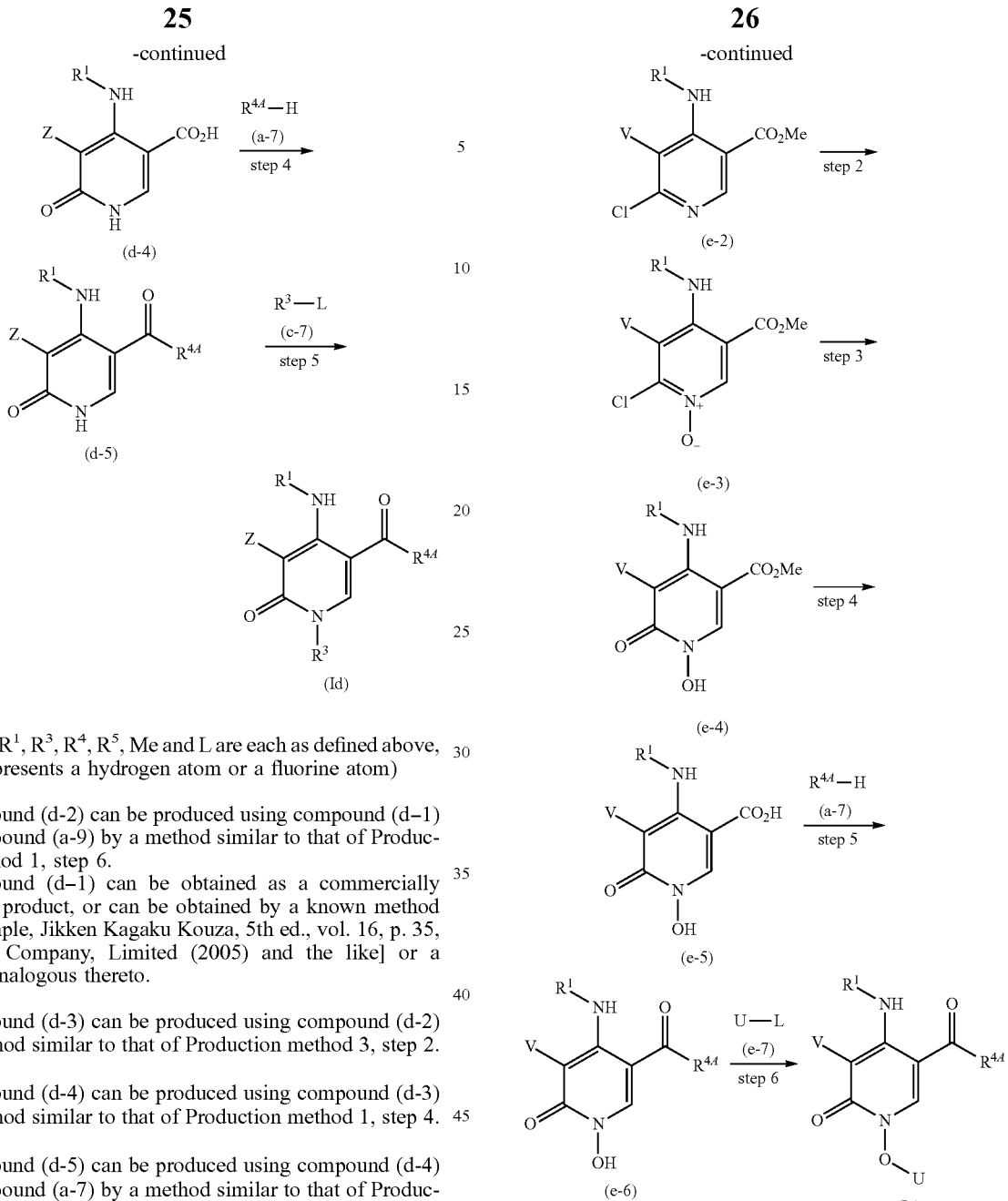

(wherein $R^1$, $R^3$, $R^4$, $R^5$, Me and L are each as defined above, and Z represents a hydrogen atom or a fluorine atom)

step 1

Compound (d-2) can be produced using compound (d-1) and compound (a-9) by a method similar to that of Production method 1, step 6.

Compound (d-1) can be obtained as a commercially available product, or can be obtained by a known method [for example, Jikken Kagaku Kouza, 5th ed., vol. 16, p. 35, Maruzen Company, Limited (2005) and the like] or a method analogous thereto.

step 2

Compound (d-3) can be produced using compound (d-2) by a method similar to that of Production method 3, step 2.

step 3

Compound (d-4) can be produced using compound (d-3) by a method similar to that of Production method 1, step 4.

step 4

Compound (d-5) can be produced using compound (d-4) and compound (a-7) by a method similar to that of Production method 1, step 5.

step 5

Compound (Id) can be produced using compound (d-5) by a method similar to that of Production method 3, step 6.

Production Method 5

Among compounds (I), compound (Ie) wherein $R^3$ is a hydrogen atom or halogen, and $R^3$ is lower alkoxy optionally having substituent(s) can be produced according to the following steps.

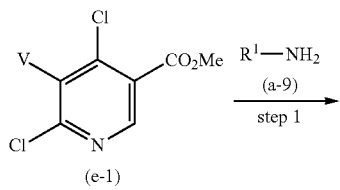

(wherein $R^1$, $R^4$, $R^5$, Me and L are each as defined above, U represents the lower alkyl moiety optionally having substituent(s) of the lower alkoxy optionally having substituent(s) for $R^3$, and V represents a hydrogen atom or halogen)

step 1

Compound (e-2) can be produced using compound (e-1) and compound (a-9) by a method similar to that of Production method 1, step 6.

Compound (e-1) is obtained as a commercially available product, or can be obtained by a known method [for example, the method described in Jikken Kagaku Kouza, 5th ed., vol. 16, p. 35, Maruzen Company, Limited (2005) and the like] or a method analogous thereto.

step 2

Compound (e-3) can be produced by treating compound (e-2) with 1 equivalent to a large excess amount of an oxidant, and if necessary, 1 equivalent to a large excess amount of an additive, in a solvent or without solvent at a temperature between 0° C., and 100° C. for 5 min to 72 hr.

Examples of the oxidant include metachlorobenzoic acid (mCPBA), urea hydrogen peroxide (UHP), hydrogen peroxide and the like, and these are used singly or in a mixture.

Examples of the additive include phthalic anhydride, trifluoroacetic anhydride (TFAA), sulfuric acid, acetic acid and the like, and these are used singly or in a mixture.

Examples of the solvent include dichloromethane, chloroform, acetonitrile, THF, methanol, ethanol, water and the like, and these are used singly or in a mixture.

step 3

Compound (e-4) can be produced by treating compound (e-3) with 1 equivalent to a large excess amount of an additive in a solvent or without solvent at a temperature between 0° C. and 100° C. for 5 min to 72 hr.

Examples of the additive include potassium hydroxide, sodium hydroxide, TFAA, acetic anhydride, acetic acid and the like, and these are used singly or in a mixture.

Examples of the solvent include 1,4-dioxane, THF, methanol, ethanol, water and the like, and these are used singly or in a mixture.

step 4

Compound (e-5) can be produced using compound (e-4) by a method similar to that of Production method 1, step 4.

step 5

Compound (e-6) can be produced using compound (e-5) and compound (a-7) by a method similar to that of Production method 1, step 5.

step 6

Compound (Ie) can be produced using compound (e-6) and compound (e-7) by a method similar to that of Production method 3, step 6.

Compound (e-7) is obtained as a commercially available product, or can be obtained by a known method [for example, Jikken Kagaku Kouza, 5th ed., vol. 14, p. 351, Maruzen Company, Limited (2005) and the like] or a method analogous thereto.

Production Method 6

Among compounds (I), compound (If) wherein $R^2$ is nitro, and compounds (Ig)-(Ii) wherein $R^2$ is —$NR^{1a}R^{1b}$ (wherein $R^{1a}$ and $R^{1b}$ are each as defined above) can be produced according to the following steps.

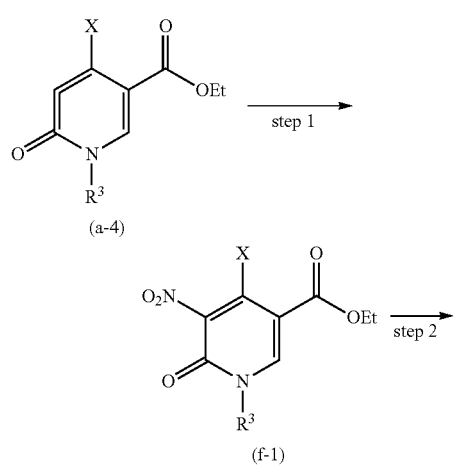

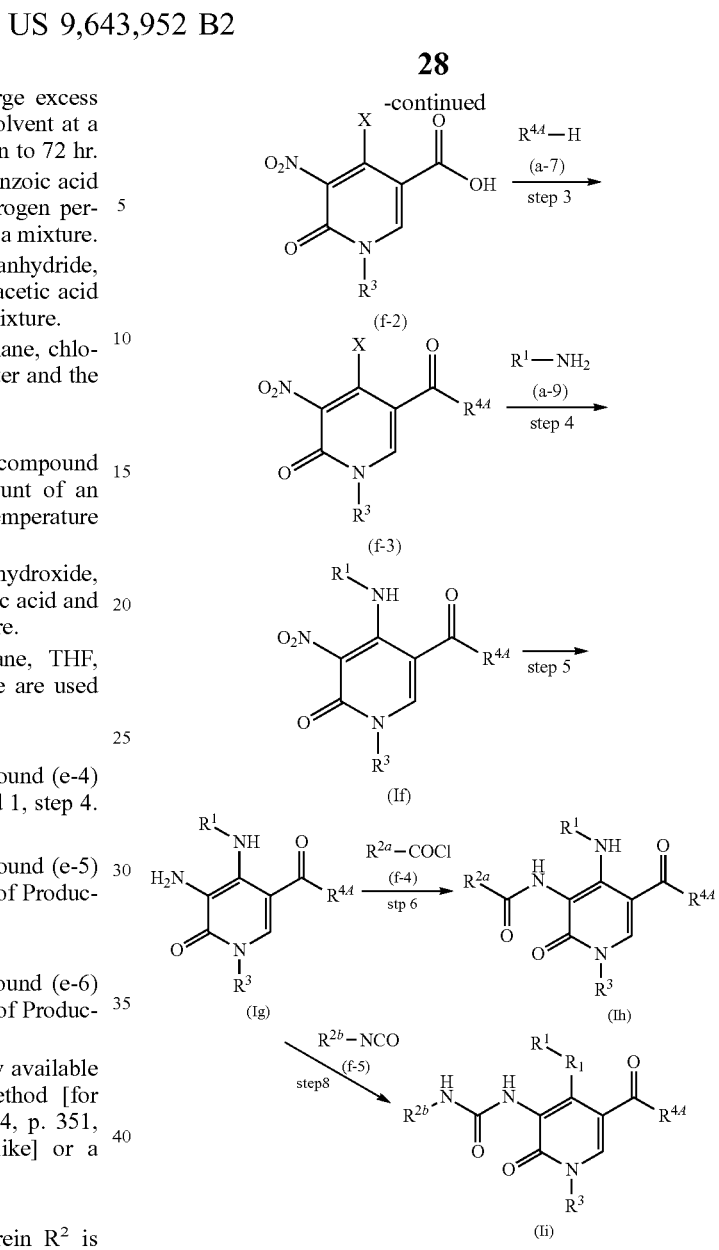

(wherein $R_1$, $R^3$, $R^{4A}$, X and Et are each as defined above, $R^{2a}$ represents the lower alkyl moiety optionally having substituent(s) of the lower alkanoyl optionally having substituent(s) when $R^{1a}$ or $R^{1b}$ is lower alkanoyl optionally having substituent(s), and $R^{2b}$ is the lower alkyl moiety optionally having substituent(s) of the lower alkylcarbamoyl optionally having substituent(s) when $R^{1a}$ or $R^{1b}$ is lower alkylcarbamoyl optionally having substituent(s))

step 1

Compound (f-1) can be produced by treating compound (a-4) with 1-10 equivalents of a nitric acid compound and, where necessary, 1 equivalent to a large excess amount of an additive, without solvent or in a solvent, for 5 min-72 hr at a temperature between −20° C. and the boiling point of the solvent to be used.

Examples of the nitric acid compound include concentrated nitric acid, fuming nitric acid, sodium nitrate, potassium nitrate and the like.

Examples of the additive include concentrated sulfuric acid, concentrated hydrochloric acid, acetic acid and the like.

Examples of the solvent include dichloromethane, chloroform, 1,2-dichloroethane, nitromethane, nitroethane, water and the like, and these are used singly or in a mixture.

step 2

Compound (f-2) can be produced using compound (f-1) by a method similar to that of Production method 1, step 4.

step 3

Compound (f-3) can be produced using compound (f-2) and compound (a-7) by a method similar to that of Production method 1, step 5.

step 4

Compound (If) can be produced using compound (f-3) and compound (a-9) by a method similar to that of Production method 1, step 6.

step 5

Compound (Ig) can be produced by treating compound (If) in a solvent under a hydrogen atmosphere or in the presence of 2 equivalents to a large excess amount of a hydrogen source, in the presence of 0.01-50 wt % of a catalyst, at a temperature between −20° C. and the boiling point of the solvent to be used, under normal pressure or pressurization for 5 min to 72 hr.

Examples of the catalyst include palladium carbon, palladium, palladium hydroxide, palladium acetate, palladium black and the like.

Examples of the hydrogen source include formic acid, ammonium formate, sodium formate, cyclohexadiene, hydrazine and the like.

Examples of the solvent include methanol, ethanol, toluene, ethyl acetate, acetonitrile, diethyl ether, THF, DME, dioxane, DMF, DMA, NMP, water and the like, and these are used singly or in a mixture.

step 6

Compound (Ih) can be produced by reacting compound (Ig) and 1-10 equivalents of compound (f-4) in a solvent in the presence of 1-10 equivalents of a base for 5 min to 72 hr at a temperature between −20° C. and the boiling point of the solvent to be used.

Examples of the base include sodium carbonate, potassium carbonate, pyridine, triethylamine, diisopropylethylamine, DBU and the like.

Examples of the solvent include dichloromethane, chloroform, 1,2-dichloroethane, acetonitrile, toluene, diethyl ether, THF, DME, dioxane, DMF, DMA, NMP and the like, and these are used singly or in a mixture.

Compound (f-4) can be obtained as a commercially available product or by a known method [for example, Jikken Kagaku Kouza, 5th ed., vol. 16, p. 98, Maruzen Company, Limited (2005) and the like] or a method analogous thereto.

step 7

Compound (Ii) can be produced by reacting compound (Ig) and 1-10 equivalents of compound (f-5) in a solvent in the presence of 1-10 equivalents of a base, for 5 min to 72 hr at a temperature between −20° C. and the boiling point of the solvent to be used.

Examples of the base include sodium carbonate, potassium carbonate, pyridine, triethylamine, diisopropylethylamine, DBU and the like.

Examples of the solvent include dichloromethane, chloroform, 1,2-dichloroethane, acetonitrile, toluene, diethyl ether, THF, DME, dioxane, DMF, DMA, NMP and the like, and these are used singly or in a mixture.

Compound (f-5) is obtained as a commercially available product, or can be obtained by a known method [for example, Jikken Kagaku Kouza, 5th ed., vol. 14, p. 537, Maruzen Company, Limited (2005) and the like] or a method analogous thereto.

Conversion of a functional group contained in $R^1$, $R^2$, $R^3$, $R^{4A}$ and the like in compound (I) and each intermediate in the above-mentioned Production methods can also be performed by a known method (e.g., the method described in Comprehensive Organic Transformations 2nd edition, R. C. Larock, Vch Verlagsgesellschaft Mbh, 1999 and the like) or a method analogous thereto.

The intermediates and the desired compounds in the above-mentioned production methods can be isolated and purified by applying separation and purification methods usually used in the synthetic organic chemistry such as filtration, extraction, washing, drying, concentration, recrystallization, various chromatographies and the like. Also, intermediates can also be subjected to a next reaction without particular purification.

To obtain a salt of compound (I), when compound (I) is obtained in a form of a salt, it can be directly purified. Or when compound (I) is obtained in a free form, it may be dissolved or suspended in a suitable solvent, and an acid or a base is added thereto to form a salt, and then the salt may be isolated and purified.

Specific examples of compound (I) of the present invention are shown in Table 1 to Table 21. However, the compounds of the present invention are not limited to them.

TABLE 1

| compound No. | $R^1$ | $R^2$ | $R^3$ |
|---|---|---|---|
| 1 | 2,4-dichlorophenyl | H | -CH2C(O)NHS(O)2CH3 |
| 2 | 2-chloro-4-methylphenyl | H | -CH2C(O)NHS(O)2CH3 |
| 3 | 2-chloro-4-methylphenyl | H | -CH2CH2C(O)OH |
| 4 | 2-chloro-4-methylphenyl | H | -CHF2 |

TABLE 1-continued

[Structure: R¹-NH, R² on pyridinone ring with C=O, N-R³, connected via carbonyl to piperidine bearing 4-fluorophenyl]

| compound No. | R¹ | R² | R³ |
|---|---|---|---|
| 5 | 2-Cl-4-CH₃-phenyl | H | -CH₂CN |
| 6 | 2-Cl-4-CH₃-phenyl | H | -(CH₂)₃-OCH₃ |
| 7 | 2-Cl-4-CH₃-phenyl | H | -CH₂-cyclopropyl |
| 8 | 2-Cl-4-CH₃-phenyl | H | -CH₂-cyclobutyl |

TABLE 2

Table 2 (continued from Table 1)

| compound No. | R¹ | R² | R³ |
|---|---|---|---|
| 9 | 2-Cl-4-CH₃-phenyl | H | -CH₂-(oxazole-2-yl)-4-CO₂CH₃ |
| 10 | 2-Cl-4-CH₃-phenyl | H | -CH₂-(3,5-dimethylisoxazol-4-yl) |
| 11 | 2-Cl-4-CH₃-phenyl | H | -(CH₂)₃-CH(OCH₃)₂ |
| 12 | 2-Cl-4-CH₃-phenyl | H | -CH₂-(5-oxo-4,5-dihydro-1,2,4-oxadiazol-3-yl) |

TABLE 2-continued

Table 2 (continued from Table 1)

| compound No. | R¹ | R² | R³ |
|---|---|---|---|
| 13 | 2-Cl-4-CH₃-phenyl | H | -CH₂-C(=N-OH)-NH₂ |
| 14 | 2-Cl-4-CH₃-phenyl | H | -CH₂-(5-tert-butyl-1,2,4-oxadiazol-3-yl) |
| 15 | 2-Cl-4-CH₃-phenyl | H | -CH₂-(5-methylisoxazol-3-yl) |
| 16 | 2-Cl-4-CH₃-phenyl | H | -CH₂-(5-thioxo-4,5-dihydro-1,3,4-oxadiazol-2-yl) |
| 17 | 2-Cl-4-CH₃-phenyl | H | -(CH₂)₂-morpholin-4-yl |
| 18 | 2-Cl-4-CH₃-phenyl | H | -CH₂-(4-methyl-4H-1,2,4-oxadiazol-3-yl) |

TABLE 3

Table 3 (continued from Table 1)

| compound No. | R¹ | R² | R³ |
|---|---|---|---|
| 19 | 2-Cl-4-CH₃-phenyl | H | -(CH₂)₃-CN |
| 20 | 2-Cl-4-CH₃-phenyl | H | -CH₂-C(=O)-(2-cyanopyrrolidin-1-yl) |
| 21 | 2-CH₃-4-Cl-phenyl | Cl | -CH₂-O-CH₂-phenyl |

TABLE 3-continued

Table 3 (continued from Table 1)

| compound No. | R¹ | R² | R³ |
|---|---|---|---|
| 22 | 2-Cl-4-CH₃-phenyl | H | -CH₂-(tetrahydropyran-4-yl) |
| 23 | 4-F-2-CH₃-phenyl | H | -CH₂-CN |
| 24 | 4-F-2-CH₃-phenyl | H | -CH₂-(5-oxo-4H-1,2,4-oxadiazol-3-yl) |
| 25 | 4-F-2-CH₃-phenyl | H | -CH₂-C(O)O-CH₃ |
| 26 | 4-F-2-CH₃-phenyl | H | -CH₂-C(O)OH |
| 27 | 4-F-2-CH₃-phenyl | H | -CH₂-(1-methyl-1H-imidazol-2-yl) |
| 28 | 4-F-2-CH₃-phenyl | H | -(CH₂)₃-CN |

TABLE 4

Table 4 (continued from Table 1)

| compound No. | R¹ | R² | R³ |
|---|---|---|---|
| 29 | 2-Cl-4-CH₃-phenyl | H | -CH₂-C(O)O-CH₃ |
| 30 | benzyl | H | -CH₂-(1-methyl-1H-imidazol-2-yl) |
| 31 | benzyl | H | -CH₂-CN |
| 32 | benzyl | H | -CH₂-C(O)O-C(CH₃)₃ |
| 33 | benzyl | H | -CH₂-(5-oxo-4H-1,2,4-oxadiazol-3-yl) |
| 34 | benzyl | H | -CH₂-C(O)OH |
| 35 | benzyl | H | -CH₂-C(O)NH-CN |
| 36 | 4-F-2-CH₃-phenyl | H | CH₃ |
| 37 | 4-Cl-2-CH₃-phenyl | H | CH₃ |
| 38 | 4-F-2-CH₃-phenyl | F | -CH₂-cyclopropyl |

TABLE 5

[Structure: pyridinone core with R¹-NH, Cl, C(=O)-piperidinyl-(4-fluorophenyl), N-R³]

| compound No. | R¹ | R³ |
|---|---|---|
| 39 | 4-F-2-CH₃-phenyl | CH₃ |
| 40 | 4-Cl-2-CH₃-phenyl | CH₃ |

TABLE 5-continued

Core structure: 3-chloro-4-(R¹NH)-1-(R³)-5-[4-(4-fluorophenyl)piperidine-1-carbonyl]pyridin-2(1H)-one

| compound No. | R¹ | R³ |
|---|---|---|
| 41 | 2-chloro-5-fluoro-4-methylphenyl | CH₃ |
| 42 | benzyl | CH₃ |
| 43 | 4-methoxy-2-methylphenyl | CH₃ |
| 44 | 4-methoxyphenyl | CH₃ |
| 45 | pyridin-4-yl | CH₃ |
| 46 | 3-methoxyphenyl | CH₃ |
| 47 | 2-methoxyphenyl | CH₃ |
| 48 | cyclopropyl | CH₃ |
| 49 | 4-(trifluoromethoxy)phenyl | CH₃ |
| 50 | 4-fluoro-2-methylphenyl | cyclopropyl |
| 51 | 2,5-dimethoxyphenyl | CH₃ |
| 52 | pyridin-3-yl | CH₃ |
| 53 | 4-chloro-2-methylphenyl | cyclopropyl |
| 54 | 2,4-difluorophenyl | CH₃ |

TABLE 6

Table 6 (continued from Table 5)

| compound No. | R¹ | R³ |
|---|---|---|
| 55 | 4-methoxyphenyl | cyclopropyl |
| 56 | 2-(trifluoromethoxy)phenyl | CH₃ |
| 57 | 4-chloro-2-methoxyphenyl | CH₃ |
| 58 | 2-chloro-4-methylphenyl | cyclopropyl |
| 59 | 2,4,5-trifluorophenyl | CH₃ |
| 60 | 2,5-dimethoxyphenyl | cyclopropyl |

TABLE 6-continued

Table 6 (continued from Table 5)

| compound No. | R¹ | R³ |
|---|---|---|
| 61 | 4-chloro-2,5-dimethoxyphenyl | CH₃ |
| 62 | 4-cyanophenyl | CH₃ |
| 63 | 2,4-dimethoxyphenyl | CH₃ |
| 64 | 3-chloro-4-cyanophenyl | CH₃ |
| 65 | 4-chlorobenzyl | CH₃ |
| 66 | 4-cyano-2-fluorophenyl | CH₃ |
| 67 | 2-chloro-4-cyanophenyl | CH₃ |
| 68 | 3,4-dimethoxyphenyl | CH₃ |
| 69 | 2-fluoro-4-methoxyphenyl | CH₃ |
| 70 | 2,4,5-trifluorophenyl | cyclopropyl |
| 71 | 2,4-difluorophenyl | cyclopropyl |
| 72 | 4-chloro-2-methylphenyl | cyclopropyl |
| 73 | 4-methoxy-2-methylphenyl | cyclopropyl |
| 74 | 4-chloro-2-methylphenyl | CH₃ |

TABLE 7

Table 7 (continued from Table 5)

| compound No. | R¹ | R³ |
|---|---|---|
| 75 | 4-fluoro-3-methylphenyl | CH₃ |
| 76 | 2,4-dimethylphenyl | CH₃ |
| 77 | 4-(difluoromethoxy)phenyl | CH₃ |
| 78 | 4-isopropoxyphenyl | CH₃ |
| 79 | 4-ethoxyphenyl | CH₃ |
| 80 | 2,4-dimethylphenyl | CH₃ |
| 81 | cyclohexyl | CH₃ |
| 82 | 2,5-difluorophenyl | CH₃ |
| 83 | 4-methoxy-2-methylphenyl | CH₃ |

TABLE 7-continued

Table 7 (continued from Table 5)

| compound No. | R¹ | R³ |
|---|---|---|
| 84 | 4-chloro-3-methoxyphenyl | cyclopropylmethyl |
| 85 | 4-fluoro-2-methylphenyl | cyclopropylmethyl |
| 86 | 3,4-difluorophenyl | CH₃ |
| 87 | 3,4-dimethylphenyl | CH₃ |
| 88 | 4-chloro-3-methoxyphenyl | CH₃ |
| 89 | 4-fluoro-3-methoxyphenyl | CH₃ |
| 90 | 2,3-difluorophenyl | CH₃ |
| 91 | 4-(methylthio)phenyl | CH₃ |
| 92 | 3-fluoro-4-methoxyphenyl | CH₃ |

TABLE 8

$$\text{[Structure: R}^1\text{NH-substituted pyridinone with 4-(4-fluorophenyl)piperidine carbonyl]}$$

| compound No. | R¹ | R² | R³ |
|---|---|---|---|
| 93 | 4-methoxy-3-methylphenyl | Cl | CH₃ |
| 94 | 4-fluoro-2-methylphenyl | Br | cyclopropylmethyl |
| 95 | 3-cyanophenyl | Cl | CH₃ |
| 96 | 3,4-dicyanophenyl | Cl | CH₃ |
| 97 | 4-cyano-2,5-difluorophenyl | Cl | CH₃ |
| 98 | 3-cyano-4-methylphenyl | Cl | CH₃ |
| 99 | 2-cyanophenyl | Cl | CH₃ |
| 100 | 4-cyano-2-methylphenyl | Cl | CH₃ |
| 101 | 4-cyano-2-ethylphenyl | Cl | CH₃ |
| 102 | 3-fluoro-4-methylphenyl | Cl | CH₃ |

TABLE 8-continued

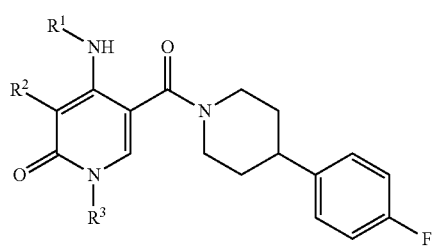

| compound No. | R¹ | R² | R³ |
|---|---|---|---|
| 103 | 2,4-dicyanophenyl | Cl | CH₃ |
| 104 | 4-methyl-2-cyanophenyl | Cl | CH₃ |
| 105 | 2,3-dimethylphenyl | Cl | CH₃ |
| 106 | 2,2-difluoro-1,3-benzodioxol-5-yl | Cl | CH₃ |

TABLE 9

Table 9 (continued from Table 8)

| compound No. | R¹ | R² | R³ |
|---|---|---|---|
| 107 | 2,3-dihydro-1H-inden-5-yl | Cl | CH₃ |
| 108 | 4-ethylphenyl | Cl | CH₃ |
| 109 | 2-fluoro-4-cyanophenyl | Cl | CH₃ |
| 110 | 2,6-difluoro-4-cyanophenyl | Cl | CH₃ |
| 111 | 3-chloro-4-(methylthio)phenyl | Cl | CH₃ |
| 112 | 2-(trifluoromethyl)-4-cyanophenyl | Cl | CH₃ |
| 113 | 3-(trifluoromethyl)-4-(methylthio)phenyl | Cl | CH₃ |
| 114 | 4-(trifluoromethyl)phenyl | Cl | CH₃ |
| 115 | 4-isopropylphenyl | Cl | CH₃ |
| 116 | 4-chloro-2-cyanophenyl | Cl | CH₃ |
| 117 | 4-chloro-3-cyanophenyl | Cl | CH₃ |
| 118 | 4-fluoro-3-methylphenyl | Cl | CH₃ |
| 119 | 4-fluoro-3-chlorophenyl | Cl | CH₃ |
| 120 | 4-fluoro-2-methylphenyl | CH₃ | CH₃ |
| 121 | 4-chloro-2-methylphenyl | CH₃ | CH₃ |

TABLE 9-continued

Table 9 (continued from Table 8)

| compound No. | R¹ | R² | R³ |
|---|---|---|---|
| 122 | 4-(methylsulfonyl)-3-(trifluoromethyl)phenyl | Cl | CH₃ |
| 123 | 3-chloro-4-(methylsulfonyl)phenyl | Cl | CH₃ |
| 124 | 4-cyano-2-methylphenyl | CH₃ | CH₃ |

TABLE 10

Table 10 (continued from Table 8)

| compound No. | R¹ | R² | R³ |
|---|---|---|---|
| 125 | 2,4-difluorophenyl | CH₃ | CH₃ |
| 126 | 4-fluoro-2-methylphenyl | Cl | CH₃ |
| 127 | 2-chloro-4-fluorophenyl | Cl | CH₃ |
| 128 | 2-fluoro-4-(methylthio)phenyl | Cl | CH₃ |
| 129 | 4-cyano-2-methylphenyl | Cl | CH₃ |
| 130 | 4-chloro-2-fluorophenyl | Cl | CH₃ |
| 131 | 2-cyano-4-fluorophenyl | Cl | CH₃ |
| 132 | 2-cyano-4-methylphenyl | Cl | CH₃ |

TABLE 10-continued

Table 10 (continued from Table 8)

| compound No. | R¹ | R² | R³ |
|---|---|---|---|
| 133 | 2-cyano-4-(methylthio)phenyl | Cl | CH₃ |
| 134 | 4-cyano-2-(difluoromethoxy)phenyl | Cl | CH₃ |

TABLE 11

Table 11 (continued from Table 8)

| compound No. | R¹ | R² | R³ |
|---|---|---|---|
| 135 | 4-fluoro-2-methylphenyl | Cl | CH₂CH₃ |
| 136 | 4-chloro-2-methylphenyl | Cl | CH₂CH₃ |
| 137 | 5-chloro-2-methylphenyl | Cl | CH₂CH₃ |
| 138 | 4-methoxy-2-methylphenyl | Cl | CH₂CH₃ |
| 139 | 2,4-difluorophenyl | Cl | CH₂CH₃ |
| 140 | 4-fluoro-2-methylphenyl | Cl | CH₂CH₂OCH₃ |
| 141 | 4-chloro-2-methylphenyl | Cl | CH₂CH₂OCH₃ |
| 142 | 5-chloro-2-methylphenyl | Cl | CH₂CH₂OCH₃ |
| 143 | 4-methoxy-2-methylphenyl | Cl | CH₂CH₂OCH₃ |

TABLE 11-continued

Table 11 (continued from Table 8)

| compound No. | R¹ | R² | R³ |
|---|---|---|---|
| 144 | 2,4-difluorophenyl | Cl | -CH₂CH₂-O-CH₃ |

TABLE 12

Table 12 (continued from Table 8)

| compound No. | R¹ | R² | R³ |
|---|---|---|---|
| 145 | 4-(methylsulfonyl)-2-fluorophenyl | Cl | CH₃ |
| 146 | 2-(methylsulfonyl)-phenyl (with CN) | Cl | CH₃ |
| 147 | 2-chloro-phenyl (with CN) | Cl | CH₃ |
| 148 | 4-fluoro-3-cyano-phenyl | Cl | CH₃ |
| 149 | 4-trifluoromethyl-2-cyano-phenyl | Cl | CH₃ |
| 150 | 4-fluoro-2-cyano-phenyl | Cl | CH₃ |
| 151 | 4-fluoro-2-methyl-phenyl | Cl | 3-pyridylmethyl |
| 152 | 4-chloro-2-methyl-phenyl | Cl | 3-pyridylmethyl |
| 153 | 4-chloro-2-methyl-phenyl | Cl | 3-pyridylmethyl |

TABLE 12-continued

Table 12 (continued from Table 8)

| compound No. | R¹ | R² | R³ |
|---|---|---|---|
| 154 | 4-methoxy-2-methyl-phenyl | Cl | 3-pyridylmethyl |

TABLE 13

Table 13 (continued from Table 8)

| compound No. | R¹ | R² | R³ |
|---|---|---|---|
| 155 | 2,4-difluorophenyl | Cl | 3-pyridylmethyl |
| 156 | 4-trifluoromethoxy-2-cyano-phenyl | Cl | CH₃ |
| 157 | 6-methyl-pyridin-3-yl | Cl | CH₃ |
| 158 | 4-fluoro-2-methyl-phenyl | Cl | -CH₂CH₂CH₂F |
| 159 | 4-chloro-2-methyl-phenyl | Cl | -CH₂CH₂CH₂F |
| 160 | 4-chloro-2-methyl-phenyl | Cl | -CH₂CH₂CH₂F |
| 161 | 4-methoxy-2-methyl-phenyl | Cl | -CH₂CH₂CH₂F |
| 162 | 2,4-difluorophenyl | Cl | -CH₂CH₂CH₂F |
| 163 | 4-chloro-2-methyl-phenyl | Cl | 2-pyridylmethyl |

TABLE 13-continued

Table 13 (continued from Table 8)

| compound No. | R¹ | R² | R³ |
|---|---|---|---|
| 164 | 2-fluoro-4-substituted benzonitrile | Cl | CH₃ |

TABLE 14

Table 14 (continued from Table 8)

| compound No. | R¹ | R² | R³ |
|---|---|---|---|
| 165 | 4-CF₃, 2-CN phenyl | Cl | CH₃ |
| 166 | 4-chloro-2-methylphenyl | Cl | but-2-enyl (CH₂CH=CHH) |
| 167 | 4-chloro-2-methylphenyl | Cl | propargyl (CH₂C≡CH) |
| 168 | 4-chloro-2-methylphenyl | Cl | CH₂CN |
| 169 | 4-chloro-2-methylphenyl | Cl | (5-oxo-4,5-dihydro-1,2,4-oxadiazol-3-yl)methyl |
| 170 | 4-chloro-2-methylphenyl | Cl | (2H-tetrazol-5-yl)methyl |
| 171 | 2-methyl-1,3-dioxoisoindolin-5-yl | Cl | CH₃ |
| 172 | 2,4-difluorophenyl | Cl | pyridin-2-ylmethyl |
| 173 | benzo[d]thiazol-6-yl | Cl | CH₃ |

TABLE 14-continued

Table 14 (continued from Table 8)

| compound No. | R¹ | R² | R³ |
|---|---|---|---|
| 174 | benzo[c][1,2,5]oxadiazol-4-yl | Cl | CH₃ |

TABLE 15

Table 15 (continued from Table 8)

| compound No. | R¹ | R² | R³ |
|---|---|---|---|
| 175 | 1-methyl-1H-indazol-6-yl | Cl | CH₃ |
| 176 | 2,2-dimethyl-2,3-dihydrobenzofuran-7-yl | Cl | CH₃ |
| 177 | 1H-benzo[d][1,2,3]triazol-5-yl | Cl | CH₃ |
| 178 | 2-chloro-4-substituted benzonitrile | CH₃ | CH₃ |
| 179 | benzo[d][1,3]dioxol-5-yl | Cl | CH₃ |
| 180 | 3,4-dihydro-2H-benzo[b][1,4]dioxepin-7-yl | Cl | CH₃ |
| 181 | 2,3-dihydrobenzo[b][1,4]dioxin-6-yl | Cl | CH₃ |
| 182 | 2,4-difluorophenyl | Cl | 2-morpholinoethyl |

TABLE 15-continued

Table 15 (continued from Table 8)

| compound No. | R¹ | R² | R³ |
|---|---|---|---|
| 183 | 2,4-difluorophenyl | Cl | —CH₂CH₂OH |
| 184 | 2,4,5-trifluorophenyl | Cl | 5-methyl-1,3,4-oxadiazol-2-ylmethyl |

TABLE 16

Table 16 (continued from Table 8)

| compound No. | R¹ | R² | R³ |
|---|---|---|---|
| 185 | 5-chloro-2-methylphenyl | Cl | 2-morpholinoethyl |
| 186 | 5-chloro-2-methylphenyl | Cl | —CH₂CH₂OH |
| 187 | 5-chloro-2-methylphenyl | Cl | 5-methyl-1,3,4-oxadiazol-2-ylmethyl |
| 188 | 1,1-dioxo-benzo[b]thiophen-6-yl | Cl | CH₃ |
| 189 | 5-chloro-2-methylphenyl | Cl | n-butyl |
| 190 | 5-chloro-2-methylphenyl | Cl | —CH₂CH₂CF₃ |
| 191 | 3-fluoro-4-methoxyphenyl | CH₃ | CH₃ |
| 192 | 2,4,5-trifluorophenyl | CH₃ | CH₃ |
| 193 | 4-chloro-2-fluorophenyl | CH₃ | CH₃ |
| 194 | 4-fluoro-2-methylphenyl | Cl | —OCH₃ |

TABLE 17

$$\text{(pyridinone core with R}^1\text{NH, R}^2, \text{R}^3, \text{R}^{44}\text{)}$$

| compound No. | R¹ | R² | R³ | R⁴⁴ |
|---|---|---|---|---|
| 195 | benzothiazol-6-yl | O₂N— | CH₃ | 4-(4-fluorophenyl)piperidin-1-yl |
| 196 | benzoxazol-5-yl | Cl— | CH₃ | 4-(4-fluorophenyl)piperidin-1-yl |

US 9,643,952 B2
TABLE 17-continued
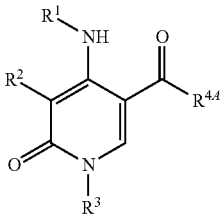
| compound No. | R¹ | R² | R³ | R⁴·⁴ |
|---|---|---|---|---|
| 197 | 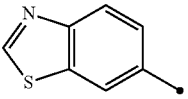 |  |  | 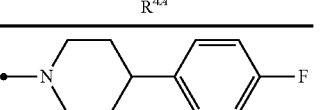 |
| 198 | 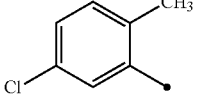 |  | 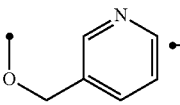 | 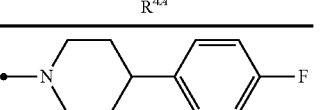 |
| 199 | 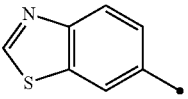 | 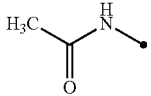 |  | 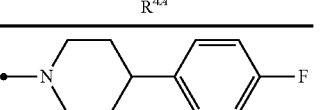 |
| 200 | 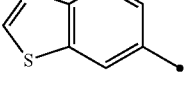 | 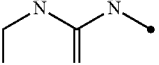 |  | 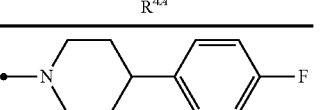 |
| 201 | 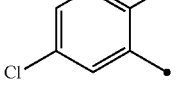 |  |  | 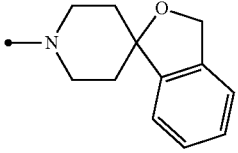 |
| 202 | 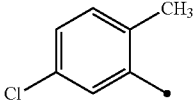 |  |  | 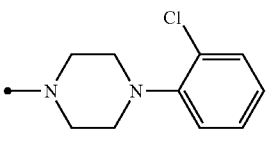 |
| 203 | 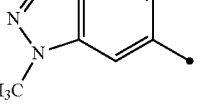 |  |  | 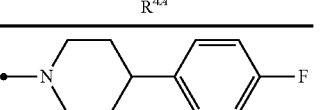 |
TABLE 18
Table 18 (continued from Table 17)
| compoud No. | R¹ | R² | R³ | R⁴·⁴ |
|---|---|---|---|---|
| 204 | 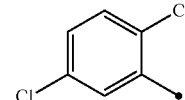 |  | 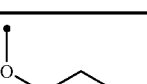 | 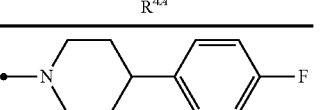 |
| 205 | 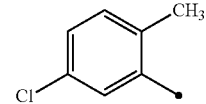 |  | 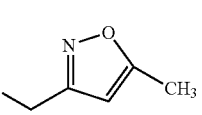 | 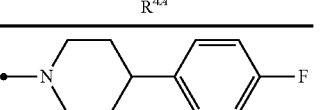 |

TABLE 18-continued

Table 18 (continued from Table 17)

| compound No. | R¹ | R² | R³ | R⁴⁴ |
|---|---|---|---|---|
| 206 | benzothiazol-5-yl | Cl– | –CH₂CH₂OCH₃ | 4-(4-fluorophenyl)piperidin-1-yl |
| 207 | 2,3-dihydro-1-benzofuran-5-yl | H₃C– | –CH₂-(pyridin-3-yl) | 4-(4-fluorophenyl)piperidin-1-yl |
| 208 | benzothiazol-5-yl | H₃C– | –CH₃ | 4-(4-fluorophenyl)piperidin-1-yl |
| 209 | 2,4-dimethylpyridin-5-yl | Cl– | –CH₃ | 4-(4-fluorophenyl)piperidin-1-yl |
| 210 | 2,6-dimethylpyridin-3-yl | Cl– | –CH=CH₂ | 4-(4-fluorophenyl)piperidin-1-yl |
| 211 | 2,3-dihydro-1-benzofuran-5-yl | H₃C– | cyclobutyl | 4-(4-fluorophenyl)piperidin-1-yl |
| 212 | 1-methyl-1H-benzimidazol-5-yl | H₃C– | cyclopentyl | 4-(4-fluorophenyl)piperidin-1-yl |
| 213 | 4-chloro-2-methylphenyl | Cl– | –OCH₂-cyclopropyl | 4-(4-fluorophenyl)piperidin-1-yl |

TABLE 19

Table 19 (continued from Table 17)

| compound No. | R¹ | R² | R³ | R⁴⁴ |
|---|---|---|---|---|
| 214 | 2,4-dimethylphenyl | Cl– | cyclopentyl | 4-(4-fluorophenyl)piperidin-1-yl |
| 215 | 1,3-dihydro-2-benzofuran-5-yl | Cl– | cyclopropyl | 4-(4-fluorophenyl)piperidin-1-yl |
| 216 | benzyl | O₂N– | –CH₃ | 4-(4-fluorophenyl)piperidin-1-yl |

TABLE 19-continued

Table 19 (continued from Table 17)

| compound No. | R¹ | R² | R³ | R⁴⁴ |
|---|---|---|---|---|
| 217 | 4-chloro-2-methylphenyl | Cl– | –N(CH₃)₂ | –N(piperidine)-C₆H₄-F |
| 218 | benzyl | H₂N– | –CH₃ | –N(piperidine)-C₆H₄-F |
| 219 | phenyl | H₂N– | –CH₃ | –N(piperidine)-C₆H₄-F |
| 220 | benzyl | Cl– | –OCH₃ | –N(piperidine)-C₆H₄-F |
| 221 | benzyl | NC– | –CH₃ | –N(piperidine)-C₆H₄-F |
| 222 | 2-methylphenyl | O₂N– | –CH₃ | –N(piperidine)-C₆H₄-F |
| 223 | 4-chloro-2-methylphenyl | Cl– | –OCH₂CH(OH)CH₃ | –N(piperidine)-C₆H₄-F |

TABLE 20

Table 20 (continued from Table 17)

| compoud No. | R¹ | R² | R³ | R⁴⁴ |
|---|---|---|---|---|
| 224 | 1-methyl-1H-indazol-6-yl | F– | –CH₃ | –N(piperidine)-C₆H₄-F |
| 225 | benzothiazol-6-yl | F– | –CH₃ | –N(piperidine)-C₆H₄-F |
| 226 | 4-chloro-2-methylphenyl | Cl– | –OCH₂-(tetrahydrofuran-2-yl) | –N(piperidine)-C₆H₄-F |
| 227 | 6-methylpyridin-3-yl | H₃C– | –OCH₂CH₂OH | –N(piperidine)-C₆H₄-F |

TABLE 20-continued
Table 20 (continued from Table 17)
| compoud No. | R¹ | R² | R³ | R⁴⁴ |
|---|---|---|---|---|
| 228 | 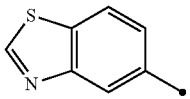 |  | 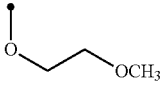 | 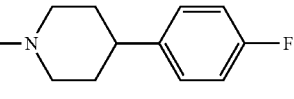 |
| 229 | 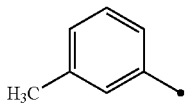 |  | 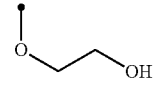 | 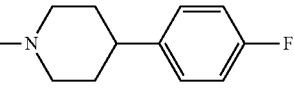 |
| 230 | 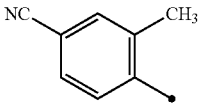 |  | 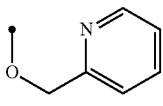 | 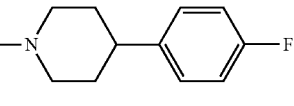 |
| 231 | 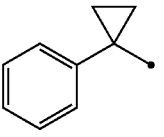 |  | 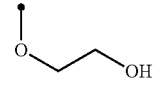 | 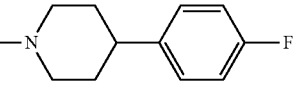 |
| 232 | 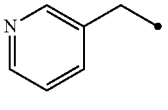 |  | 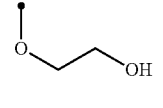 | 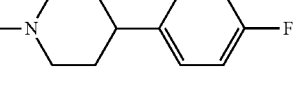 |
| 233 | 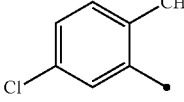 |  | 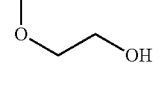 | 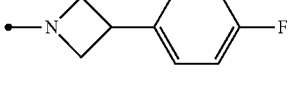 |
TABLE 21
Table 21 (continued from Table 17)
| compoud No. | R¹ | R² | R³ | R⁴⁴ |
|---|---|---|---|---|
| 234 | 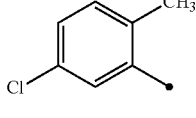 |  | 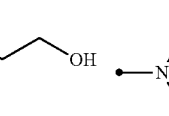 | 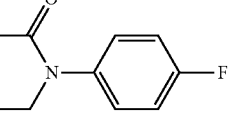 |
| 235 | 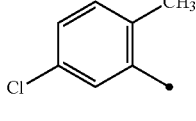 |  | 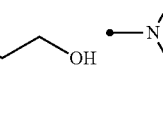 | 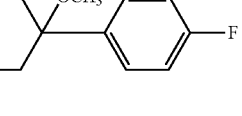 |
| 236 | 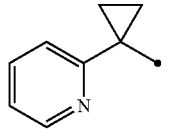 |  | 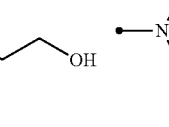 | 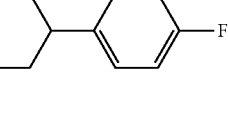 |

Next, pharmacological effects of a representative compound (I) are specifically explained by Experimental Examples.

Experimental Example 1

CCR10 Antagonistic Effect (1) Preparation of Human CCR10-Inducible Expression Plasmid A CCR10-inducible expression plasmid was prepared according to a known method [Analytical Biochemistry, 2006, vol. 400, page 163]. A DNA encoding human CCR10 was obtained by PCR. Using human chromosome DNA (100 ng; manufactured by Clontech) as a template, synthetic DNA having the sequences depicted in SEQ ID NOs: 1 and 2 as a human CCR10 cDNA specific primer, and Pyrobest DNA Polymerase (manufactured by TAKARA SHUZO CO. LTD.) as an enzyme, a DNA encoding human CCR10 was obtained by PCR. As a buffer for PCR, the buffer attached to the enzyme to be used, which was diluted 10-fold with deionized water, was used. Using Thermal Cycler DNA Engine (manufactured by MJ Research), PCR was performed by 35 cycles of reactions composed of an incubation at 94° C. for 30 sec, at an anneal temperature of 58° C. for 30 sec, and at 72° C. for 1 min after treating at 90° C. for 2 min.

The amplified PCR fragment was cleaved with HindIII and NotI, then a human CCR10 DNA fragment was recovered by the agarose gel electrophoresis method. The fragment was incorporated between the corresponding restriction enzyme sites (HindIII-NotI) of an inducible expression vector to construct a human CCR10-inducible expression plasmid.

Using a primer specific to the sequence of plasmid (synthetic DNA having the sequences shown in SEQ ID NOs: 3 and 4), the sequence of human CCR10 DNA region was determined. For the determination of the base sequence, DNA Sequencer 377 (manufactured by Perkin Elmer. Co.) and a reaction kit (ABI Prism (registered trade mark) Big-Dye (registered trade mark) Terminator Cycle Sequencing Ready Reaction kit: manufactured by Applied Biosystems) were used. The sequence of human CCR10 DNA was identical with the sequence (NM 016602) registered in GenBank.

(2) Preparation of Human CCR10 Expressing Cell for Calcium Assay

Cells for detecting signals from human CCR10 in calcium assay were prepared. According to a known method [Analytical-Biochemistry (Analy Biochem), 2006, vol. 400, page 163], human CCR10-inducible expressing cells whose host cell is KJMGER8 cell (Namalwa cell-derived cell line) were prepared. Human CCR10-inducible expression plasmid produced above and Ga16 expression plasmid were co-transfected into the KJMGER8 cells by the electroporation method [Cytotechnology, 1990, vol. 3, page 133], whereby the signals from human CCR10 could be detected by calcium assay (hereinafter to be referred to as hCCR10G16 cell). A Ga16 expression plasmid was produced by incorporating human Galli DNA into expression vector pAMoh (WO 03/087366). Expression of human CCR10 was induced by cultivating hCCR10G16 cells in the presence of 10 nmol/L β-estradiol (manufactured by Sigma Ltd.) for 24 hr.

(3) Calcium Assay of Human CCR10

Cells expressing human CCR10 induced by the above-mentioned method were suspended in RPMI1640 medium (manufactured by Invitrogen), and adjusted to a cell density of $2\times10^6$ cells/mL. The cells were blended with an equivalent volume of a loading buffer prepared according to the attached protocol of Fluo-3 calcium assay kit (manufactured by Molecular Devices Corporation), and incubated at 37° C. for several dozen minutes. This mixture was dispensed to a 384 well clear-bottom plate (manufactured by Corning Incorporated) at 40 µL/well. To this plate was added a solution of the test compound in dimethyl sulfoxide (DMSO), which was diluted 37-fold with RPMI1640 medium, at 5 µL/well, and the mixture was incubated at 37° C. for 30 min. 300 nmol/L human recombinant CTACK (manufactured by R&D Systems, Inc.) diluted with RPMI1640 medium containing 1 w/v % bovine serum albumin (manufactured by Sigma Ltd.) was added at 5 µL/well and, variation of intracellular calcium ion concentration for about 5 min after the addition was measured by a screening apparatus (FDSS; manufactured by Hamamatsu Photonics K.K.). The difference between the maximum fluorescence intensity and the minimum fluorescence intensity measured in the 5 minutes was calculated and taken as the measured value (maximum fluorescence intensity−minimum fluorescence intensity).

The inhibition rate of the test compound against increase of calcium ion concentration was calculated by the following formula.

$$\text{inhibition rate against increase of calcium ion concentration (\%)} = \left(1 - \frac{\text{test compound addition group} - \text{blank}}{\text{control} - \text{blank}}\right) \times 100$$

test compound addition group: average measurement value of variation of intracellular calcium ion concentration of the test compound addition group control: average measurement value as measured by adding, instead of a solution of the test compound, DMSO 37-fold diluted with RPMI1640 medium, adding 300 nmol/L CTACK diluted with RPMI1640 medium containing 1 w/v % bovine serum albumin, and measuring variation of intracellular calcium ion concentration blank: average measurement value as measured by adding, instead of a solution of the test compound, DMSO 37-fold diluted with RPMI1640 medium, adding, instead of a medium containing CTACK, RPMI1640 medium containing 1 w/v % bovine serum albumin, and measuring variation of intracellular calcium ion concentration A concentration-reaction curve was drawn from the inhibition rate against increase of calcium ion concentration when treated with not less than 5 concentrations of the test compound at 3- to 10-fold common ratio, and $IC_{50}$ value was calculated.

Compounds 1-3, 5-33, 35-44, 46, 47, 49-51, 53-55, 57-133, 135-145, 147-236 inhibited an increase in the calcium ion concentration by not less than 50% at a concentration of not more than 1000 nmol/L. Compound (I) or a pharmaceutically acceptable salt thereof was considered to have a CCR10 antagonistic action, and to be useful as a prophylactic and/or therapeutic agent for the diseases involving CCR10.

Therefore, compound (I) or a pharmaceutically acceptable salt thereof was considered to be useful as a prophylactic and/or therapeutic agent for the diseases involving CCR10, for example, skin diseases [for example, acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies, linear dermatitis and the like] and the like.

Experimental Example 2

Suppressive Action on Dinitrofluorobenzene-Induced Auricle Edema Reaction in Mouse BALE/c mice (female, supplied by CHARLES RIVER LABORATORIES JAPAN, INC.) were purchased at the age of 5 weeks. After quarantine and acclimation, mice showing smooth body weight increase and free of abnormality in appearance were used and the test was started at the age of 7 weeks. The mice were housed in a breeding room at room temperature 19-25° C., humidity 30-70%, 12 hr lighting per day (7 a.m.-7 p.m.) with 3 mice in each plastic gauge, and bred on with free ingestion of a commercially available solid feed and water.

Two days before the test, the abdomen of the BALE/c mice was shaved, and the mice were immunized by applying 100 µL of a solution {concentration 0.5% [weight (w)/volume (v) %]} of dinitrofluorobenzene (manufactured by Nacalai Tesque) in acetone (manufactured by Wako Pure Chemical Industries, Ltd.) to the shaved part. The reaction was induced by applying dinitrofluorobenzene-acetone solution [concentration 0.2% (w/v %)] to the front and the back of auricle (10 µL to each, total 20 µL) on day 5 after the immunization. A test compound dissolved in acetone at concentration of 1% (w/v %) was administered by applying same to the front and the back of auricle (10 µL to each, total 20 µL) 1 hr before and 3 hr after induction of the reaction. After application, the applied part was air-dried with a dryer.

The group applying administered with the test compound was taken as a test compound administration group, and the group applying administered with acetone as a solvent instead of the test compound was taken as a solvent administration group. Also, the group free of immunization and reaction induction but applying administered with acetone instead of the test compound was taken as a normal group. The thickness of auricle was measured using a dial thickness gauge (G-1A manufactured by OZAKI MFG. CO., LTD.) immediately before and 24 hr after induction of the reaction, and the difference thereof was taken as auricle edema. The suppression rate (%) of auricle edema was calculated according to the following formula. The results are shown in Table 22.

$$\text{auricle edema suppression rate (\%)} = \frac{\text{value of solvent administration group} - \text{value of test compound administration group}}{\text{value of solvent administration group} - \text{value of normal group}} \times 100$$

TABLE 22

| compound No. | auricle edema suppression rate (%) |
|---|---|
| 100 | 53 |
| 125 | 47 |
| 144 | 32 |
| 204 | 41 |
| 206 | 30 |

Compounds 100, 125, 145, 204 and 206 showed a suppressive action on auricle edema response, and compound (I) or a pharmaceutically acceptable salt thereof was considered to be useful as a prophylactic and/or therapeutic agent for contact dermatitis or atopic dermatitis.

While compound (I) or a pharmaceutically acceptable salt thereof used in the present invention can be directly administered singly, it is generally desirable to provide as various pharmaceutical preparations. Also, such pharmaceutical preparations are used for animals or human.

The pharmaceutical preparation of the present invention can contain, as an active ingredient, compound (I) or a pharmaceutically acceptable salt thereof singly or in a mixture with any other active ingredient for the treatment. Also, such pharmaceutical preparation is produced by any method known in the technical field of formulation study, by mixing the active ingredient with one or more kinds of pharmaceutically acceptable carriers (for example, diluent, solvent, excipient and the like).

As the administration route, it is desirable to use a route the most effective for the treatment and, for oral, or, parenteral routes such as intravenous, external or the like can be mentioned.

Examples of the administration form include tablet, injection, ointment or the like.

For example, tablet and the like suitable for oral administration can be produced using excipient such as lactose and the like, disintegrant such as starch and the like, lubricant such as magnesium stearate and the like, binder such as hydroxypropylcellulose and the like, and the like.

For example, injection and the like suitable for intravenous administration can be produced using diluent or solvent such as salt solution, glucose solution or a mixture of salt water and glucose solution and the like, and the like.

For example, ointment suitable for external preparation can be produced using a base material such as petrolatum and the like, and an additive such as stearyl alcohol and the like.

While the dose and administration frequency of compound (I) or a pharmaceutically acceptable salt thereof used in the present invention vary depending on the administration form, age and body weight of patients, nature or severity of the symptoms to be treated, and the like, it is generally 0.01-1000 mg, preferably 0.05-100 mg, by oral administration to an adult, which is administered in one to several portions per day. For intravenous administration, external use and the like, 0.001-1000 mg, preferably 0.01-100 mg, is administered to an adult in one to several portions per day. However, such dose and administration frequency vary depending on the aforementioned various conditions.

The present invention is explained in more detail in the following by referring to Examples and Reference Examples. The scope of the present invention is not limited by these Examples and Reference Examples.

The proton nuclear magnetic resonance spectrum ($^1$H NMR) used in the Examples were measured at 270 MHz, 300 MHz or 400 MHz, and exchanging proton may not be observed clearly depending on the compound and measurement conditions. The indication of the multiplicity of the signals is conventional, where br means an apparently broad signal. For nomenclature of each synthesized compound, ChemBioDraw Ultra version 11.0.1 was used where necessary.

Example 1

3-{4-(2-chloro-5-methylphenylamino)-5-[4-(4-fluorophenyl)piperidine-1-carbonyl]-2-oxopyridin-1(2H)-yl}propionic acid (compound 3)

(step 1) Methyl 4,6-dichloronicotinate (8.0 g, 39 mmol) was dissolved in ethanol (150 mL), 2-chloro-5-methylaniline (6.05 g, 42.7 mmol) and concentrated hydrochloric acid (0.12 mL, 3.88 mmol) were added, and the mixture was stirred with heating under reflux for 16 hr. The reaction mixture was cooled to room temperature, and the precipitated solid was collected by filtration to give methyl 6-chloro-4-(2-chloro-5-methylphenylamino)nicotinate (3.68 g, 31%).

ESIMS m/z: 311 (M+H)$^+$; $^1$H NMR (300 MHz, CDCl$_3$, δ): 2.36 (s, 3H), 3.95 (s, 3H), 6.76 (s, 1H), 7.03-7.06 (m, 1H), 7.21-7.22 (m, 1H), 7.38-7.40 (m, 1H), 8.80 (s, 1H), 9.83 (br s, 1H).

(step 2) Methyl 6-chloro-4-(2-chloro-5-methylphenylamino)nicotinate (3.69 g, 11.8 mmol) obtained in step 1 was dissolved in acetic acid (139 mL) and water (46 mL), and the mixture was stirred with heating under reflux for 3 days. The reaction mixture was cooled to room temperature, and the precipitated solid was collected by filtration to give methyl 4-(2-chloro-5-methylphenylamino)-6-oxo-1,6-dihydropyridine-3-carboxylate (1.14 g, 33%).

ESIMS m/z: 293 (M+H)$^+$; $^1$H NMR (300 MHz, CDCl$_3$, δ): 2.34 (s, 3H), 3.90 (s, 3H), 5.83 (s, 1H), 6.96-7.00 (m, 1H), 7.27-7.28 (m, 1H), 7.34-7.37 (m, 1H), 8.17 (s, 1H), 9.60 (br s, 1H).

(step 3) Methyl 4-(2-chloro-5-methylphenylamino)-6-oxo-1,6-dihydropyridine-3-carboxylate (0.42 g, 1.50 mmol) obtained in step 2 was dissolved in 10 mol/L aqueous potassium hydroxide solution (6.0 mL), and the mixture was stirred with heating under reflux for 1 hr. The reaction mixture was cooled to room temperature, concentrated hydrochloric acid was added to pH=1, and the precipitated solid was collected by filtration to give 4-(2-chloro-5-methylphenylamino)-6-oxo-1,6-dihydropyridine-3-carboxylic acid (0.42 g, quantitative).

ESIMS m/z: 279 (M+H)$^+$; $^1$H NMR (400 MHz, DMSO-d$_6$, δ): 2.33 (s, 3H), 5.41 (s, 1H), 7.06-7.08 (m, 1H), 7.37 (s, 1H), 7.45-7.47 (m, 1H), 8.07 (s, 1H), 9.60 (br s, 1H), 11.45 (br s, 1H).

(step 4) 4-(2-Chloro-5-methylphenylamino)-6-oxo-1,6-dihydropyridine-3-carboxylic acid (1.12 g, 4.02 mmol) obtained in step 3 was dissolved in DMF (20 mL), HATU (3.06 g, 8.04 mmol), 4-(4-fluorophenyl)piperidine hydrochloride (1.73 g, 8.04 mmol) and N,N-diisopropylamine (3.42 mL, 20.1 mmol) were added, and the mixture was stirred at room temperature for 3 hr. To the reaction mixture was added 5% aqueous citric acid solution, and the mixture was extracted with ethyl acetate. The organic layer was washed with water, and dried over anhydrous magnesium sulfate. The solvent was evaporated under reduced pressure. The residue was purified by silica gel column chromatography (hexane/ethyl acetate=100/0-20/70) to give 4-(2-chloro-5-methylphenylamino)-5-[4-(4-fluorophenyl)piperidine-1-carbonyl]pyridin-2(1H)-one (1.63 g, 92%).

ESIMS m/z: 440 (M+H)$^+$; $^1$H NMR (300 MHz, CDCl$_3$, δ): 1.60-1.71 (m, 2H), 1.93-2.08 (m, 2H), 2.32 (s, 3H), 2.77-2.86 (m, 1H), 3.04-3.13 (m, 2H), 4.46-4.49 (m, 2H), 6.07 (s, 1H), 6.90-6.92 (m, 1H), 6.99-7.03 (m, 3H), 7.14-7.17 (m, 2H), 7.28-7.38 (m, 2H), 8.37 (s, 1H).

(step 5) 4-(2-Chloro-5-methylphenylamino)-5-[4-(4-fluorophenyl)piperidine-1-carbonyl]pyridin-2(1H)-one (80 mg, 0.182 mmol) obtained in step 4 was dissolved in DMF (1.5 mL), potassium carbonate (75 mg, 0.546 mmol) and methyl acrylate (0.049 mL, 0.546 mmol) were added, and the mixture was stirred at 80° C. for 1 hr. To the reaction mixture was added 10% aqueous citric acid solution (5 mL), and the precipitated solid was collected by filtration to give methyl 3-{4-(2-chloro-5-methylphenylamino)-5-[4-(4-fluorophenyl)piperidine-1-carbonyl]-2-oxopyridin-1(2H)-yl}propionate (82 mg, 86%).

ESIMS m/z: 526 (M+H)$^+$; $^1$H NMR (270 MHz, DMSO-d$_6$, δ): 1.63-1.73 (m, 2H), 1.81-1.85 (m, 2H), 2.31 (s, 3H), 2.75 (t, J=6.9 Hz, 2H), 2.81-2.94 (m, 1H), 3.01-3.11 (m, 2H), 3.58 (s, 3H), 4.03 (t, J=6.9 Hz, 2H), 4.26-4.30 (m, 2H), 5.40 (s, 1H), 7.03-7.16 (m, 3H), 7.26-7.36 (m, 3H), 7.44 (d, J=7.9 Hz, 1H), 7.78 (s, 1H), 8.26 (s, 1H).

(step 6) Methyl 3-{4-(2-chloro-5-methylphenylamino)-5-[4-(4-fluorophenyl)piperidine-1-carbonyl]-2-oxopyridin-1(2H)-yl}propionate (80 mg, 0.152 mmol) obtained in step 5 was dissolved in methanol (3 mL), 1 mol/L aqueous sodium hydroxide solution (2 mL) was added, and the mixture was stirred at room temperature for 1 hr. The solvent of the reaction mixture was evaporated under reduced pressure. To the residue were added water (1 mL) and 2 mol/L hydrochloric acid (1.5 mL), and the precipitated solid was collected by filtration to give compound 3 (65 mg, 83%).

ESIMS m/z: 512 (M+H)$^+$; $^1$H NMR (300 MHz, DMSO-d$_5$, δ): 1.64-1.67 (m, 2H), 1.81-1.84 (m, 2H), 2.31 (s, 3H), 2.66 (t, J=6.9 Hz, 2H), 2.81-2.86 (m, 1H), 3.01-3.08 (m, 2H), 3.99 (t, J=6.9 Hz, 2H), 4.26-4.31 (m, 2H), 5.43 (s, 1H), 7.02-7.15 (m, 3H), 7.26-7.33 (m, 3H), 7.42 (d, J=7.9 Hz, 1H), 7.79 (s, 1H), 8.29 (s, 1H).

Example 2

1-(benzyloxy)-3-chloro-4-(5-chloro-2-methylphenylamino)-5-[4-(4-fluorophenyl)piperidine-1-carbonyl]pyridin-2(1H)-one (compound 21)

(step 1) To diethyl 3-oxopentanedioate (5.0 mL, 27.4 mmol) were added triethyl orthoformate (4.57 mL, 27.4 mmol) and acetic anhydride (5.18 mL, 54.8 mmol), and the mixture was stirred at 135° C. for 2 hr. The reaction mixture was cooled to room temperature, and concentrated under reduced pressure. The residue (6.84 g from 7.84 g) was dissolved in DMF (50 mL), a solution (70 mL) of O-benzylhydroxylamine hydrochloride (4.20 g, 26.3 mmol) in DMF was added at 0° C., and the mixture was stirred at room temperature for 1 hr. To the reaction mixture was added water, and the mixture was extracted with ethyl acetate. The organic layer was washed with water and saturated brine, and dried over anhydrous magnesium sulfate. The solvent was evaporated under reduced pressure. The residue was dissolved in toluene (100 mL), DBU (7.20 mL, 47.8 mmol) was added, and the mixture was stirred with heating under reflux for 30 min. The reaction mixture was cooled to room temperature, 0.1 mol/L hydrochloric acid was added, and the mixture was extracted with ethyl acetate. The organic layer was washed with water and saturated brine, and dried over anhydrous magnesium sulfate. The solvent was evaporated under reduced pressure. The residue was purified by silica gel column chromatography (heptane/ethyl acetate=80/20-50/50) to give ethyl 1-(benzyloxy)-4-hydroxy-6-oxo-1,6-dihydropyridine-3-carboxylate (2.54 g, 3 steps 37%).

ESIMS m/z: 290 (M+H)$^+$; $^1$H NMR (300 MHz, CDCl$_3$, δ): 1.30 (t, J=7.0 Hz, 3H), 4.24 (q, J=7.0 Hz, 2H), 5.28 (s, 2H), 6.01 (s, 1H), 7.33-7.43 (m, 5H), 7.80 (s, 1H), 10.60 (s, 1H).

(step 2) Ethyl 1-(benzyloxy)-4-hydroxy-6-oxo-1,6-dihydropyridine-3-carboxylate (65.0 mg, 0.225 mmol) obtained in step 1 was dissolved in dichloromethane (2.0 mL), trifluoromethanesulfonic acid anhydride (0.057 mL, 0.337 mmol) and triethylamine (0.063 mL, 0.449 mmol) were added at 0° C. and the mixture was stirred for 30 min. To the reaction mixture was added saturated aqueous sodium hydrogen carbonate solution, and the mixture was extracted with ethyl acetate. The organic layer was dried over anhydrous magnesium sulfate and the solvent was evaporated under reduced pressure. The residue was purified by silica gel column chromatography (heptane/ethyl acetate=85/15-55/45) to give ethyl 1-(benzyloxy)-6-oxo-4-(trifluoromethylsulfonyloxy)-1,6-dihydropyridine-3-carboxylate (45.5 mg, 48%).

ESIMS m/z: 422 (M+H)$^+$; $^1$H NMR (400 MHz, CDCl$_3$, δ): 1.32 (t, J=6.8 Hz, 3H), 4.24 (q, J=6.8 Hz, 2H), 5.31 (s, 2H), 6.54 (s, 1H), 7.33-7.44 (m, 5H), 8.06 (s, 1H).

(step 3) Ethyl 1-(benzyloxy)-6-oxo-4-(trifluoromethylsulfonyloxy)-1,6-dihydropyridine-3-carboxylate (793 mg, 1.88 mmol) obtained in step 2, 5-chloro-2-methylaniline (400 mg, 2.82 mmol), 2,2'-bis(diphenylphosphino)-1,1'-binaphthyl(352 mg, 0.565 mmol) and cesium carbonate (1.23 g, 3.76 mmol) were suspended in toluene (10 mL), palladium (II) acetate (85.0 mg, 0.376 mmol) was added, and the mixture was stirred at 100° C. for 90 min. The reaction mixture was cooled to room temperature, saturated aqueous ammonium chloride solution was added, and the mixture was extracted with ethyl acetate. The organic layer was washed with saturated brine, and dried over anhydrous magnesium sulfate. The solvent was evaporated under reduced pressure. The residue was purified by silica gel column chromatography (heptane/ethyl acetate=90/10-60/40) to give ethyl 1-(benzyloxy)-4-(5-chloro-2-methylphenylamino)-6-oxo-1,6-dihydropyridine-3-carboxylate (650 mg, 84%).

ESIMS m/z: 413 (M+H)$^+$; $^1$H NMR (300 MHz, CDCl$_3$, δ): 1.30 (t, J=7.2 Hz, 3H), 2.20 (s, 3H), 4.23 (q, J=7.2 Hz, 2H), 5.28 (s, 2H), 5.62 (s, 1H), 7.12-7.29 (m, 3H), 7.36-7.48 (m, 5H), 7.91 (s, 1H).

(step 4) Using ethyl 1-(benzyloxy)-4-(5-chloro-2-methylphenylamino)-6-oxo-1,6-dihydropyridine-3-carboxylate (593 mg, 1.44 mmol) obtained in step 3, and in the same manner as in Example 21, step 3, ethyl 1-(benzyloxy)-5-chloro-4-(5-chloro-2-methylphenylamino)-6-oxo-1,6-dihydropyridine-3-carboxylate (481 mg, 75%) was obtained.

ESIMS m/z: 447 (M+H)$^+$; $^1$H NMR (400 MHz, CDCl$_3$, δ): 1.29 (t, J=6.8 Hz, 3H), 2.26 (s, 3H), 4.23 (q, J=6.8 Hz, 2H), 5.34 (s, 2H), 6.81 (d, J=2.0 Hz, 1H), 7.03 (dd, J=2.0, 7.8 Hz, 1H), 7.11 (d, J=7.8 Hz, 1H), 7.39-7.51 (m, 5H), 7.97 (s, 1H), 9.26 (s, 1H).

(step 5) Using ethyl 1-(benzyloxy)-5-chloro-4-(5-chloro-2-50 methylphenylamino)-6-oxo-1,6-dihydropyridine-3-carboxylate (480 mg, 1.07 mmol) obtained in step 4, and in the same manner as in Example 1, step 6, 1-(benzyloxy)-5-chloro-4-(5-chloro-2-methylphenylamino)-6-oxo-1,6-dihydropyridine-3-carboxylic acid (412 mg, 92%) was obtained.

ESIMS m/z: 419 (M+H)$^+$; $^1$H NMR (400 MHz, DMSO-d$_6$, δ): 2.21 (s, 3H), 5.27 (s, 2H), 6.90 (d, J=2.0 Hz, 1H), 7.09 (dd, J=2.0, 8.8 Hz, 1H), 7.24 (d, J=8.8 Hz, 1H), 7.41-7.47 (m, 3H), 7.52-7.58 (m, 2H), 8.51 (s, 1H), 9.58 (s, 1H).

(step 6) Using 1-(benzyloxy)-5-chloro-4-(5-chloro-2-methylphenylamino)-6-oxo-1,6-dihydropyridine-3-carboxylic acid (303 mg, 0.723 mmol) obtained in step 5, and in the same manner as in Example 1, step 4, compound 21 (423 mg, quantitative) was obtained.

ESIMS m/z: 580 (M+H)$^+$; $^1$H NMR (400 MHz, CDCl$_3$, δ): 1.18-1.33 (m, 2H), 1.64-1.73 (m, 2H), 2.27 (s, 3H), 2.42-2.65 (m, 3H), 3.41-3.99 (m, 2H), 5.35 (s, 2H), 6.58 (br s, 1H), 6.82 (d, J=2.0 Hz, 1H), 6.98-7.15 (m, 7H), 7.33-7.45 (m, 5H).

Example 3

4-(benzylamino)-5-[4-(4-fluorophenyl)piperidine-1-carbonyl]-1-[(1-methyl-1H-imidazol-2-yl)methyl]pyridin-2(1H)-one (compound 30)

(step 1) Using methyl 4,6-dichloronicotinate (3.00 g, 14.6 mmol) and benzylamine (2.34 g, 21.8 mmol), and in the same manner as in Example 1, step 1, methyl 4-(benzylamino)-6-chloronicotinate (3.63 g, 90%) was obtained.

ESIMS m/z: 277 (M+H)$^+$ (step 2) Using methyl 4-(benzylamino)-6-chloronicotinate (1.63 g, 5.89 mmol) obtained in step 1, and in the same manner as in Example 1, step 2, methyl 4-(benzylamino)-6-oxo-1,6-dihydropyridine-3-carboxylate (0.52 g, 34%) was obtained.

ESIMS m/z: 259 (M+H)$^+$ (step 3) Using methyl 4-(benzylamino)-6-oxo-1,6-dihydropyridine-3-carboxylate (0.52 g, 2.0 mmol) obtained in step 2, and in the same manner as in Example 1, step 3, 4-(benzylamino)-6-oxo-1,6-dihydropyridine-3-carboxylic acid (0.49 g, quantitative) was obtained.

ESIMS m/z: 245 (M+H)$^+$ (step 4) Using 4-(benzylamino)-6-oxo-1,6-dihydropyridine-3-carboxylic acid (0.49 g, 2.0 mmol) obtained in step 3, and in the same manner as in Example 1, step 4, 4-(benzylamino)-5-[4-(4-fluorophenyl)piperidine-1-carbonyl]pyridin-2(1H)-one (0.82 g, quantitative) was obtained.

ESIMS m/z: 406 (M+H)$^+$ (step 5) 4-(Benzylamino)-5-[4-(4-fluorophenyl)piperidine-1-carbonyl]pyridin-2(1H)-one (0.20 g, 0.49 mmol) obtained in step 4 was dissolved in DMF (2.5 mL), potassium carbonate (0.14 g, 0.99 mmol) and 2-(chloromethyl)-1-methyl-1H-imidazole (0.064 g, 0.49 mmol) were added, and the mixture was stirred at room temperature for 3 hr. To the reaction mixture was added water, and the mixture was extracted with ethyl acetate. The organic layer was washed with saturated brine, and dried over anhydrous magnesium sulfate. The solvent was evaporated under reduced pressure. The residue was purified by silica gel column chromatography (chloroform/methanol-100/0-70/30) to give compound 30 (0.18 g, 72%).

ESIMS m/z: 500 (M+H)$^+$; $^1$H NMR (300 MHz, CDCl$_3$, δ): 1.61-1.68 (m, 2H), 1.86-1.89 (m, 2H), 2.72-2.78 (m, 1H), 2.95-3.01 (m, 2H), 3.75 (s, 3H), 4.27-4.33 (m, 4H), 5.17 (s, 2H), 5.56 (s, 1H), 6.43-6.46 (m, 1H), 6.83 (s, 1H), 6.92 (s, 1H), 6.99-7.03 (m, 2H), 7.15-7.18 (m, 2H), 7.28-7.36 (m, 5H), 7.60 (s, 1H).

Example 4

3-chloro-4-(4-fluoro-2-methylphenylamino)-5-[4-(4-fluorophenyl)piperidine-1-carbonyl]-1-methoxypyridin-2(1H)-one (compound 194)

(step 1) Using ethyl 1-(benzyloxy)-6-oxo-4-(trifluoromethylsulfonyloxy)-1,6-dihydropyridine-3-carboxylate (105 mg, 0.249 mmol) obtained in Example 2, step 2, and 4-fluoro-2-methylaniline (0.042 mL, 0.374 mmol), and in the same manner as in Example 2, step 3, ethyl 1-(benzyloxy)-4-(4-fluoro-2-methylphenylamino)-6-oxo-1,6-dihydropyridine-3-carboxylate (76.4 mg, 77%) was obtained.

ESIMS m/z: 397 (M+H)$^+$; $^1$H NMR (300 MHz, CDCl$_3$, δ): 1.30 (t, J 6.9 Hz, 3H), 2.22 (s, 3H), 4.24 (q, J=6.9 Hz, 2H), 5.26 (s, 2H), 5.42 (s, 1H), 6.88-7.02 (m, 2H), 7.14-7.20 (m, 1H), 7.38-7.47 (m, 5H), 7.91 (s, 1H), 8.99 (s, 1H).

(step 2) Using ethyl 1-(benzyloxy)-4-(4-fluoro-2-methylphenylamino)-6-oxo-1,6-dihydropyridine-3-carboxylate (75.2 mg, 0.190 mmol) obtained in step 1, and in the same manner as in Example 2, step 4, ethyl 1-(benzyloxy)-5-chloro-4-(4-fluoro-2-methylphenylamino)-6-oxo-1,6-dihydropyridine-3-carboxylate (79.2 mg, 97%) was obtained.

ESIMS m/z: 431 (M+H)$^+$; $^1$H NMR (400 MHz, CDCl$_3$, δ): 1.30 (t, J=6.8 Hz, 3H), 2.26 (s, 3H), 4.24 (q, J=6.8 Hz, 2H), 5.31 (s, 2H), 6.79-6.92 (m, 3H), 7.40-7.50 (m, 5H), 7.97 (s, 1H), 9.30 (s, 1H).

(step 3) Ethyl 1-(benzyloxy)-5-chloro-4-(4-fluoro-2-methylphenylamino)-6-oxo-1,6-dihydropyridine-3-carboxylate (76.8 mg, 0.178 mmol) obtained in step 2 was dissolved in ethyl acetate (5.0 mL), 5% palladium-carbon (7.7 mg) was added, and the mixture was stirred under a hydrogen atmosphere at room temperature for 20 min. The reaction mixture was filtered through celite (registered trade mark). The solvent was evaporated under reduced pressure to give a crude product of ethyl 5-chloro-4-(4-fluoro-2-methylphenylamino)-1-hydroxy-6-oxo-1,6-dihydropyridine-3-carboxylate, which was used for the next step without purification.

(step 4) A crude product of ethyl 5-chloro-4-(4-fluoro-2-methylphenylamino)-1-hydroxy-6-oxo-1,6-dihydropyridine-3-carboxylate obtained in step 3 was dissolved in DMF (20 mL), methyl p-toluenesulfonate (0.040 mL, 0.267 mmol) and potassium carbonate (73.8 mg, 0.534 mmol) were added, and the mixture was stirred at room temperature for 2 hr. To the reaction mixture was added saturated aqueous ammonium chloride solution, and the mixture was extracted with ethyl acetate. The organic layer was washed with water and saturated brine, and dried over anhydrous magnesium sulfate. The solvent was evaporated under reduced pressure. The residue was purified by silica gel column chromatography (heptane/ethyl acetate=60/40-30/70) to give ethyl 5-chloro-4-(4-fluoro-2-methylphenylamino)-1-methoxy-6-oxo-1,6-dihydropyridine-3-carboxylate (56.6 mg, 2 steps 90%).

ESIMS m/z: 355 (M+H)$^+$; $^1$H NMR (400 MHz, CDCl$_3$, δ): 1.39 (t, =6.8 Hz, 3H), 2.28 (s, 3H), 4.14 (s, 3H), 4.34 (q, J=6.8 Hz, 2H), 6.79-6.93 (m, 3H), 8.40 (s, 1H), 9.34 (s, 1H).

(step 5) Using ethyl 5-chloro-4-(4-fluoro-2-methylphenylamino)-1-methoxy-6-oxo-1,6-dihydropyridine-3-carboxylate (55.3 mg, 0.156 mmol) obtained in step 4, and in the same manner as in Example 1, step 6, 5-chloro-4-(4-fluoro-2-methylphenylamino)-1-methoxy-6-oxo-1,6-dihydropyridine-3-carboxylic acid (45.1 mg, 89%) was obtained.

ESIMS m/z: 327 (M+H)$^+$; $^1$H NMR (400 MHz, DMSO-d$_6$, δ): 2.22 (s, 3H), 4.00 (s, 3H), 6.95-7.11 (m, 3H), 8.68 (s, 1H), 9.57 (br s, 1H).

(step 6) Using 5-chloro-4-(4-fluoro-2-methylphenylamino)-1-methoxy-6-oxo-1,6-dihydropyridine-3-carboxylic acid (40.2 mg, 0.123 mmol) obtained in step 5, and in the same manner as in Example 1, step 4, compound 194 (52.6 mg, 88%) was obtained.

ESIMS m/z: 488 (M+H)$^+$; $^1$H NMR (400 MHz, CDCl$_3$, δ): 1.33-1.48 (m, 2H), 1.74-1.83 (m, 2H), 2.33 (s, 3H), 2.47-2.68 (m, 3H), 3.92-4.09 (m, 2H), 4.12 (s, 3H), 6.43 (br s, 1H), 6.83-6.89 (m, 1H), 6.94-7.02 (m, 4H), 7.07-7.11 (m, 2H) 7.46 (s, 1H).

Example 5

3-chloro-4-(4-fluoro-2-methylphenylamino)-5-[4-(4-fluorophenyl)piperidine-1-carbonyl]-1-methylpyridin-2(1H)-one (compound 39)

Using 3,4-dichloro-5-[4-(4-fluorophenyl)piperidine-1-carbonyl]-1-methylpyridin-2(1H)-one (120 mg, 0.31 mmol) obtained in Example 12, step 5, and 4-fluoro-2-methylaniline (118 mg, 0.94 mmol), and in the same manner as in Example 12, step 6, compound 39 (28 mg, 19%) was obtained.

ESIMS m/z: 472 (M+H)$^+$; $^1$H NMR (400 MHz, CDCl$_3$, δ): 1.38-1.40 (m, 2H), 1.76-1.79 (m, 2H), 2.32 (s, 3H), 2.58-2.68 (m, 1H), 3.60 (s, 3H), 3.79-4.03 (m, 2H), 4.31-4.34 (m, 2H), 6.43 (s, 1H), 6.83-6.88 (m, 1H), 6.94-7.01 (m, 4H), 7.07-7.10 (m, 2H), 7.30 (s, 1H).

Example 6

3-chloro-4-(4-chloro-2-methylphenylamino)-5-[4-(4-fluorophenyl)piperidine-1-carbonyl]-1-methylpyridin-2(1H)-one (compound 40)

Using 3,4-dichloro-5-[4-(4-fluorophenyl) piperidine-1-carbonyl]-1-methylpyridin-2(1H)-one (120 mg, 0.31 mmol) obtained in Example 12, step 5, and 4-chloro-2-methylaniline (133 mg, 0.94 mmol), and in the same manner as in Example 12, step 6, compound 40 (14 mg, 8.8%) was obtained.

ESIMS m/z: 488 (M+H)$^+$; $^1$H NMR (400 MHz, CDCl$_3$, δ): 1.36-1.46 (m, 2H), 1.76-1.80 (m, 2H), 2.32 (s, 3H), 2.59-2.69 (m, 1H), 3.61 (s, 3H), 3.79-4.03 (m, 2H), 4.31-4.33 (m, 2H), 6.48 (s, 1H), 6.92-6.94 (m, 1H), 6.97-7.01 (m, 2H), 7.07-7.15 (m, 2H), 7.23-7.26 (m, 2H), 7.36 (s, 1H).

Example 7

4-(benzylamino)-3-chloro-5-[4-(4-fluorophenyl)piperidine-1-carbonyl]-1-methylpyridin-2(1H)-one (compound 42)

Using 3,4-dichloro-5-[4-(4-fluorophenyl)piperidine-1-carbonyl]-1-methylpyridin-2(1H)-one (200 mg, 0.52 mmol) obtained in Example 12, step 5, and benzylamine (168 mg, 1.57 mmol), and in the same manner as in Example 12, step 6, compound 42 (5.1 mg, 2.2%) was obtained.

ESIMS m/z: 454 (M+H)$^+$; $^1$H NMR (400 MHz, CDCl$_3$, δ): 1.20-1.35 (m, 2H), 1.75-1.95 (m, 2H), 2.60-2.95 (m, 2H), 2.64-2.76 (m, 1H), 3.54 (s, 3H), 4.00-4.69 (m, 4H), 6.50-7.04 (m, 3H), 7.07-7.20 (m, 3H), 7.28-7.30 (m, 1H), 7.31-7.42 (m, 4H).

Example 8

3-chloro-5-[4-(4-fluorophenyl)piperidine-1-carbonyl]-4-(4-methoxy-2-methylphenylamino)-1-methylpyridin-2(1H)-one (compound 43)

Using 3,4-dichloro-5-[4-(4-fluorophenyl)piperidine-1-carbonyl]-1-methylpyridin-2(1H)-one (200 mg, 0.52 mmol) obtained in Example 12, step 5, and 4-methoxy-2-methylaniline (215 mg, 1.57 mmol), and in the same manner as in Example 12, step 6, compound 43 (5.0 mg, 1.9%) was obtained.

ESIMS m/z: 484 (M+H)+; 1H NMR (300 MHz, CDCl3, δ): 1.10-1.30 (m, 2H), 1.60-1.75 (m, 2H), 2.09 (s, 3H), 2.45-2.60 (m, 1H), 2.51 (s, 3H), 2.60-2.70 (m, 2H), 3.76-3.83 (m, 2H), 3.81 (s, 3H), 6.62-6.66 (m, 1H), 6.75-6.85 (m, 4H), 6.95-6.97 (m, 2H), 7.04-7.06 (m, 1H), 7.28 (s, 1H).

Example 9

3-chloro-1-cyclopropyl-4-(4-fluoro-2-methylphenylamino)-5-[4-(4-fluorophenyl)piperidine-1-carbonyl]pyridin-2(1H)-one (compound 50)

(step 1) Using diethyl 3-oxopentanedioate (5.55 g, 27.4 mmol) and cyclopropylamine (3.92 g, 68.6 mmol), and in the same manner as in Example 12, steps 1, 2, 3 and 4,4,5-dichloro-1-cyclopropyl-6-oxo-1,6-dihydropyridine-3-carboxylic acid (2.52 g, 37%) was obtained.

ESIMS m/z: 247 (M+H)+

(step 2) Using 4,5-dichloro-1-cyclopropyl-6-oxo-1,6-dihydropyridine-3-carboxylic acid (2.00 g, 8.06 mmol) obtained in step 1, and in the same manner as in Example 1, step 4, 3,4-dichloro-1-cyclopropyl-5-[4-(4-fluorophenyl)piperidine-1-carbonyl]pyridin-2(1H)-one (1.15 g, 35%) was obtained.

ESIMS m/z: 409 (M+H)+

(step 3) Using 3,4-dichloro-1-cyclopropyl-5-[4-(4-fluorophenyl)piperidine-1-carbonyl]pyridin-2(1H)-one (100 mg, 0.24 mmol) obtained in step 2, and 4-fluoro-2-methylaniline (46 mg, 0.38 mmol), and in the same manner as in Example 12, step 6, compound 50 (70 mg, 57%) was obtained.

ESIMS m/z: 498 (M+H)+; 1H NMR (400 MHz, CDCl3, δ): 0.80-0.97 (m, 2H), 1.05-1.20 (m, 2H), 1.23-1.48 (m, 2H), 1.51-1.67 (m, 2H), 2.33 (s, 3H), 2.53-2.70 (m, 1H), 3.28-3.32 (m, 1H), 3.68-4.14 (m, 2H), 4.31-4.33 (m, 2H), 6.41 (s, 1H), 6.80-6.88 (m, 1H), 6.97-7.02 (m, 4H), 7.06-7.14 (m, 2H), 7.26 (s, 1H).

Example 10

3-chloro-4-(5-chloro-2-methylphenylamino)-5-[4-(4-fluorophenyl)piperidine-1-carbonyl]-1-methylpyridin-2(1H)-one (compound 74)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 5-chloro-2-methylaniline (133 mg, 0.94 mmol), and in the same manner as in Example 12, step 6, compound 74 (67 mg, 65%) was obtained.

ESIMS m/z: 488 (M+H)+; 1H NMR (400 MHz, CDCl3, δ): 1.30-1.60 (m, 2H), 1.73-1.86 (m, 2H), 2.31 (s, 3H), 2.55-2.70 (m, 1H), 3.60 (s, 3H), 3.85-4.15 (m, 2H), 4.31-4.33 (m, 2H), 6.51 (s, 1H), 6.94-7.02 (m, 3H), 7.03-7.12 (m, 3H), 7.16 (d, J=8.8 Hz, 1H), 7.33 (s, 1H).

Example 11

3-chloro-4-(cyclohexylamino)-5-[4-(4-fluorophenyl)piperidine-1-carbonyl]-1-methylpyridin-2(1H)-one (compound 81)

Using 3,4-dichloro-5-[4-(4-fluorophenyl)piperidine-1-carbonyl]-1-methylpyridin-2(1H)-one (70 mg, 0.18 mmol) obtained in Example 12, step 5, and cyclohexylamine (54 mg, 0.55 mmol), and in the same manner as in Example 12, step 6, compound 81 (12 mg, 15%) was obtained.

ESIMS m/z: 446 (M+H)+; 1H NMR (400 MHz, CDCl3, δ): 1.17-1.32 (m, 6H), 1.60-1.62 (m, 3H), 1.72-1.78 (m, 2H), 1.92-1.95 (m, 3H), 2.74-2.80 (m, 1H), 2.90-3.37 (m, 3H), 3.55 (s, 3H), 4.10-4.29 (m, 2H), 6.99-7.04 (m, 2H), 7.13-7.16 (m, 2H), 7.18-7.24 (m, 1H), 7.27 (s, 1H).

Example 12

4-{3-chloro-5-[4-(4-fluorophenyl)piperidine-1-carbonyl]-1-methyl-2-oxo-1,2-dihydropyridin-4-ylamino}-3-methylbenzonitrile (compound 100)

(step 1) To diethyl 3-oxopentanedioate (10 mL, 55 mmol) were added triethyl orthoformate (9.1 mL, 55 mmol) and acetic anhydride (10.4 mL, 110 mmol), and the mixture was stirred at 135° C. for 1 hr. The reaction mixture was cooled to room temperature, and concentrated under reduced pressure. To the residue were added water (55 mL) and methylamine (9.87 mL, 137 mmol), and the mixture was stirred at room temperature overnight. The reaction mixture was extracted with ethyl acetate, and the aqueous layer was neutralized with hydrochloric acid and extracted with ethyl acetate. The solvent of the combined organic layer was evaporated under reduced pressure to give ethyl 4-hydroxy-1-methyl-6-oxo-1,6-dihydropyridine-3-carboxylate (9.2 g, 85%).

ESIMS m/z: 198 (M+H)+

(step 2) To ethyl 4-hydroxy-1-methyl-6-oxo-1,6-dihydropyridine-3-carboxylate (9.2 g, 47 mmol) obtained in step 1 were added phosphorus oxychloride (26.1 mL, 280 mmol) and triethylamine (6.5 mL, 47 mmol), and the mixture was stirred at 50° C. for 3 hr. The reaction mixture was cooled to room temperature, and the solvent was evaporated under reduced pressure. To the residue was added saturated aqueous sodium hydrogen carbonate solution (100 mL), and the mixture was extracted with ethyl acetate. The solvent of the organic layer was evaporated under reduced pressure to give ethyl 4-chloro-1-methyl-6-oxo-1,6-dihydropyridine-3-carboxylate (6.0 g, 60%). ESIMS m/z: 216 (M+H)+

(step 3) To ethyl 4-chloro-1-methyl-6-oxo-1,6-dihydropyridine-3-carboxylate (6.0 g, 28 mmol) obtained in step 2 were added N-chlorosuccinimide (4.1 g, 31 mmol) and DMF (130 mL), and the mixture was stirred at room temperature for 1 hr. To the reaction mixture was added water (200 mL), and the mixture was extracted with ethyl acetate. The organic layer was washed with hydrochloric acid, and dried over anhydrous magnesium sulfate. The solvent was evaporated under reduced pressure. The residue was purified by silica gel column chromatography (chloroform/methanol=100/0-70/30) to give ethyl 4,5-dichloro-1-methyl-6-oxo-1,6-dihydropyridine-3-carboxylate (5.5 g, 79%). ESIMS m/z: 250 (M+H)+

(step 4) To ethyl 4,5-dichloro-1-methyl-6-oxo-1,6-dihydropyridine-3-carboxylate (5.5 g, 22 mmol) obtained in step 3 were added 1 mol/L aqueous lithium hydroxide solution (66 mL, 66 mmol), THF (35 mL) and methanol (8.8 mL), and the mixture was stirred at room temperature for 1 hr. To the reaction mixture was added hydrochloric acid to pH=1, and the precipitated solid was collected by filtration to give 4,5-dichloro-1-methyl-6-oxo-1,6-dihydropyridine-3-carboxylic acid (4.9 g, quantitative).

ESIMS m/z: 222 (M+H)+

(step 5) Using 4,5-dichloro-1-methyl-6-oxo-1,6-dihydropyridine-3-carboxylic acid (0.52 g, 2.3 mmol) obtained in step 4, and in the same manner as in Example 1, step 4, 3,4-dichloro-5-[4-(4-fluorophenyl)piperidine-1-carbonyl]-1-methylpyridin-2(1H)-one (0.41 g, 46%) was obtained.

ESIMS m/z: 383 (M+H)$^+$; $^1$H NMR (400 MHz, CDCl$_3$, δ): 1.51-1.62 (m, 2H), 1.90-1.93 (m, 2H), 2.72-2.78 (m, 1H), 2.89-2.96 (m, 2H), 3.62 (s, 3H), 4.31-4.34 (m, 2H), 6.96-7.02 (m, 2H), 7.11-7.14 (m, 2H), 7.41 (s, 1H).

(step 6) 4-Amino-3-methylbenzonitrile (41 mg, 0.31 mmol) was dissolved in THF (1.0 mL), sodium hydride (33 mg, 0.84 mmol, 60% in oil) was added, and the mixture was stirred at room temperature for 1 hr. To the reaction mixture was added 3,4-dichloro-5-[4-(4-fluorophenyl)piperidine-1-carbonyl]-1-methylpyridin-2(1H)-one (80 mg, 0.21 mmol) obtained in step 5, and the mixture was stirred with heating under reflux for 4 hr. To the reaction mixture was added water, and the mixture was extracted with ethyl acetate. The organic layer was washed with water, and dried over anhydrous magnesium sulfate. The solvent was evaporated under reduced pressure. The residue was purified by silica gel column chromatography (chloroform/methanol-100/0-70/30) to give compound 100 (77 mg, 77%)

ESIMS m/z: 479 (M+H)$^+$; $^1$H NMR (400 MHz, CDCl$_3$, δ): 1.15-1.50 (m, 2H), 1.60-1.89 (m, 2H), 2.39 (s, 3H), 2.60-2.70 (m, 1H), 3.07-3.13 (m, 2H), 3.63 (s, 3H), 3.85-4.25 (m, 2H), 6.88-6.92 (m, 2H), 6.96-7.01 (m, 2H), 7.03-7.04 (m, 2H), 7.42-7.50 (m, 2H), 7.51 (s, 1H).

Example 13

4-chloro-2-{3-chloro-5-[4-(4-fluorophenyl)piperidine-1-carbonyl]-1-methyl-2-oxo-1,2-dihydropyridin-4-ylamino}benzonitrile (compound 103)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 2-amino-4-chlorobenzonitrile (48 mg, 0.31 mmol), and in the same manner as in Example 12, step 6, compound 103 (55 mg, 53%) was obtained.

ESIMS m/z: 499 (M+H)$^+$; $^1$H NMR (400 MHz, CDCl$_3$, δ): 1.20-1.90 (m, 4H), 2.60-2.75 (m, 1H), 3.65 (s, 3H), 3.85-4.10 (m, 2H), 4.30-4.35 (m, 2H), 6.92-7.05 (m, 3H), 7.05-7.22 (m, 4H), 7.49-7.62 (m, 2H).

Example 14

3-chloro-4-[3-chloro-4-(methylthio)phenylamino]-5-[4-(4-fluorophenyl)piperidine-1-carbonyl]-1-methylpyridin-2(1H)-one (compound 111)

Using 3,4-dichloro-5-[4-(4-fluorophenyl)piperidine-1-carbonyl]-1-methylpyridin-2(1H)-one (120 mg, 0.31 mmol) obtained in Example 12, step 5, and 3-chloro-4-(methylthio)aniline (82 mg, 0.47 mmol), and in the same manner as in Example 12, step 6, compound 111 (74 mg, 45%) was obtained.

ESIMS m/z: 520 (M+H)$^+$; $^1$H NMR (400 MHz, CDCl$_3$, δ): 1.25-1.59 (m, 2H), 1.70-1.82 (m, 2H), 2.47 (s, 3H), 2.55-2.68 (m, 1H), 3.61 (s, 3H), 3.70-4.10 (m, 2H), 4.22-4.31 (m, 2H), 6.70 (s, 1H), 6.93-7.04 (m, 3H), 7.05-7.18 (m, 4H), 7.44 (s, 1H).

Example 15

4-(2,4-difluorophenylamino)-5-[4-(4-fluorophenyl)piperidine-1-carbonyl]-1,3-dimethylpyridin-2(1H)-one (compound 125)

(step 1) Using 4-chloro-1,5-dimethyl-6-oxo-1,6-dihydropyridine-3-carboxylic acid (8.56 g, 42.5 mmol) obtained by the method described in a document (Journal of Medicinal Chemistry, 2006, vol. 9, p 441), and in the same manner as in Example 1, step 4, 4-chloro-5-[4-(4-fluorophenyl)piperidine-1-carbonyl]-1,3-dimethylpyridin-2(1H)-one (15.4 g, quantitative) was obtained.

ESIMS m/z: 363 (M+H)$^+$ (step 2) Using 4-chloro-5-[4-(4-fluorophenyl)piperidine-1-carbonyl]-1,3-dimethylpyridin-2(1H)-one (80 mg, 0.22 mmol) obtained in step 1, and 2,4-difluoroaniline (43 mg, 0.33 mmol), and in the same manner as in Example 12, step 6, compound 125 (64 mg, 64%) was obtained.

ESIMS m/z: 456 (M+H)$^+$; $^1$H NMR (400 MHz, CDCl$_3$, δ): 1.30-1.55 (m, 2H), 1.70-1.90 (m, 2H), 1.98 (s, 3H), 2.57 (s, 3H), 2.57-2.73 (m, 1H), 3.90-4.35 (m, 4H), 6.23 (br s, 1H), 6.70-6.85 (m, 2H), 6.85-6.93 (m, 1H), 6.93-7.02 (m, 2H), 7.02-7.12 (m, 2H), 7.34 (s, 1H).

Example 16

3-chloro-4-(4-chloro-2-fluorophenylamino)-5-[4-(4-fluorophenyl)piperidine-1-carbonyl]-1-methylpyridin-2(1H)-one (compound 130)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 4-chloro-2-fluoroaniline (46 mg, 0.31 mmol), and in the same manner as in Example 12, step 6, compound 130 (85 mg, 83%) was obtained.

ESIMS m/z: 492 (M+H)$^+$; $^1$H NMR (400 MHz, CDCl$_3$, δ): 1.25-1.55 (m, 2H), 1.60-1.80 (m, 2H), 2.57-2.69 (m, 1H), 3.61 (s, 3H), 3.75-4.10 (m, 2H), 4.28-4.33 (m, 2H), 6.50 (br s, 1H), 6.95-7.12 (m, 6H), 7.15-7.21 (m, 1H), 7.44 (s, 1H).

Example 17

3-chloro-4-(2,4-difluorophenylamino)-5-[4-(4-fluorophenyl)piperidine-1-carbonyl]-1-(2-methoxyethyl)pyridin-2(1H)-one (compound 144)

Using diethyl 3-oxopentandioate (0.19 mL, 1.09 mmol), 2-methoxyethanamine and 2,4-difluoroaniline, and in the same manner as in Example 9, steps 1, 2 and 3, compound 144 (34 mg, 6.0%) was obtained.

ESIMS m/z: 520 (M+H)$^+$; $^1$H NMR (300 MHz, CDCl$_3$, δ): 1.35-1.70 (m, 2H), 1.72-1.88 (m, 2H), 2.40-3.00 (m, 3H), 3.30 (s, 3H), 3.67 (t, J=4.8 Hz, 2H), 3.90-4.25 (m, 4H), 6.60 (s, 1H), 6.80-7.40 (m, 7H), 7.61 (s, 1H).

Example 18

3-chloro-5-[4-(4-fluorophenyl)piperidine-1-carbonyl]-4-(4-methoxy-2-methylphenylamino)-1-(pyridin-3-ylmethyl)pyridin-2(1H)-one (compound 154)

Using diethyl 3-oxopentandioate (0.43 mL, 2.38 mmol), pyridin-3-ylmethanamine and 4-methoxy-2-methylaniline, and in the same manner as in Example 9, steps 1, 2 and 3, compound 154 (20 mg, 1.5%) was obtained.

ESIMS m/z: 561 (M+H)$^+$; $^1$H NMR (300 MHz, DMSO-d$_5$, δ): 1.25-1.75 (m, 4H), 2.17 (s, 3H), 2.60-3.10 (m, 3H), 3.70-4.30 (m, 2H), 3.72 (s, 3H), 5.13 (s, 2H), 6.68-6.82 (m,

2H), 6.93 (d, J=6.0 Hz, 1H), 7.10-7.35 (m, 4H), 7.40-7.60 (m, 1H), 7.76 (s, 1H), 7.82 (d, J=6.0 Hz, 1H), 8.50-8.58 (m, 1H), 8.61 (s, 1H).

Example 19

3-chloro-5-[4-(4-fluorophenyl)piperidine-1-carbonyl]-1-methyl-4-(6-methylpyridin-3-ylamino)pyridin-2(1H)-one (compound 157)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 6-methylpyridin-3-ylamine (34 mg, 0.31 mmol), and in the same manner as in Example 12, step 6, compound 157 (54 mg, 57%) was obtained.
ESIMS m/z: 455 (M+H)$^+$; $^1$H NMR (400 MHz, CDCl$_3$, δ): 1.25-1.55 (m, 2H), 1.60-1.80 (m, 2H), 2.10-3.00 (m, 3H), 2.54 (s, 3H), 3.60 (s, 3H), 3.65-4.10 (m, 2H), 6.65 (br s, 1H), 6.96-7.00 (m, 2H), 7.09-7.14 (m, 3H), 7.30 (dd, J=8.3, 2.4 Hz, 1H), 7.39 (s, 1H), 8.33 (s, 1H).

Example 20

3-chloro-4-(5-chloro-2-methylphenylamino)-1-(2-fluoroethyl)-5-[4-(4-fluorophenyl)piperidine-1-carbonyl]pyridin-2(1H)-one (compound 160)

Using diethyl 3-oxopentandioate (0.065 mL, 0.36 mmol), 2-fluoroethylamine and 5-chloro-2-methylaniline, and in the same manner as in Example 9, steps 1, 2 and 3, compound 160 (59 mg, 32%) was obtained.
ESIMS m/z: 520 (M+H)$^+$; $^1$H NMR (300 MHz, CDCl$_3$, δ): 1.40-1.60 (m, 2H), 1.78-1.92 (m, 2H), 2.32 (s, 3H), 2.40-3.15 (m, 3H), 3.90-4.50 (m, 4H), 4.66 (t, J=4.0 Hz, 1H), 4.82 (t, J=4.0 Hz, 1H), 6.68 (s, 1H), 6.90-7.65 (m, 8H).

Example 21

1-allyl-3-chloro-4-(5-chloro-2-methylphenylamino)-5-[4-(4-fluorophenyl)piperidine-1-carbonyl]pyridin-2(1H)-one (compound 166)

(step 1) Using methyl 4,6-dichloronicotinate (8.00 g, 38.8 mmol) and 5-chloro-2-methylaniline (8.25 g, 58.2 mmol), and in the same manner as in Example 1, step 1, methyl 6-chloro-4-(5-chloro-2-methylphenylamino)nicotinate (6.68 g, 55%) was obtained.
ESIMS m/z: 311 (M+H)$^+$
(step 2) Using methyl 6-chloro-4-(5-chloro-2-methylphenylamino)nicotinate (5.20 g, 16.7 mmol) obtained in step 1, and in the same manner as in Example 1, step 2, methyl 4-(5-chloro-2-methylphenylamino)-6-oxo-1,6-dihydropyridine-3-carboxylate (3.78 g, 77%) was obtained.
ESIMS m/z: 293 (M+H)$^+$
(step 3) Methyl 4-(5-chloro-2-methylphenylamino)-6-oxo-1,6-dihydropyridine-3-carboxylate (2.0 g, 6.8 mmol) obtained in step 2 was dissolved in DMF (68 mL), N-chlorosuccinimide (1.0 g, 7.5 mmol) was added, and the mixture was stirred at room temperature for 3 hr. To the reaction mixture was added water, and the precipitated solid was collected by filtration to give methyl 5-chloro-4-(5-chloro-2-methylphenylamino)-6-oxo-1,6-dihydropyridine-3-carboxylate (1.79 g, 80%).
ESIMS m/z: 327 (M+H)$^+$; $^1$H NMR (400 MHz, CDCl$_3$, δ): 2.28 (s, 3H), 3.87 (s, 3H), 6.89 (d, J=2.0 Hz, 1H), 7.06 (dd, J=8.8, 2.0 Hz, 1H), 7.13 (d, J=8.8 Hz, 1H), 8.22 (s, 1H), 9.51 (s, 1H).

(step 4) Using methyl 5-chloro-4-(5-chloro-2-methylphenylamino)-6-oxo-1,6-dihydropyridine-3-carboxylate (1.80 g, 5.50 mmol) obtained in step 3, and in the same manner as in Example 1, step 3, 5-chloro-4-(5-chloro-2-methylphenylamino)-6-oxo-1,6-dihydropyridine-3-carboxylic acid (1.55 g, 90%) was obtained.
ESIMS m/z: 313 (M+H)$^+$
(step 5) Using 5-chloro-4-(5-chloro-2-methylphenylamino)-6-oxo-1,6-dihydropyridine-3-carboxylic acid (1.32 g, 4.22 mmol) obtained in step 4, and in the same manner as in Example 1, step 4, 3-chloro-4-(5-chloro-2-methylphenylamino)-5-[4-(4-fluorophenyl)piperidine-1-carbonyl] pyridin-2(1H)-one (0.72 g, 36%) was obtained.
ESIMS m/z: 474 (M+H)$^+$
(step 6) Using 3-chloro-4-(5-chloro-2-methylphenylamino)-5-[4-(4-fluorophenyl)piperidine-1-carbonyl]pyridin-2(1H)-one (50 mg, 0.11 mmol) obtained in step 5, and allylbromide (0.011 mL, 0.13 mmol), and in the same manner as in Example 3, step 5, compound 166 (49 mg, 89%) was obtained.
ESIMS m/z: 514 (M+H)$^+$; $^1$H NMR (400 MHz, CDCl$_3$, δ): 1.37-1.46 (m, 2H), 1.78-1.82 (m, 2H), 2.31 (s, 3H), 2.59-2.75 (m, 3H), 3.95-4.10 (m, 2H), 4.61 (d, J=5.9 Hz, 2H), 5.28-5.34 (m, 2H), 5.92-6.01 (m, 1H), 6.58 (s, 1H), 6.94-7.01 (m, 3H), 7.05-7.11 (m, 3H), 7.16 (d, J=7.8 Hz, 1H), 7.26 (s, 1H).

Example 22

2-{3-chloro-4-(5-chloro-2-methylphenylamino)-5-[4-(4-fluorophenyl)piperidine-1-carbonyl]-2-oxopyridine-1(2H)-yl}acetonitrile (compound 168)

Using 3-chloro-4-(5-chloro-2-methylphenylamino)-5-[4-(4-fluorophenyl)piperidine-1-carbonyl]pyridin-2(1H)-one (177 mg, 0.373 mmol) obtained in Example 21, step 5, and bromoacetonitrile (0.039 mL, 0.56 mmol), and in the same manner as in Example 1, step 5, compound 168 (150 mg, 78%) was obtained.
ESIMS m/z: 513 (M+H)$^+$; $^1$H NMR (400 MHz, CDCl$_3$, δ): 1.42-1.55 (m, 2H), 1.81-1.84 (m, 2H), 2.31 (s, 3H), 2.63-2.69 (m, 1H), 2.95-3.00 (m, 2H), 3.95-4.05 (m, 2H), 4.96 (s, 2H), 6.83 (s, 1H), 6.97-7.01 (m, 3H), 7.11-7.20 (m, 4H), 7.47 (s, 1H).

Example 23

3-({3-chloro-4-(5-chloro-2-methylphenylamino)-5-[4-(4-fluorophenyl)piperidine-1-carbonyl]-2-oxopyridin-1(2H)-yl}methyl)-1,2,4-oxadiazol-5(4H)-one (compound 169)

Compound 168 (51 mg, 0.099 mmol) was dissolved in DMSO (1.0 mL), 50% hydroxylamine solution (0.12 mL, 2.0 mmol) was added, and the mixture was stirred at room temperature for 4 hr. To the reaction mixture was added water, and the mixture was extracted with ethyl acetate. The organic layer was washed with water and dried over anhydrous sodium sulfate, and the solvent was evaporated under reduced pressure. The residue was dissolved in 1,4-dioxane (1.0 mL), CDI (24 mg, 0.15 mmol) and DBU (0.022 mL, 0.15 mmol) were added, and the mixture was stirred at 80° C. for 2 hr. To the reaction mixture was added 5% aqueous citric acid solution (2.0 mL), and the mixture was extracted with ethyl acetate. The organic layer was washed with water and dried over anhydrous sodium sulfate, and the solvent was evaporated under reduced pressure. The residue was purified by preparative HPLC (XBridge™ Prep C18 OBD Column, 5 μm, 19×150 mm, manufactured by Waters) (MeCN/0.05% aqueous TFA solution) to give compound 169 (40 mg, 70%).

ESIMS m/z: 572 (M+H)$^+$; $^1$H NMR (300 MHz, CDCl$_3$, δ): 1.42-1.51 (m, 2H), 1.81-1.85 (m, 2H), 2.30 (s, 3H), 2.63-2.70 (m, 3H), 3.97-4.05 (m, 2H), 5.02 (s, 2H), 6.83 (s, 1H), 6.96-7.02 (m, 3H), 7.10-7.19 (m, 4H), 7.38 (s, 1H).

Example 24

1-[(1H-tetrazol-5-yl)methyl]-3-chloro-4-(5-chloro-2-methylphenylamino)-5-[4-(4-fluorophenyl)piperidine-1-carbonyl]pyridin-2(1H)-one (compound 170)

Compound 168 (32 mg, 0.062 mmol) was dissolved in toluene (2.0 mL), trimethylsilylazide (0.083 mL, 0.62 mmol) and dibutyltin oxide (7.7 mg, 0.031 mmol) were added, and the mixture was stirred at 110° C. for 6 hr. To the reaction mixture was added methanol (1.0 mL), and the mixture was stirred at room temperature for 1 hr. To the reaction mixture was added water (2.0 mL), and the mixture was extracted with ethyl acetate. The organic layer was washed with water and dried over anhydrous sodium sulfate, and the solvent was evaporated under reduced pressure. The residue was purified by silica gel column chromatography (chloroform/methanol=99/1-90/10) to give compound 170 (16 mg, 46%) was obtained.

ESIMS m/z: 556 (M+H)$^+$; $^1$H NMR (300 MHz, CDCl$_3$, δ): 1.48-1.58 (m, 2H), 1.82-1.86 (m, 2H), 2.30 (s, 3H), 2.45-2.71 (m, 3H), 3.95-4.15 (m, 2H), 5.46 (s, 2H), 6.78 (s, 1H), 6.94 (d, J=1.8 Hz, 1H), 6.97-7.03 (m, 2H), 7.11-7.20 (m, 4H), 7.62 (s, 1H).

Example 25

4-(benzo[d]thiazol-6-ylamino)-3-chloro-5-[4-(4-fluorophenyl)piperidine-1-carbonyl]-1-methylpyridin-2(1H)-one (compound 173)

Using 3,4-dichloro-5-[4-(4-fluorophenyl)piperidine-1-carbonyl]-1-methylpyridin-2(1H)-one (80 mg, 0.21 mmol) obtained in Example 12, step 5, and benzo[d]thiazol-6-ylamine (47 mg, 0.31 mmol), and in the same manner as in Example 12, step 6, compound 173 (60 mg, 58%) was obtained.

ESIMS m/z: 497 (M+H)$^+$; $^1$H NMR (400 MHz, CDCl$_3$, δ): 1.20-1.50 (m, 2H), 1.50-1.85 (m, 2H), 2.30-2.80 (m, 3H), 3.63 (s, 3H), 3.66-3.90 (m, 2H), 6.86 (br s, 1H), 6.91-7.10 (m, 4H), 7.20-7.30 (m, 1H), 7.48 (s, 1H), 7.64 (br s, 1H), 8.09 (d, J=8.8 Hz, 1H), 8.95 (s, 1H).

Example 26

3-chloro-5-[4-(4-fluorophenyl)piperidine-1-carbonyl]-1-methyl-4-(1-methyl-1H-indazol-6-ylamino)pyridin-2(1H)-one (compound 175)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 1-methyl-1H-indazol-6-amine (46 mg, 0.31 mmol), and in the same manner as in Example 12, step 6, compound 175 (94 mg, 91%) was obtained. ESIMS m/z: 494 (M+H)$^+$; $^1$H NMR (400 MHz, CDCl$_3$, δ): 1.20-1.50 (m, 2H), 1.80-2.15 (m, 2H), 2.30-3.20 (m, 3H), 3.45-3.90 (m, 2H), 3.63 (s, 3H), 4.03 (s, 3H), 6.85-7.10 (m, 7H), 7.50 (s, 1H), 7.68 (d, J=8.8 Hz, 1H), 7.92 (s, 1H).

Example 27

4-(1H-benzo[d][1,2,3]triazol-6-ylamino)-3-chloro-5-[4-(4-fluorophenyl)piperidine-1-carbonyl]-1-methylpyridin-2(1H)-one (compound 177)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 1H-benzo[d][1,2,3]triazol-6-ylamine (42 mg, 0.31 mmol), and in the same manner as in Example 12, step 6, compound 177 (8.0 mg, 8.9%) was obtained. ESIMS m/z: 481 (M+H)$^+$; $^1$H NMR (400 MHz, CDCl$_3$, δ): 1.10-1.90 (m, 4H), 2.50-2.65 (m, 1H), 2.65-3.40 (m, 2H), 3.50-3.90 (m, 2H), 3.78 (s, 3H), 6.98 (br s, 1H), 6.90-7.10 (m, 4H), 7.18 (d, J=8.8 Hz, 1H), 7.36 (br s, 1H), 7.95 (br s, 1H), 8.04 (d, J=7.8 Hz, 1H).

Example 28

2-chloro-4-{5-[4-(4-fluorophenyl)piperidine-1-carbonyl]-1,3-dimethyl-2-oxo-1,2-dihydropyridin-4-ylamino}benzonitrile (compound 178)

Using 4-chloro-5-[4-(4-fluorophenyl)piperidine-1-carbonyl]-1,3-dimethylpyridin-2(1H)-one (80 mg, 0.22 mmol) obtained in Example 15, step 1, and 4-amino-2-chlorobenzonitrile (50 mg, 0.33 mmol), and in the same manner as in Example 12, step 6, compound 178 (41 mg, 39%) was obtained.

ESIMS m/z: 479 (M+H)$^+$; $^1$H NMR (300 MHz, CDCl$_3$, δ): 1.30-1.50 (m, 2H), 1.80-1.90 (m, 2H), 1.94 (s, 3H), 2.65-2.80 (m, 1H), 2.80-3.10 (m, 1H), 3.59 (s, 3H), 4.15-4.50 (m, 2H), 6.59-6.67 (m, 1H), 6.70-6.80 (m, 1H), 6.90-7.05 (m, 4H), 7.34 (br s, 1H), 7.48 (d, J=8.8 Hz, 1H), 7.51 (br s, 1H).

Example 29

4-(benzo[d][1,3]dioxol-5-ylamino)-3-chloro-5-[4-(4-fluorophenyl)piperidine-1-carbonyl]-1-methylpyridin-2(1H)-one (compound 179)

Using 3,4-dichloro-5-[4-(4-fluorophenyl)piperidine-1-carbonyl]-1-methylpyridin-2(1H)-one (80 mg, 0.21 mmol) obtained in Example 12, step 5, and benzo[d][1,3]dioxol-5-ylamine (43 mg, 0.31 mmol), and in the same manner as in Example 12, step 6, compound 179 (90 mg, 89%) was obtained. ESIMS m/z: 484 (M+H)$^+$; $^1$H NMR (400 MHz, CDCl$_3$, δ): 1.30-1.50 (m, 2H), 1.70-1.95 (m, 2H), 2.30-2.90 (m, 3H), 3.40-4.10 (m, 2H), 3.58 (s, 3H), 5.97 (s, 2H), 6.50-6.60 (m, 2H), 6.60-6.65 (m, 1H), 6.75 (d, J=8.8 Hz, 1H), 6.95-7.05 (m, 2H), 7.06-7.18 (m, 2H), 7.39 (br s, 1H).

Example 30

3-chloro-4-(2,4-difluorophenylamino)-5-[4-(4-fluorophenyl)piperidine-1-carbonyl]-1-(2-hydroxyethyl)pyridin-2(1H)-one (compound 183)

(step 1) Using methyl 4,6-dichloronicotinate (19.5 g, 95.5 mmol) and 2,4-difluoroaniline (12.3 g, 95.5 mmol), and in the same manner as in Example 1, steps 1, 2 and 3, 4-(2,4-difluorophenylamino)-6-oxo-1,6-dihydropyridine-3-carboxylic acid (8.5 g, 33%) was obtained.

ESIMS m/z: 267 (M+H)+

(step 2) Using 4-(2,4-difluorophenylamino)-6-oxo-1,6-dihydropyridine-3-carboxylic acid (8.5 g, 32 mmol) obtained in step 1, and in the same manner as in Example 21, step 3, 5-chloro-4-(2,4-difluorophenylamino)-6-oxo-1,6-dihydropyridine-3-carboxylic acid (5.0 g, 52%) was obtained.

ESIMS m/z: 301 (M+H)+

(step 3) Using 5-chloro-4-(2,4-difluorophenylamino)-6-oxo-1,6-dihydropyridine-3-carboxylic acid (0.17 g, 0.57 mmol) obtained in step 2, and 2-bromoethanol, and in the same manner as in Example 1, step 4 and Example 3, step 5, compound 183 (55 mg, 19%) was obtained.

ESIMS m/z: 506 (M+H)+; $^1$H NMR (300 MHz, DMSO-$d_6$, δ): 1.37-1.80 (m, 4H), 1.85-2.50 (m, 1H), 2.65-3.10 (m, 2H), 3.55-3.70 (m, 2H), 3.70-4.20 (m, 4H), 4.90 (br s, 1H), 6.95-7.40 (m, 7H), 7.49 (s, 1H), 8.00 (s, 1H).

Example 31

3-chloro-4-(2,4-difluorophenylamino)-5-[4-(4-fluorophenyl)piperidine-1-carbonyl]-1-[(5-methyl-1,3,4-oxadiazol-2-yl)methyl]pyridin-2(1H)-one (compound 184)

Using methyl 4,6-dichloronicotinate (0.43 g, 2.15 mmol), 2,4-difluoroaniline and 2-(chloromethyl)-5-methyl-1,3,4-oxadiazole, and in the same manner as in Example 30, steps 1, 2 and 3, compound 184 (96 mg, 8.0%) was obtained.

ESIMS m/z: 558 (M+H)+; $^1$H NMR (300 MHz, DMSO-$d_6$, δ): 1.15-1.80 (m, 4H), 1.95-2.30 (m, 1H), 2.48 (s, 3H), 2.65-3.10 (m, 2H), 3.85-4.20 (m, 2H), 5.34 (s, 2H), 7.05-7.40 (m, 7H), 7.80 (s, 1H), 8.20 (s, 1H).

Example 32

3-chloro-4-(5-chloro-2-methylphenylamino)-5-[4-(4-fluorophenyl)piperidine-1-carbonyl]-1-(2-hydroxyethyl)pyridin-2(1H)-one (compound 186)

Using methyl 4,6-dichloronicotinate (0.32 g, 1.57 mmol), 5-chloro-2-methylaniline and 2-bromoethanol, and in the same manner as in Example 30, steps 1, 2 and 3, compound 186 (114 mg, 14%) was obtained.

ESIMS m/z: 518 (M+H)+; $^1$H NMR (300 MHz, DMSO-$d_6$, δ): 1.15-1.90 (m, 4H), 1.90-2.30 (m, 1H), 2.19 (s, 3H), 2.60-3.20 (m, 2H), 3.55-3.75 (m, 2H), 3.97 (br s, 4H), 4.90 (br s, 1H), 6.94 (s, 1H), 7.05-7.40 (m, 6H), 7.53 (s, 1H), 7.76 (s, 1H).

Example 33

3-chloro-4-(5-chloro-2-methylphenylamino)-5-[4-(4-fluorophenyl)piperidine-1-carbonyl]-1-[(5-methyl-1,3,4-oxadiazol-2-yl)methyl]pyridin-2(1H)-one (compound 187)

Using methyl 4,6-dichloronicotinate (0.33 g, 1.62 mmol), 5-chloro-2-methylaniline and 2-(chloromethyl)-5-methyl-1,3,4-oxadiazole and in the same manner as in Example 30, steps 1, 2 and 3, compound 187 (83 mg, 9.0%) was obtained.

ESIMS m/z: 570 (M+H)+; $^1$H NMR (300 MHz, DMSO-$d_5$, δ): 1.15-1.85 (m, 4H), 1.90-2.30 (m, 1H), 2.20 (s, 3H), 2.48 (s, 3H), 2.60-3.20 (m, 2H), 3.96 (br s, 2H), 5.35 (s, 2H), 7.05-7.40 (m, 7H), 7.80 (s, 1H), 7.99 (s, 1H).

Example 34

3-chloro-4-(1,1-dioxobenzo[b]thiophen-6-ylamino)-5-[4-(4-fluorophenyl)piperidine-1-carbonyl]-1-methylpyridin-2(1H)-one (compound 188)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 6-amino-1,1-dioxobenzo[b]thiophene (57 mg, 0.31 mmol), and in the same manner as in Example 12, step 6, compound 188 (57 mg, 52%) was obtained.

ESIMS m/z: 528 (M+H)+; $^1$H NMR (400 MHz, CDCl$_3$, δ): 1.38-1.47 (m, 2H), 1.79-1.82 (m, 2H), 2.60-2.80 (m, 3H), 3.63 (s, 3H), 3.89-3.98 (m, 2H), 6.69 (d, J=6.9 Hz, 1H), 6.96-7.04 (m, 3H), 7.08-7.14 (m, 3H), 7.19 (d, J=6.9 Hz, 1H), 7.29-7.33 (m, 2H), 7.46 (s, 1H).

Example 35

3-chloro-4-(5-chloro-2-methylphenylamino)-5-[4-(4-fluorophenyl)piperidine-1-carbonyl]-1-propylpyridin-2(1H)-one (compound 189)

Using 3-chloro-4-(5-chloro-2-methylphenylamino)-5-[4-(4-fluorophenyl)piperidine-1-carbonyl]pyridin-2(1H)-one (40 mg, 0.084 mmol) obtained in Example 21, step 5, and 1-bromopropane (0.0090 mL, 0.10 mmol), and in the same manner as in Example 3, step 5, compound 189 (27 mg, 61%) was obtained.

ESIMS m/z: 516 (M+H)+; $^1$H NMR (400 MHz, CDCl$_3$, δ): 0.98 (t, J=7.3 Hz, 3H), 1.38-1.46 (m, 2H), 1.79-1.85 (m, 4H), 2.31 (s, 3H), 2.55-2.72 (m, 3H), 3.93 (t, J=6.8 Hz, 2H), 3.97-4.08 (m, 2H), 6.54 (s, 1H), 6.95-7.01 (m, 3H), 7.05-7.17 (m, 4H), 7.27 (s, 1H).

Example 36

3-chloro-4-(5-chloro-2-methylphenylamino)-5-[4-(4-fluorophenyl)piperidine-1-carbonyl]-1-(2,2,2-trifluoroethyl)pyridin-2(1H)-one (compound 190)

Using 3-chloro-4-(5-chloro-2-methylphenylamino)-5-[4-(4-fluorophenyl)piperidine-1-carbonyl]pyridin-2(1H)-one (40 mg, 0.084 mmol) obtained in Example 21, step 5, and 2,2,2-trifluoroethyl trifluoromethanesulfonate (23 mg, 0.10 mmol), and in the same manner as in Example 3, step 5, compound 190 (32 mg, 68%) was obtained.

ESIMS m/z: 556 (M+H)+; $^1$H NMR (400 MHz, CDCl$_3$, δ): 1.40-1.50 (m, 2H), 1.83-1.86 (m, 2H), 2.32 (s, 3H), 2.64-2.71 (m, 3H), 4.00-4.15 (m, 2H), 4.65 (s, 2H), 6.67 (s, 1H), 6.97-7.02 (m, 3H), 7.11-7.14 (m, 3H), 7.18 (d, J=8.8 Hz, 1H), 7.23 (s, 1H).

Example 37

4-(2-fluoro-4-methoxyphenylamino)-5-[4-(4-fluorophenyl)piperidine-1-carbonyl]-1,3-dimethylpyridin-2(1H)-one (compound 191)

Using 4-chloro-5-[4-(4-fluorophenyl)piperidine-1-carbonyl]-1,3-dimethylpyridin-2(1H)-one (80 mg, 0.22 mmol) obtained in Example 15, step 1, and 2-fluoro-4-methoxyaniline (47 mg, 0.33 mmol), and in the same manner as in Example 12, step 6, compound 191 (53 mg, 51%) was obtained.

ESIMS m/z: 468 (M+H)+; 1H NMR (300 MHz, CDCl3, δ): 1.39-1.50 (m, 2H), 1.77-1.81 (m, 2H), 2.00 (s, 3H), 2.62-2.70 (m, 1H), 2.70-2.91 (m, 2H), 3.55 (s, 3H), 3.77 (s, 3H), 4.09-4.16 (m, 2H), 6.02 (br s, 1H), 6.57-6.60 (m, 1H), 6.67-6.72 (m, 1H), 6.81-6.87 (m, 1H), 6.94-7.00 (m, 2H), 7.05-7.09 (m, 2H), 7.31 (s, 1H).

Example 38

5-[4-(4-fluorophenyl)piperidine-1-carbonyl]-1,3-dimethyl-4-(2,4,5-trifluorophenylamino)pyridin-2 (1H)-one (compound 192)

Using 4-chloro-5-[4-(4-fluorophenyl)piperidine-1-carbonyl]-1,3-dimethylpyridin-2(1H)-one (80 mg, 0.22 mmol) obtained in Example 15, step 1, and 2,4,5-trifluoroaniline (49 mg, 0.33 mmol), and in the same manner as in Example 12, step 6, compound 192 (70 mg, 67%) was obtained.

ESIMS m/z: 474 (M+H)+; 1H NMR (300 MHz, CDCl3, δ): 1.41-1.52 (m, 2H), 1.84-1.87 (m, 2H), 1.97 (s, 3H), 2.68-2.74 (m, 1H), 2.82-2.98 (m, 2H), 3.58 (s, 3H), 4.17-4.30 (m, 2H), 6.52-6.57 (m, 2H), 6.95-7.02 (m, 3H), 7.05-7.08 (m, 2H), 7.34 (s, 1H).

Example 39

4-(benzo[d]thiazol-6-ylamino)-5-[4-(4-fluorophenyl) piperidine-1-carbonyl]-1-methyl-3-nitropyridin-2 (1H)-one (compound 195)

(step 1) Using ethyl 4-hydroxy-1-methyl-6-oxo-1,6-dihydropyridine-3-carboxylate (2 g, 10.1 mmol) obtained in Example 12, step 1, and in the same manner as in Example 12, step 4, 4-hydroxy-1-methyl-6-oxo-1,6-dihydropyridine-3-carboxylic acid (1.63 g, 95%) was obtained.

ESIMS m/z: 170 (M+H)+
(step 2) Using 4-hydroxy-1-methyl-6-oxo-1,6-dihydropyridine-3-carboxylic acid (500 mg, 2.96 mmol) obtained in step 1, and in the same manner as in Example 1, step 4, 5-[4-(4-fluorophenyl)piperidine-1-carbonyl]-4-hydroxy-1-methylpyridin-2(1H)-one (860 mg, 88%) was obtained.

ESIMS m/z: 331 (M+H)+
(step 3) 5-[4-(4-Fluorophenyl)piperidine-1-carbonyl]-4-hydroxy-1-methylpyridin-2(1H)-one (800 mg, 2.42 mmol) obtained in step 2 was dissolved in acetic acid (4 mL) and water (1 mL), concentrated nitric acid (0.43 mL, 9.69 mmol) was added at −10° C., and the mixture was stirred for 1 hr while gradually raising the temperature from −10° C. to room temperature. The reaction mixture was added dropwise to ice water, and the precipitated solid was collected by filtration to give 5-[4-(4-fluorophenyl)piperidine-1-carbonyl]-4-hydroxy-1-methyl-3-nitropyridin-2(1H)-one (755 mg, 83%).

ESIMS m/z: 376 (M+H)'
(step 4) Using 5-[4-(4-fluorophenyl)piperidine-1-carbonyl]-4-hydroxy-1-methyl-3-nitropyridin-2(1H)-one (500 mg, 1.33 mmol) obtained in step 3, and in the same manner as in Example 12, step 2, 4-chloro-5-[4-(4-fluorophenyl)piperidine-1-carbonyl]-1-methyl-3-nitropyridin-2(1H)-one (314 mg, 60%) was obtained.

ESIMS m/z: 394 (M+H)+
(step 5) Using 4-chloro-5-[4-(4-fluorophenyl)piperidine-1-carbonyl]-1-methyl-3-nitropyridin-2(1H)-one (145 mg, 0.368 mmol), and benzo[d]thiazol-6-amine (111 mg, 0.736 mmol) obtained in step 4, and in the same manner as in Example 12, step 6, compound 195 (152 mg, 81%) was obtained.

ESIMS m/z: 508 (M+H)+; 1H NMR (300 MHz, CDCl3, δ): 1.21-1.43 (m, 2H), 1.65-1.78 (m, 2H), 2.50-2.63 (m, 1H), 2.75-3.00 (m, 2H), 3.59 (s, 3H), 3.65-3.78 (m, 2H), 6.91-7.07 (m, 4H), 7.33 (dd, J=8.6, 2.0 Hz, 1H), 7.59 (s, 1H), 7.75 (d, J=2.0 Hz, 1H), 8.13 (d, J=8.6 Hz, 1H), 9.01 (s, 1H), 10.1 (s, 1H).

Example 40

4-(benzo[d]oxazol-5-ylamino)-3-chloro-5-[4-(4-fluorophenyl)piperidine-1-carbonyl]-1-methylpyridin-2(1H)-one (compound 196)

Using 3,4-dichloro-5-[4-(4-fluorophenyl)piperidine-1-carbonyl]-1-methylpyridin-2(1H)-one (80 mg, 0.21 mmol) obtained in Example 12, step 5, and benzo[d]oxazol-5-amine (42 mg, 0.313 mmol), and in the same manner as in Example 12, step 6, compound 196 (9 mg, 9%) was obtained.

ESIMS m/z: 481 (M+H)+; 1H NMR (400 MHz, CDCl3, δ): 1.20-1.50 (m, 2H), 1.60-1.80 (m, 2H), 2.30-2.85 (m, 3H), 3.61 (s, 3H), 3.70-3.90 (m, 2H), 6.80 (s, 1H), 6.94-7.01 (m, 2H), 7.02-7.09 (m, 2H), 7.14 (dd, J=8.8, 2.0 Hz, 1H), 7.42 (s, 1H), 7.50-7.58 (m, 2H), 8.12 (s, 1H).

Example 41

3-amino-4-(benzo[d]thiazol-6-ylamino)-5-[4-(4-fluorophenyl)piperidine-1-carbonyl]-1-methylpyridin-2(1H)-one (compound 197)

Compound 195 (140 mg, 0.276 mmol) was dissolved in ethanol (3 mL), 10% palladium carbon (15 mg, 0.141 mmol) was added, and the mixture was stirred under a hydrogen atmosphere at room temperature for 5 hr. The reaction mixture was filtered through celite, and the solvent was evaporated under reduced pressure. The residue was purified by silica gel column chromatography (chloroform/methanol=99/1-95/5) to give compound 197 (120 mg, 91%).

ESIMS m/z: 478 (M+H)+; 1H NMR (300 MHz, CDCl3, δ): 1.20-1.35 (m, 2H), 1.52-1.73 (m, 2H), 2.50-2.63 (m, 1H), 2.70-2.98 (m, 2H), 3.63 (s, 3H), 4.15-4.50 (m, 2H), 6.47 (s, 1H), 6.60-6.72 (m, 2H), 6.78-6.85 (m, 3H), 6.97 (dd, J=8.8, 2.2 Hz, 1H), 7.06 (d, J=2.2 Hz, 1H), 7.99 (d, J=8.8 Hz, 1H), 8.77 (s, 1H).

Example 42

N-{4-(benzo[d]thiazol-6-ylamino)-5-[4-(4-fluorophenyl)piperidine-1-carbonyl]-1-methyl-2-oxo-1,2-dihydropyridin-3-yl}acetamide (compound 199)

Compound 197 (30 mg, 0.063 mmol) was dissolved in dichloromethane (1 mL), triethylamine (0.010 mL, 0.075 mmol) and acetyl chloride (0.006 mL, 0.075 mmol) were added, and the mixture was stirred at room temperature for 15 hr. To the reaction mixture was added saturated aqueous ammonium chloride solution, and the mixture was extracted with chloroform. The organic layer was dried over anhydrous magnesium sulfate and the solvent was evaporated under reduced pressure, and the residue was purified by silica gel column chromatography (chloroform/methanol=90/10) to give compound 199 (26.1 mg, 80%).

ESIMS m/z: 520 (M+H)+; 1H NMR (400 MHz, CDCl3, δ): 1.40-1.80 (m, 4H), 2.29 (s, 3H), 2.43-2.56 (m, 1H), 2.75-3.00 (m, 2H), 3.62 (s, 3H), 3.70-3.90 (m, 2H), 6.92-7.00 (m, 2H), 7.00-7.07 (m, 2H), 7.10 (dd, J=8.8, 2.0 Hz,

1H), 7.42 (d, J=2.0 Hz, 1H), 7.54 (s, 1H), 7.99 (d, J=8.8 Hz, 1H), 8.11 (s, 1H), 8.28 (s, 1H), 8.82 (s, 1H).

Example 43

1-{4-(benzo[d]thiazol-6-ylamino)-5-[4-(4-fluorophenyl)piperidine-1-carbonyl]-1-methyl-2-oxo-1,2-dihydropyridin-3-yl}-3-ethylurea (compound 200)

Compound 197 (30 mg, 0.063 mmol) was dissolved in dichloromethane (1 mL), triethylamine (0.010 mL, 0.075 mmol) and ethyl isocyanate (0.006 mL, 0.075 mmol) were added, and the mixture was stirred at room temperature for 15 hr. To the reaction mixture was added saturated aqueous ammonium chloride solution, and the mixture was extracted with chloroform. The organic layer was dried over anhydrous magnesium sulfate, the solvent was evaporated under reduced pressure, and the residue was purified by silica gel column chromatography (chloroform/methanol=99/1-95/5) to give compound 200 (34 mg, 99%).

ESIMS m/z: 549 (M+H)$^+$; $^1$H NMR (400 MHz, CDCl$_3$, δ): 1.19 (t, J=7.3 Hz, 3H), 1.50-1.90 (m, 4H), 2.47-2.55 (m, 1H), 2.75-2.95 (m, 2H), 3.28-3.37 (m, 2H), 3.62 (s, 3H), 3.73-3.88 (m, 2H), 6.22 (s, 1H), 6.88-7.12 (m, 5H), 7.39 (s, 1H), 7.50 (s, 1H), 7.92 (s, 1H), 7.98 (d, J=8.8 Hz, 1H), 8.80 (s, 1H), 8.99 (br. s, 1H).

Example 44

3-chloro-1-(2-fluoroethyl)-5-[4-(4-fluorophenyl) piperidine-1-carbonyl]-4-(1-methyl-1H-indazol-6-ylamino)pyridin-2(1H)-one (compound 203)

(step 1) In the same manner as in Example 12, step 1, and using 2-fluoroethylamine hydrochloride (16.4 g, 165 mmol) instead of methylamine, ethyl 1-(2-fluoroethyl)-4-hydroxy-6-oxo-1,6-dihydropyridine-3-carboxylate (13.5 g, 54%) was obtained.

ESIMS m/z: 230 (M+H)$^+$ (step 2) Using ethyl 1-(2-fluoroethyl)-4-hydroxy-6-oxo-1,6-dihydropyridine-3-carboxylate (13.5 g, 58.9 mmol) obtained in step 1, and in the same manner as in Example 12, step 2, ethyl 4-chloro-1-(2-fluoroethyl)-6-oxo-1,6-dihydropyridine-3-carboxylate (3.62 g, 25%) was obtained.

ESIMS m/z: 248 (M+H)$^+$ (step 3) Using ethyl 4-chloro-1-(2-fluoroethyl)-6-oxo-1,6-dihydropyridine-3-carboxylate (1.0 g, 4.04 mmol) obtained in step 2, and in the same manner as in Example 12, step 3, ethyl 4,5-dichloro-1-(2-fluoroethyl)-6-oxo-1,6-dihydropyridine-3-carboxylate (1.1 g, quantitative) was obtained.

ESIMS m/z: 282 (M+H)$^+$ (step 4) Using ethyl 4,5-dichloro-1-(2-fluoroethyl)-6-oxo-1,6-dihydropyridine-3-carboxylate (1.09 g, 3.86 mmol) obtained in step 3, and in the same manner as in Example 12, step 4, 4,5-dichloro-1-(2-fluoroethyl)-6-oxo-1,6-dihydropyridine-3-carboxylic acid (0.82 g, 83%) was obtained.

ESIMS m/z: 254 (M+H)$^+$ (step 5) Using 4,5-dichloro-1-(2-fluoroethyl)-6-oxo-1,6-dihydropyridine-3-carboxylic acid (0.76 g, 3.0 mmol) obtained in step 4, and in the same manner as in Example 1, step 4, 3,4-dichloro-1-(2-fluoroethyl)-5-[4-(4-fluorophenyl) piperidine-1-carbonyl]pyridin-2(1H)-one (1.25 g, quantitative) was obtained.

ESIMS m/z: 415

(step 6) Using 3,4-dichloro-1-(2-fluoroethyl)-5-[4-(4-fluorophenyl)piperidine-1-carbonyl]pyridin-2(1H)-one (80 mg, 0.19 mmol) obtained in step 5, and 1-methyl-1H-indazol-6-amine (43 mg, 0.289 mmol), and in the same manner as in Example 12, step 6, compound 203 (33 mg, 33%) was obtained.

ESIMS m/z: 526 (M+H)$^+$; $^1$H NMR (400 MHz, CDCl$_3$, δ): 1.10-1.45 (m, 2H), 1.50-1.73 (m, 2H), 2.15-2.90 (m, 3H), 3.68-3.85 (m, 2H), 4.03 (s, 3H), 4.20-4.30 (m, 1H), 4.30-4.40 (m, 1H), 4.68 (t, J=4.4 Hz, 1H), 4.84 (t, J=4.4 Hz, 1H), 6.88 (dd, J=8.4, 1.8 Hz, 1H), 6.91-7.05 (m, 5H), 7.06 (br s, 1H), 7.46 (s, 1H), 7.66 (d, J=8.8 Hz, 1H), 7.91 (s, 1H).

Example 45

3-chloro-4-(5-chloro-2-methylphenylamino)-5-[4-(4-fluorophenyl)piperidine-1-carbonyl]-1-(2-hydroxyethoxyl)pyridin-2(1H)-one (compound 204)

(step 1) Using compound 21 (369 mg, 0.636 mmol), and in the same manner as in Example 4, step 3, a crude product (312 mg) of 3-chloro-4-(5-chloro-2-methylphenylamino)-5-[4-(4-fluorophenyl)piperidine-1-carbonyl]-1-hydroxypyridin-2(1H)-one was obtained, which was used for the next step without purification.

(step 2) Using a crude product (20.5 mg from 312 mg) of 3-chloro-4-(5-chloro-2-methylphenylamino)-5-[4-(4-fluorophenyl)piperidine-1-carbonyl]-1-hydroxypyridin-2(1H)-one obtained in step 1, and 2-bromoethanol (0.0059 mL, 0.084 mmol), and in the same manner as in Example 4, step 4, compound 204 (16.4 mg, 2 steps 73%) was obtained.

ESIMS m/z: 534 (M+H)$^+$; $^1$H NMR (400 MHz, CDCl$_3$, δ): 1.37-1.50 (m, 2H), 1.78-1.88 (m, 2H), 2.31 (s, 3H), 2.51-2.80 (m, 3H), 3.77-3.85 (m, 2H), 3.93-4.13 (m, 2H), 4.28-4.40 (m, 3H), 6.60 (br s, 1H), 6.94-7.03 (m, 3H), 7.08-7.15 (m, 3H), 7.18 (d, J=8.8 Hz, 1H), 7.54 (s, 1H).

Example 46

4-(benzo[d]thiazol-5-ylamino)-3-chloro-5-[4-(4-fluorophenyl)piperidine-1-carbonyl]-1-(2-methoxyethyl)pyridin-2(1H)-one (compound 206)

(step 1) Using 2-methoxyethylamine (14.3 mL, 137 mmol) instead of methylamine used in Example 12, step 1, and in the same manner as in Example 12, step 1, ethyl 4-hydroxy-1-(2-methoxyethyl)-6-oxo-1,6-dihydropyridine-3-carboxylate (13 g, 49%) was obtained.

ESIMS m/z: 242 (M+H)$^+$ (step 2) Using ethyl 4-hydroxy-1-(2-methoxyethyl)-6-oxo-1,6-dihydropyridine-3-carboxylate (13 g, 53.9 mmol) obtained in step 1, and in the same manner as in Example 12, step 2, ethyl 4-chloro-1-(2-methoxyethyl)-6-oxo-1,6-dihydropyridine-3-carboxylate (8.2 g, 59%) was obtained.

ESIMS m/z: 260 (M+H)'

(step 3) Using ethyl 4-chloro-1-(2-methoxyethyl)-6-oxo-1,6-dihydropyridine-3-carboxylate (14 g, 48.5 mmol) obtained in step 2, and in the same manner as in Example 12, step 3, ethyl 4,5-dichloro-1-(2-methoxyethyl)-6-oxo-1,6-dihydropyridine-3-carboxylate (5.8 g, 39%) was obtained.

ESIMS m/z: 294 (M+H)$^+$ (step 4) Using ethyl 4,5-dichloro-1-(2-methoxyethyl)-6-oxo-1,6-dihydropyridine-3-carboxylate (1.6 g, 5.4 mmol) obtained in step 3, and in the same manner as in Example 12, step 4, 4,5-dichloro-1-(2-methoxyethyl)-6-oxo-1,6-dihydropyridine-3-carboxylic acid (1.2 g, 86%) was obtained.

ESIMS m/z: 266 (M+H)$^+$ (step 5) Using 4,5-dichloro-1-(2-methoxyethyl)-6-oxo-1,6-dihydropyridine-3-carboxylic acid (0.8 g, 3.0 mmol) obtained in step 4, and in the same manner as in Example 1, step 4, 3,4-dichloro-5-[4-(4-fluorophenyl)piperidine-1-carbonyl]-1-(2-methoxyethyl)pyridin-2(1H)-one (1.25 g, 98%) was obtained.

ESIMS m/z: 427

(step 6) Using 3,4-dichloro-5-[4-(4-fluorophenyl)piperidine-1-carbonyl]-1-(2-methoxyethyl)pyridin-2(1H)-one (70 mg, 0.16 mmol) obtained in step 5, and benzo[d]thiazol-5-amine (37 mg, 0.246 mmol), and in the same manner as in Example 12, step 6, compound 206 (58 mg, 66%) was obtained.

ESIMS m/z: 541 (M+H)$^+$; $^1$H NMR (400 MHz, CDCl$_3$, δ): 1.20-1.55 (m, 2H), 1.60-1.80 (m, 2H), 2.20-2.90 (m, 3H), 3.32 (s, 3H), 3.65-3.75 (m, 2H), 3.90-4.05 (m, 2H), 4.10-4.30 (m, 2H), 6.93-7.00 (m, 2H), 7.02-7.12 (m, 3H), 7.23 (d, J=6.8 Hz, 1H), 7.42 (s, 1H), 7.76 (s, 1H), 7.89 (d, J=7.8 Hz, 1H), 9.01 (s, 1H).

Example 47

4-(benzo[d]thiazol-5-ylamino)-5-[4-(4-fluorophenyl)piperidine-1-carbonyl]-1,3-dimethylpyridin-2(1H)-one (compound 208)

Using 4-chloro-5-[4-(4-fluorophenyl)piperidine-1-carbonyl]-1,3-dimethylpyridin-2(1H)-one (80 mg, 0.22 mmol) obtained in Example 15, step 1, and benzo[d]thiazol-5-amine (50 mg, 0.33 mmol), and in the same manner as in Example 12, step 6, compound 208 (3.5 mg, 3%) was obtained.

ESIMS m/z: 477 (M+H)$^+$; $^1$H NMR (400 MHz, CDCl$_3$, δ): 1.20-1.45 (m, 2H), 1.65-1.80 (m, 2H), 2.00 (s, 3H), 2.55-2.67 (m, 1H), 2.70-2.90 (m, 2H), 3.59 (s, 3H), 4.14-4.35 (m, 2H), 6.65-6.95 (m, 5H), 6.99-7.04 (m, 1H), 7.33 (s, 1H), 7.49 (s, 1H), 7.81 (d, J 15=8.8 Hz, 1H), 8.98 (s, 1H).

Example 48

3-chloro-4-(4,6-dimethylpyridin-3-ylamino)-5-[4-(4-fluorophenyl)piperidine-1-carbonyl]-1-methylpyridin-2(1H)-one (compound 209)

Using 3,4-dichloro-5-[4-(4-fluorophenyl)piperidine-1-carbonyl]-1-methylpyridin-2(1H)-one (80 mg, 0.21 mmol) obtained in Example 12, step 5, and 4,6-dimethylpyridin-3-amine (38 mg, 0.313 mmol), and in the same manner as in Example 12, step 6, compound 209 (55 mg, 56%) was obtained.

ESIMS m/z: 469 (M+H)$^+$; $^1$H NMR (400 MHz, CDCl$_3$, δ): 1.30-1.60 (m, 2H), 1.70-1.90 (m, 2H), 2.29 (s, 3H), 2.50 (s, 3H), 2.51-2.95 (m, 2H), 2.60-2.70 (m, 1H), 3.57 (s, 3H), 3.85-4.15 (m, 2H), 6.39 (s, 1H), 6.95-7.06 (m, 3H), 7.10-7.20 (m, 3H), 8.12 (s, 1H).

Example 49

3-chloro-4-(5-chloro-2-methylphenylamino)-1-(dimethylamino)-5-[4-(4-fluorophenyl)piperidine-1-carbonyl]pyridin-2(1H)-one (compound 217)

(step 1) To diethyl 3-oxopentandioate (5.0 mL, 27.4 mmol) were added triethyl orthoformate (4.57 mL, 27.4 mmol) and acetic anhydride (5.18 mL, 54.8 mmol), and the mixture was stirred at 135° C. for 2 hr. The reaction mixture was cooled to room temperature, and concentrated under reduced pressure. The residue (6.90 g from 7.86 g) was dissolved in THF (100 mL), N,N-dimethylhydrazine (2.2 mL, 28.9 mmol) was added, and the mixture was stirred at room temperature for 2 hr. The solvent was evaporated under reduced pressure, and the residue was dissolved in toluene (100 mL). DBU (10.9 mL, 72.3 mmol) was added, and the mixture was stirred at 50° C. for 30 min. The reaction mixture was cooled to room temperature, and the mixture was extracted with 0.1 mol/L hydrochloric acid, and the aqueous layer was washed with ethyl acetate. The aqueous layer was neutralized with 1 mol/L aqueous sodium hydroxide solution and extracted with ethyl acetate. The organic layer was washed with saturated brine, and dried over anhydrous magnesium sulfate. The solvent was evaporated under reduced pressure. The residue was purified by silica gel column chromatography (heptane/ethyl acetate=60/40-30/70) to give ethyl 1-(dimethylamino)-4-hydroxy-6-oxo-1,6-dihydropyridine-3-carboxylate (3.41 g, 63%).

ESIMS m/z: 227 (M+H)$^+$ (step 2) Using ethyl 1-(dimethylamino)-4-hydroxy-6-oxo-1,6-dihydropyridine-3-carboxylate (1.03 g, 4.55 mmol) obtained in step 1, and in the same manner as in Example 2, step 2, ethyl 1-(dimethylamino)-6-oxo-4-(trifluoromethylsulfonyloxy)-1,6-dihydropyridine-3-carboxylate (45.5 mg, 48%) was obtained.

ESIMS m/z: 359 (M+H)$^+$ (step 3) Using ethyl 1-(dimethylamino)-6-oxo-4-(trifluoromethylsulfonyloxy)-1,6-dihydropyridine-3-carboxylate (173 mg, 0.483 mmol) obtained in step 2, and in the same manner as in Example 2, step 3, ethyl 4-(5-chloro-2-methylphenylamino)-1-(dimethylamino)-6-oxo-1,6-dihydropyridine-3-carboxylate (125 mg, 74%) was obtained.

ESIMS m/z: 350 (M+H)$^+$ (step 4) Using ethyl 4-(5-chloro-2-methylphenylamino)-1-(dimethylamino)-6-oxo-1,6-dihydropyridine-3-carboxylate (123 mg, 0.352 mmol) obtained in step 3, and in the same manner as in Example 1, step 6, 4-(5-chloro-2-methylphenylamino)-1-(dimethylamino)-6-oxo-1,6-dihydropyridine-3-carboxylic acid (104 mg, 92%) was obtained.

ESIMS m/z: 322 (M+H)$^+$ (step 5) Using 4-(5-chloro-2-methylphenylamino)-1-(dimethylamino)-6-oxo-1,6-dihydropyridine-3-carboxylic acid (100 mg, 0.311 mmol) obtained in step 4, and in the same manner as in Example 1, step 4 and Example 21, step 3, compound 217 (115 mg, 72%) was obtained.

ESIMS m/z: 517 (M+H)$^+$; $^1$H NMR (400 MHz, CDCl$_3$, δ): 1.41-1.60 (m, 2H), 1.78-1.90 (m, 2H), 2.31 (s, 3H), 2.58-2.86 (m, 3H), 3.08 (s, 6H), 4.01-4.19 (m, 2H), 6.57 (br s, 1H), 6.92 (d, J=2.0 Hz, 1H), 6.96-7.03 (m, 2H), 7.06 (d, J=7.8 Hz, 1H), 7.09-7.18 (m, 3H), 7.43 (s, 1H).

Example 50

4-(benzylamino)-3-chloro-5-[4-(4-fluorophenyl)piperidine-1-carbonyl]-1-methoxypyridin-2(1H)-one (compound 220)

(step 1) Ethyl 1-(benzyloxy)-6-oxo-4-(trifluoromethylsulfonyloxy)-1,6-dihydropyridine-3-carboxylate (635 mg, 1.51 mmol) obtained in Example 2, step 2, benzylamine (0.198 mL, 1.81 mmol), and N,N-diisopropylethylamine (0.526 mL, 3.01 mmol) were dissolved in acetonitrile (10 mL), and the mixture was stirred at 60° C. for 2 hr. The reaction mixture was cooled to room temperature, and concentrated under reduced pressure. The residue was purified by silica gel column chromatography (heptane/ethyl acetate=75/25-

45/55) to give ethyl 4-(benzylamino)-1-(benzyloxy)-6-oxo-1,6-dihydropyridine-3-carboxylate (560 mg, 98%).

ESIMS m/z: 379 (M+H)$^+$ (step 2) Using ethyl 4-(benzylamino)-1-(benzyloxy)-6-oxo-1,6-dihydropyridine-3-carboxylate (300 mg, 0.793 mmol) obtained in step 1, and in the same manner as in Example 21, step 3, ethyl 4-(benzylamino)-1-(benzyloxy)-5-chloro-6-oxo-1,6-dihydropyridine-3-carboxylate (329 mg, quantitative) was obtained.

ESIMS m/z: 413 (M+H)$^+$ (step 3) Using ethyl 4-(benzylamino)-1-(benzyloxy)-5-chloro-6-oxo-1,6-dihydropyridine-3-carboxylate (325 mg, 0.787 mmol) obtained in step 2, and in the same manner as in Example 1, step 6, 4-(benzylamino)-1-(benzyloxy)-5-chloro-6-oxo-1,6-dihydropyridine-3-carboxylic acid (257, 85%) was obtained.

ESIMS m/z: 385 (M+H)$^+$ (step 4) Using 4-(benzylamino)-1-(benzyloxy)-5-chloro-6-oxo-1,6-dihydropyridine-3-carboxylic acid (250 mg, 0.650 mmol) obtained in step 3, and in the same manner as in Example 1, step 4, 4-(benzylamino)-1-(benzyloxy)-3-chloro-5-[4-(4-fluorophenyl)piperidine-1-carbonyl]pyridin-2(1H)-one (359 mg, quantitative) was obtained.

ESIMS m/z: 546 (M+H)$^+$ (step 5) Using 4-(benzylamino)-1-(benzyloxy)-3-chloro-5-[4-(4-fluorophenyl)piperidine-1-carbonyl]pyridin-2(1H)-one (26.4 mg, 0.048 mmol) obtained in step 4, and in the same manner as in Example 4, steps 3 and 4, compound 220 (11.0 mg, 49%) was obtained.

ESIMS m/z: 470 (M+H)$^+$; $^1$H NMR (400 MHz, CDCl$_3$, δ): 1.43-1.63 (m, 2H), 1.81-1.93 (m, 2H), 2.58-2.94 (m, 3H), 4.09 (s, 3H), 4.44-4.56 (m, 2H), 5.27-5.37 (m, 2H), 6.96-7.41 (m, 10H), 7.44 (s, 1H).

Example 51

4-(benzylamino)-5-[4-(4-fluorophenyl)piperidine-1-carbonyl]-1-methyl-2-oxo-1,2-dihydropyridine-3-carbonitrile (compound 221)

(step 1) Using ethyl 4-chloro-1-methyl-6-oxo-1,6-dihydropyridine-3-carboxylate (250 mg, 1.16 mmol) obtained in Example 12, step 2, and benzylamine (0.19 mL, 1.74 mmol), and in the same manner as in Example 12, step 6, ethyl 4-(benzylamino)-1-methyl-6-oxo-1,6-dihydropyridine-3-carboxylate (279 mg, 84%) was obtained.

ESIMS m/z: 287 (M+H)$^+$ (step 2) To DMF (3 mL) was added phosphorus oxychloride (765 mL, 8.21 mmol) at 0° C., and the mixture was stirred at 0° C. for 1 hr. Ethyl 4-(benzylamino)-1-methyl-6-oxo-1,6-dihydropyridine-3-carboxylate (470 mg, 1.64 mmol) obtained in step 1 was added, and the mixture was stirred at room temperature for 3 hr. To the reaction mixture was added water, and the mixture was extracted with ethyl acetate. The organic layer was washed with saturated brine and dried over anhydrous sodium sulfate, and the solvent was evaporated under reduced pressure to give ethyl 4-(benzylamino)-5-formyl-1-methyl-6-oxo-1,6-dihydropyridine-3-carboxylate (516 mg, quantitative).

ESIMS m/z: 315 (M+H)$^+$ (step 3) To ethyl 4-(benzylamino)-5-formyl-1-methyl-6-oxo-1,6-dihydropyridine-3-carboxylate (124 mg, 0.394 mmol) obtained in step 2 were added acetic acid (3 mL) and 50% aqueous hydroxylamine solution (0.076 mL, 0.592 mmol), and the mixture was stirred at 120° C. for 4 hr. The reaction mixture was cooled to room temperature, saturated aqueous sodium hydrogen carbonate solution was added, and the mixture was extracted with ethyl acetate. The organic layer was washed with saturated brine and dried over anhydrous sodium sulfate, and the solvent was evaporated under reduced pressure to give ethyl 4-(benzylamino)-5-cyano-1-methyl-6-oxo-1,6-dihydropyridine-3-carboxylate (110 mg, 90%).

ESIMS m/z: 312 (M+H)$^+$ (step 4) Using ethyl 4-(benzylamino)-5-cyano-1-methyl-6-oxo-1,6-dihydropyridine-3-carboxylate (110 mg, 0.353 mmol) obtained in step 3, and in the same manner as in Example 12, step 4, 4-(benzylamino)-5-cyano-1-methyl-6-oxo-1,6-dihydropyridine-3-carboxylic acid (78 mg, 78%) was obtained.

ESIMS m/z: 284 (M+H)$^+$ (step 5) Using 4-(benzylamino)-5-cyano-1-methyl-6-oxo-1,6-dihydropyridine-3-carboxylic acid (78 mg, 0.251 mmol) obtained in step 4, and in the same manner as in Example 1, step 4, compound 221 (99 mg, 89%) was obtained.

ESIMS m/z: 445 (M+H)$^+$; $^1$H NMR (300 MHz, CDCl$_3$, δ): 1.44-1.60 (m, 2H), 1.86-1.96 (m, 2H), 2.70-2.80 (m, 1H), 2.92-3.04 (m, 2H), 3.47 (s, 3H), 4.23-4.33 (m, 2H), 4.93 (d, J=5.5 Hz, 2H), 6.82-6.88 (m, 1H), 6.95-7.03 (m, 2H), 7.06-7.11 (m, 2H), 7.29 (s, 1H), 7.31-7.41 (m, 5H).

Example 52

3-fluoro-5-[4-(4-fluorophenyl)piperidine-1-carbonyl]-1-methyl-4-(1-methyl-1H-indazol-6-ylamino)pyridin-2(1H)-one (compound 224)

(step 1) 4-Chloro-5,6-difluoropyridine-3-carboxylic acid (3 g, 15.5 mmol), and 1-methyl-1H-indazol-6-amine (2.39 g, 15.8 mmol) were dissolved in THF (80 mL), 1.0 mol/L lithiumbis(trimethylsilyl)amide/THF solution (37.5 mL, 37.5 mmol) was added dropwise at −78° C., and the mixture was stirred at −78° C. for 1 hr. The solvent of the reaction mixture was evaporated under reduced pressure, and the residue was adjusted to pH=3 by adding 4.0 mol/L aqueous hydrochloric acid solution. The precipitated solid was collected by filtration to give 5,6-difluoro-4-(1-methyl-1H-indazol-6-ylamino)nicotinic acid (2.98 g, 63%).

ESIMS m/z: 305 (M+H)$^+$ (step 2) 5,6-Difluoro-4-(1-methyl-1H-indazol-6-ylamino)nicotinic acid (2.98 g, 9.79 mmol) obtained in step 1 was dissolved in methanol (50 mL) and THF (5 mL), trimethylsilyldiazomethane (24.5 mL, 49 mmol) was added dropwise at 0° C., and the mixture was stirred at room temperature for 4 hr. To the reaction mixture was added acetic acid, and the precipitated solid was collected by filtration to give methyl 5,6-difluoro-4-(1-methyl-1H-indazol-6-ylamino)nicotinate (3.12 g, quantitative).

ESIMS m/z: 319 (M+H)$^+$ (step 3) Using methyl 5,6-difluoro-4-(1-methyl-1H-indazol-6-ylamino)nicotinate (3.12 g, 9.8 mmol) obtained in step 2, and in the same manner as in Example 1, step 2, methyl 5-fluoro-4-(1-methyl-1H-indazol-6-ylamino)-6-oxo-1,6-dihydropyridine-3-carboxylate (1.31 g, 42%) was obtained.

ESIMS m/z: 317 (M+H)$^+$ (step 4) Using methyl 5-fluoro-4-(1-methyl-1H-indazol-6-ylamino)-6-oxo-1,6-dihydropyridine-3-carboxylate (1.11 g, 3.51 mmol) obtained in step 3, and in the same manner as in Example 1, step 3, 5-fluoro-4-(1-methyl-1H-indazol-6-ylamino)-6-oxo-1,6-dihydropyridine-3-carboxylic acid (1.06 g, quantitative) was obtained.

ESIMS m/z: 303 (M+H)$^+$ (step 5) Using 5-fluoro-4-(1-methyl-1H-indazol-6-ylamino)-6-oxo-1,6-dihydropyridine-3-carboxylic acid (1.06 g, 3.51 mmol) obtained in step 4, and in the same manner as in Example 1, step 4, 3-fluoro-5-[4-(4-fluorophenyl)piperidine-1-carbonyl]-4-(1-methyl-1H-indazol-6-ylamino)pyridin-2(1H)-one (500 mg, 31%) was obtained.

ESIMS m/z: 464 (M+H)$^+$ (step 6) 3-Fluoro-5-[4-(4-fluorophenyl)piperidine-1-carbonyl]-4-(1-methyl-1H-indazol-6-ylamino)pyridin-2(1H)-one (250 mg, 0.54 mmol) obtained in step 5 was dissolved in DMF (3 mL), dimethyl sulfate (0.19 mL, 2.7 mmol) and cesium carbonate (352 mg, 1.08 mmol) were added, and the mixture was stirred at 90° C. for 3 hr. The solvent of the reaction mixture was evaporated under reduced pressure, and the residue was subjected to preparative HPLC (XBridge™ manufactured by Waters) (MeCN/10 mmol/L aqueous ammonium hydrogen carbonate solution) to give compound 224 (39.6 mg, 15%).

ESIMS m/z: 478 (M+H)$^+$; $^1$H NMR (300 MHz, DMSO-$d_6$, δ): 1.12-1.70 (m, 4H), 2.20-2.55 (m, 1H), 2.56-2.97 (m, 2H), 3.49 (s, 3H), 3.89-4.12 (m, 5H), 6.87-6.89 (m, 1H), 6.99-7.15 (m, 5H), 7.57-7.62 (m, 2H), 7.90 (s, 1H), 8.52 (s, 1H).

Example 53

4-(benzo[d]thiazol-6-ylamino)-3-fluoro-5-[4-(4-fluorophenyl)piperidine-1-carbonyl]-1-methylpyridin-2(1H)-one (compound 225)

(step 1) Using 4-chloro-5,6-difluoropyridine-3-carboxylic acid (3 g, 15.5 mmol), and benzo[d]thiazol-6-amine (2.45 g, 16.3 mmol), and in the same manner as in Example 12, step 6, 4-(benzo[d]thiazol-6-ylamino)-5,6-difluoronicotinic acid (4.4 g, 92%) was obtained.

ESIMS m/z: 308 (M+H)$^+$ (step 2) Using 4-(benzo[d]thiazol-6-ylamino)-5,6-difluoronicotinic acid (4.4 g, 14.3 mmol) obtained in step 1, and in the same manner as in Example 52, step 2, methyl 4-(benzo[d]thiazol-6-ylamino)-5-fluoro-6-methoxynicotinate (2.42 g, 51%) was obtained.

ESIMS m/z: 334 (M+H)$^+$ (step 3) Methyl 4-(benzo[d]thiazol-6-ylamino)-5-fluoro-6-methoxynicotinate (2.42 g, 7.26 mmol) obtained in step 2 was dissolved in 1,4-dioxane (30 mL), concentrated hydrochloric acid (30 mL), and the mixture was stirred at 100° C. for 18 hr. The solvent of the reaction mixture was evaporated under reduced pressure and the precipitated solid was collected by filtration to give 4-(benzo[d]thiazol-6-ylamino)-5-fluoro-6-oxo-1,6-dihydropyridine-3-carboxylic acid (2.18 g, 98%).

ESIMS m/z: 306 (M+H)$^+$ (step 4) Using 4-(benzo[d]thiazol-6-ylamino)-5-fluoro-6-oxo-1,6-dihydropyridine-3-carboxylic acid (1.88 g, 6.16 mmol) obtained in step 3, and in the same manner as in Example 1, step 4, 4-(benzo[d]thiazol-6-ylamino)-3-fluoro-5-[4-(4-fluorophenyl)piperidine-1-carbonyl]pyridin-2(1H)-one (820 mg, 29%) was obtained.

ESIMS m/z: 467 (M+H)$^+$ (step 5) Using 4-(benzo[d]thiazol-6-ylamino)-3-fluoro-5-[4-(4-fluorophenyl)piperidine-1-carbonyl]pyridin-2(1H)-one (100 mg, 0.21 mmol) obtained in step 4, and in the same manner as in Example 52, step 6, compound 225 (71 mg, 69%) was obtained. ESIMS m/z: 481 (M+H)$^+$; $^1$H NMR (300 MHz, DMSO-$d_5$, δ): 1.08-1.49 (m, 2H), 1.58-1.62 (m, 2H), 2.18-2.49 (m, 1H), 2.56-2.75 (m, 1H), 2.76-3.31 (m, 1H), 3.49 (s, 3H), 3.71-4.29 (m, 2H), 7.02-7.22 (m, 5H), 7.61 (s, 1H), 7.71 (s, 1H), 7.94 (d, J=8.7 Hz, 1H), 8.56 (s, 1H), 9.18 (s, 1H).

Example 54

4-(benzo[d]thiazol-5-ylamino)-3-chloro-5-[4-(4-fluorophenyl)piperidine-1-carbonyl]-1-(2-methoxyethoxyl)pyridin-2(1H)-one (compound 228)

(step 1) Using ethyl 1-(benzyloxy)-6-oxo-4-(trifluoromethylsulfonyloxy)-1,6-dihydropyridine-3-carboxylate (300 mg, 0.712 mmol) obtained in Example 2, step 2, and benzo[d]thiazol-5-amine (160 mg, 1.07 mmol), and in the same manner as in Example 2, step 3, ethyl 4-(benzo[d]thiazol-5-ylamino)-1-(benzyloxy)-6-oxo-1,6-dihydropyridine-3-carboxylate (285 mg, 95%) was obtained.

ESIMS m/z: 422 (M+H)$^+$ (step 2) Using ethyl 4-(benzo[d]thiazol-5-ylamino)-1-(benzyloxy)-6-oxo-1,6-dihydropyridine-3-carboxylate (260 mg, 0.617 mmol) obtained in step 1, and in the same manner as in Example 12, step 4, 4-(benzo[d]thiazol-5-ylamino)-1-(benzyloxy)-6-oxo-1,6-dihydropyridine-3-carboxylic acid (226 mg, 93%) was obtained.

ESIMS m/z: 394 (M+H)$^+$ (step 3) Using 4-(benzo[d]thiazol-5-ylamino)-1-(benzyloxy)-6-oxo-1,6-dihydropyridine-3-carboxylic acid (220 mg, 0.559 mmol) obtained in step 2, and in the same manner as in Example 1, step 4, 4-(benzo[d]thiazol-5-ylamino)-1-(benzyloxy)-5-[4-(4-fluorophenyl)piperidine-1-carbonyl]pyridin-2(1H)-one (310 mg, quantitative) was obtained.

ESIMS m/z: 555 (M+H)$^+$ (step 4) 4-(Benzo[d]thiazol-5-ylamino)-1-(benzyloxy)-5-[4-(4-fluorophenyl)piperidine-1-carbonyl]pyridin-2(1H)-one (270 mg, 0.487 mmol) obtained in step 3 was dissolved in acetic acid (2 mL) and concentrated hydrochloric acid (2 mL), and the mixture was stirred at 70° C. for 8 hr. The reaction mixture was cooled to room temperature, water was added, and the mixture was extracted with ethyl acetate. The organic layer was washed with saturated brine, and dried over anhydrous magnesium sulfate. The solvent was evaporated under reduced pressure to give 4-(benzo[d]thiazol-5-ylamino)-5-[4-(4-fluorophenyl)piperidine-1-carbonyl]-1-hydroxypyridin-2(1H)-one (126 mg, 56%).

ESIMS m/z: 465 (M+H)$^+$ (step 5) Using 4-(benzo[d]thiazol-5-ylamino)-5-[4-(4-fluorophenyl)piperidine-1-carbonyl]-1-hydroxypyridin-2(1H)-one (16 mg, 0.034 mmol) obtained in step 4, and 1-bromo-2-methoxyethane (0.0065 mL, 0.069 mmol), and in the same manner as in Example 3, step 5, 4-(benzo[d]thiazol-5-ylamino)-5-[4-(4-fluorophenyl)piperidine-1-carbonyl]-1-(2-methoxyethoxy)pyridin-2(1H)-one (13.5 mg, 75%) was obtained. ESIMS m/z: 523 (M+H)$^+$ (step 6) Using 4-(benzo[d]thiazol-5-ylamino)-5-[4-(4-fluorophenyl)piperidine-1-carbonyl]-1-(2-methoxyethoxy)pyridin-2(1H)-one (13.5 mg, 0.026 mmol) obtained in step 5, and in the same manner as in Example 21, step 3, compound 228 (6 mg, 42%) was obtained.

ESIMS m/z: 557 (M+H)$^+$; $^1$H NMR (300 MHz, CDCl$_3$, δ): 1.25-1.35 (m, 2H), 1.60-1.75 (m, 4H), 2.50-2.59 (m, 1H), 3.41 (s, 3H), 3.71 (t, J=4.4 Hz, 2H), 3.82-3.94 (m, 2H), 4.51 (t, J=4.4 Hz, 2H), 6.91-7.06 (m, 5H), 7.22 (dd, J=8.8, 2.2 Hz, 1H), 7.69 (s, 1H), 7.79 (d, J=2.2 Hz, 1H), 7.91 (d, J=8.8 Hz, 1H), 9.03 (s, 1H).

Example 55

5-[4-(4-fluorophenyl)piperidine-1-carbonyl]-1-(2-hydroxyethoxy)-3-methyl-4-(m-tolylamino)pyridin-2(1H)-one (compound 229)

(step 1) To diethyl 2-methyl-3-oxopentanedioate (100 g, 462 mmol) were added triethyl orthoformate (75.4 g, 509 mmol) and acetic anhydride (70.8 g, 694 mmol), and the mixture was stirred at 130° C. for 3 hr. The reaction mixture was cooled to room temperature, and concentrated under reduced pressure. The residue was dissolved in DMF (100 mL), O-benzylhydroxylamine (109.8 g, 695 mmol) and triethylamine (70.2 g, 695 mmol) were added at 0° C., and the mixture was stirred at room temperature for 1 hr. To the reaction mixture was added water, and the mixture was extracted with ethyl acetate. The organic layer was washed with water and saturated brine, and dried over anhydrous magnesium sulfate. The solvent was evaporated under reduced pressure. 25 g from 70 g of the obtained residue was dissolved in toluene (200 mL), DBU (16.3 g, 107 mmol) was added, and the mixture was heated under reflux for 1 hr. The reaction mixture was cooled to room temperature, 0.1 mol/L hydrochloric acid was added, and the mixture was extracted with ethyl acetate. The organic layer was washed with water and saturated brine, and dried over anhydrous magnesium sulfate. The solvent was evaporated under reduced pressure to give ethyl 1-(benzyloxy)-4-hydroxy-5-methyl-6-oxo-1,6-dihydropyridine-3-carboxylate (20 g, 40%).

ESIMS m/z: 304 (M+H)$^+$ (step 2) Using ethyl 1-(benzyloxy)-4-hydroxy-5-methyl-6-oxo-1,6-dihydropyridine-3-carboxylate (30 g, 98.9 mmol) obtained in step 1, and in the same manner as in Example 1, step 6, 1-(benzyloxy)-4-hydroxy-5-methyl-6-oxo-1,6-dihydropyridine-3-carboxylic acid (20 g, quantitative) was obtained.

ESIMS m/z: 276 (M+H)$^+$ (step 3) Using 1-(benzyloxy)-4-hydroxy-5-methyl-6-oxo-1,6-dihydropyridine-3-carboxylic acid (20 g, 98.9 mmol) obtained in step 2, and in the same manner as in Example 1, step 4, 1-(benzyloxy)-5-[4-(4-fluorophenyl)piperidine-1-carbonyl]-4-hydroxy-3-methylpyridin-2(1H)-one (25 g, 79%) was obtained. ESIMS m/z: 437 (M+H)$^+$ (step 4) Using 1-(benzyloxy)-5-[4-(4-fluorophenyl)piperidine-1-carbonyl]-4-hydroxy-3-methylpyridin-2(1H)-one (27 g, 61.9 mmol) obtained in step 3, and in the same manner as in Example 2, step 2, 1-(benzyloxy)-5-[4-(4-fluorophenyl)piperidine-1-carbonyl]-3-methyl-2-oxo-1,2-dihydropyridin-4-yl trifluoromethanesulfonate (22 g, 63%) was obtained.

ESIMS m/z: 569 (M+H)$^+$ (step 5) Using 1-(benzyloxy)-5-[4-(4-fluorophenyl)piperidine-1-carbonyl]-3-methyl-2-oxo-1,2-dihydropyridin-4-yl trifluoromethanesulfonate (1.5 g, 2.64 mmol) obtained in step 4, and 3-methylaniline (0.394 g, 3.68 mmol), and in the same manner as in Example 2, step 3, 1-(benzyloxy)-5-[4-(4-fluorophenyl)piperidine-1-carbonyl]-3-methyl-4-(m-tolylamino)pyridin-2(1H)-one (0.18 g, 13%) was obtained.

ESIMS m/z: 526 (M+H)$^+$ (step 6) Using 1-(benzyloxy)-5-[4-(4-fluorophenyl)piperidine-1-carbonyl]-3-methyl-4-(m-tolylamino)pyridin-2(1H)-one (0.35 g, 0.67 mmol) obtained in step 5, and in the same manner as in Example 4, step 3, 5-[4-(4-fluorophenyl)piperidine-1-carbonyl]-1-hydroxy-3-methyl-4-(m-tolylamino)pyridin-2(1H)-one (0.16 g, 55%) was obtained.

ESIMS m/z: 436 (M+H)$^+$ (step 7) Using 5-[4-(4-fluorophenyl)piperidine-1-carbonyl]-1-hydroxy-3-methyl-4-(m-tolylamino)pyridin-2(1H)-one (80 mg, 0.18 mmol) obtained in step 6, and 2-bromoethan-1-ol (46 mg, 0.37 mmol), and in the same manner as in Example 4, step 4, 5-[4-(4-fluorophenyl)piperidine-1-carbonyl]-1-(2-hydroxyethoxy)-3-methyl-4-(m-tolylamino)pyridin-2(1H)-one (25 mg, 29%) was obtained.

ESIMS m/z: 480 (M+H)$^+$; $^1$H NMR (300 MHz, DMSO-d$_5$, δ): 1.21-1.48 (m, 2H), 1.53-1.66 (m, 2H), 1.89 (s, 3H), 2.22 (s, 3H), 2.55-3.23 (m, 3H), 3.54-4.30 (m, 6H), 4.92-5.11 (m, 1H), 6.57-6.72 (m, 3H), 7.01-7.20 (m, 5H), 7.78 (s, 1H), 7.89 (s, 1H).

Example 56

The following compounds were synthesized based on Example 3.

2-{4-(2,5-dichlorophenylamino)-5-[4-(4-fluorophenyl)piperidine-1-carbonyl]-2-oxopyridin-1(2H)-yl}-N-(ethylsulfonyl)acetamide (compound 1); ESIMS m/z: 609 (M+H)$^+$ 2-{4-(2-chloro-5-methylphenylamino)-5-[4-(4-fluorophenyl)piperidine-1-carbonyl]-2-oxopyridin-1(2H)-yl}-N-(ethylsulfonyl)acetamide (compound 2); ESIMS m/z: 589 (M+H)$^+$ 4-(2-chloro-5-methylphenylamino)-1-(difluoromethyl)-5-[4-(4-fluorophenyl)piperidine-1-carbonyl]pyridin-2(1H)-one (compound 4); ESIMS m/z: 490 (M+H)$^+$ 2-{4-(2-chloro-5-methylphenylamino)-5-[4-(4-fluorophenyl)piperidine-1-carbonyl]-2-oxopyridin-1(2H)-yl}acetonitrile (compound 5); ESIMS m/z: 479 (M+H)$^+$ 4-(2-chloro-5-methylphenylamino)-5-[4-(4-fluorophenyl)piperidine-1-carbonyl]-1-(3-methoxypropyl)pyridin-2(1H)-one (compound 6); ESIMS m/z: 512 (M+H)$^+$ 4-(2-chloro-5-methylphenylamino)-1-(cyclopropylmethyl)-5-[4-(4-fluorophenyl)piperidine-1-carbonyl]pyridin-2(1H)-one (compound 7); ESIMS m/z: 494 (M+H)$^+$ 4-(2-chloro-5-methylphenylamino)-1-(cyclobutylmethyl)-5-[4-(4-fluorophenyl)piperidine-1-carbonyl]pyridin-2(1H)-one (compound 8); ESIMS m/z: 508 (M+H)$^+$ methyl 2-({4-(2-chloro-5-methylphenylamino)-5-[4-(4-fluorophenyl)piperidine-1-carbonyl]-2-oxopyridin-1(2H)-yl}methyl)oxazole-4-carboxylate (compound 9); ESIMS m/z: 579 (M+H)$^+$ 4-(2-chloro-5-methylphenylamino)-1-[(3,5-dimethylisoxazol-4-yl)methyl]-5-[4-(4-fluorophenyl)piperidine-1-carbonyl]pyridin-2(1H)-one (compound 10); ESIMS m/z: 549 (M+H)$^+$ 4-(2-chloro-5-methylphenylamino)-1-(3,3-dimethoxypropyl)-5-[4-(4-fluorophenyl)piperidine-1-carbonyl]pyridin-2(1H)-one (compound 11); ESIMS m/z: 542 (M+H)$^+$ 3-({4-(2-chloro-5-methylphenylamino)-5-[4-(4-fluorophenyl)piperidine-1-carbonyl]-2-oxopyridin-1(2H)-yl}methyl)-1,2,4-oxadiazol-5(4H)-one (compound 12); ESIMS m/z: 538 (M+H)$^+$ (Z)-2-{4-(2-chloro-5-methylphenylamino)-5-[4-(4-fluorophenyl)piperidine-1-carbonyl]-2-oxopyridin-1(2H)-yl}-N'-hydroxyacetimidamide (compound 13); ESIMS m/z: 512 (M+H)$^+$ 1-[(5-tert-butyl-1,2,4-oxadiazol-3-yl)methyl]-4-(2-chloro-5-methylphenylamino)-5-[4-(4-fluorophenyl)piperidine-1-carbonyl]pyridin-2(1H)-one (compound 14); ESIMS m/z: 578 (M+H)$^+$ 4-(2-chloro-5-methylphenylamino)-5-[4-(4-fluorophenyl)piperidine-1-carbonyl]-1-[(5-methylisoxazol-3-yl)methyl]pyridin-2(1H)-one (compound 15); ESIMS m/z: 535 (M+H)$^+$ 4-(2-chloro-5-methylphenylamino)-5-[4-(4-fluorophenyl)piperidine-1-carbonyl]-1-[(5-thioxo-4,5-dihydro-1,2,4-oxadiazol-3-yl)methyl]pyridin-2(1H)-one (compound 16); ESIMS m/z: 554 (M+H)$^+$ 4-(2-chloro-5-methylphenylamino)-5-[4-(4-fluorophenyl)piperidine-1-carbonyl]-1-(2-morpholinoethyl)pyridin-2(1H)-one (compound 17); ESIMS m/z: 553 (M+H)$^+$ 4-(2-chloro-5-methylphenylamino)-5-[4-(4-fluorophenyl)piperidine-1-carbonyl]-1-[(1-methyl-1H-imidazol-2-yl)methyl]pyridin-2(1H)-one (compound 18); ESIMS m/z: 534 (M+H)$^+$ 4-{4-(2-chloro-5-methylphenylamino)-5-[4-(4-fluorophenyl)piperidine-1-carbonyl]-2-oxopyridin-1(2H)-yl}butanenitrile (compound 19); ESIMS m/z: 507 (M+H)$^+$ 1-(2-{4-(2-chloro-5-methylphenylamino)-5-[4-(4-fluorophenyl)piperidine-1-carbonyl]-2-oxopyridin-1(2H)-yl}acetyl)pyrrolidine-2-carbonitrile (compound 20); ESIMS m/z: 576 (M+H)$^+$ 4-(2-chloro-5-methylphenylamino)-5-[4-(4-fluorophenyl)piperidine-1-carbonyl]-1-[(tetrahydro-2H-pyran-4-yl)methyl]pyridin-2(1H)-one (compound 22); ESIMS m/z: 538 (M+H)$^+$ 2-{4-(4-fluoro-2-methylphenylamino)-5-[4-(4-fluorophenyl)piperidine-1-carbonyl]-2-oxopyridin-1(2H)-yl}acetonitrile (compound 23); ESIMS m/z: 463 (M+H)$^+$ 3-({4-(4-fluoro-2-methylphenylamino)-5-[4-(4-fluorophenyl)piperidine-1-carbonyl]-2-oxopyridin-1(2H)-yl}methyl)-1,2,4-oxadiazol-5(4H)-one (compound 24); ESIMS m/z: 522 (M+H)$^+$ methyl 2-{4-(4-fluoro-2-methylphenylamino)-5-[4-(4-fluorophenyl)piperidine-1-carbonyl]-2-oxopyridin-1(2H)-yl}acetate (compound 25); ESIMS m/z: 496 (M+H)$^+$ 2-{4-(4-fluoro-2-methylphenylamino)-5-[4-(4-fluorophenyl)piperidine-1-carbonyl]-2-oxopyridin-1(2H)-yl}acetic acid (compound 26); ESIMS m/z: 482 (M+H)$^+$ 4-(4-fluoro-2-methylphenylamino)-5-[4-(4-fluorophenyl)piperidine-1-carbonyl]-1-[(1-methyl-1H-imidazol-2-yl)methyl]pyridin-2(1H)-one (compound 27); ESIMS m/z: 518 (M+H)$^+$ 4-{4-(4-fluoro-2-methylphenylamino)-5-[4-(4-fluorophenyl)piperidine-1-carbonyl]-2-oxopyridin-1(2H)-yl}butanenitrile (compound 28); ESIMS m/z: 491 (M+H)$^+$ methyl 2-{4-(2-chloro-5-methylphenylamino)-5-[4-(4-fluorophenyl)piperidine-1-carbonyl]-2-oxopyridin-1 (2H)-yl}acetate (compound 29); ESIMS m/z: 512 (M+H)$^+$ 2-{4-(benzylamino)-5-[4-(4-fluorophenyl)piperidine-1-carbonyl]-2-oxopyridin-1(2H)-yl}acetonitrile (compound 31); ESIMS m/z: 445 (M+H)$^+$ tert-butyl 2-{4-(benzylamino)-5-[4-(4-fluorophenyl)piperidine-1-carbonyl]-2-oxopyridin-1(2H)-yl}acetate (compound 32); ESIMS m/z: 520 (M+H)$^+$ 3-({4-(benzylamino)-5-[4-(4-fluorophenyl)piperidine-1-carbonyl]-2-oxopyridin-1(2H)-yl}methyl)-1,2,4-oxadiazole-5 (4H)-one (compound 33); ESIMS m/z: 504 (M+H)$^+$ 2-{4-(benzylamino)-5-[4-(4-fluorophenyl)piperidine-1-carbonyl]-2-oxopyridin-1(2H)-yl}acetic acid (compound 34); ESIMS m/z: 464 (M+H)$^+$ 2-{4-(benzylamino)-5-[4-(4-fluorophenyl)piperidine-1-carbonyl]-2-oxopyridin-1(2H)-yl}-N-cyanoacetamide (compound 35); ESIMS m/z: 488 (M+H)$^+$ Example 57

The following compounds were synthesized based on Example 4.

3-chloro-4-(5-chloro-2-methylphenylamino)-5-[4-(4-fluorophenyl)piperidine-1-carbonyl]-1-(pyridin-3-ylmethoxy)pyridin-2(1H)-one (compound 198); ESIMS m/z: 581 (M+H)$^+$ 3-chloro-4-(5-chloro-2-methylphenylamino)-5-[4-(4-fluorophenyl)piperidine-1-carbonyl]-1-[(5-methylisoxazol-3-yl)methoxy]pyridin-2(1H)-one (compound 205); ESIMS m/z: 585 (M+H)$^+$ 3-chloro-4-(5-chloro-2-methylphenylamino)-1-(cyclopropylmethoxy)-5-[4-(4-fluorophenyl)piperidine-1-carbonyl]pyridin-2(1H)-one (compound 213); ESIMS m/z: 544 (M+H)$^+$ 3-chloro-4-(5-chloro-2-methylphenylamino)-5-[4-(4-fluorophenyl)piperidine-1-carbonyl]-1-(2-hydroxypropoxy)pyridin-2(1H)-one (compound 223); ESIMS m/z: 548 (M+H)$^+$ 3-chloro-4-(5-chloro-2-methylphenylamino)-5-[4-(4-fluorophenyl)piperidine-1-carbonyl]-1-[(tetrahydrofuran-2-yl)methoxy]pyridin-2(1H)-one (compound 226); ESIMS m/z: 574 (M+H)$^+$ 3-chloro-4-(5-chloro-2-methylphenylamino)-5-[3-(4-fluorophenyl)azetidine-1-carbonyl]-1-(2-hydroxyethoxy)pyridin-2(1H)-one (compound 233); ESIMS m/z: 506 (M+H)$^+$ 4-[5-chloro-4-(5-chloro-2-methylphenylamino)-1-(2-hydroxyethoxy)-6-oxo-1,6-dihydropyridine-3-carbonyl]-1-(4-fluorophenyl)piperazin-2-one (compound 234); ESIMS m/z: 549 (M+H)$^+$ 3-chloro-4-(5-chloro-2-methylphenylamino)-5-[4-(4-fluorophenyl)-4-methoxypiperidine-1-carbonyl]-1-(2-hydroxyethoxy)pyridin-2(1H)-one (compound 235); ESIMS m/z: 564 (M+H)$^+$ Example 58

The following compounds were synthesized based on Example 12.

4-(4-fluoro-2-methylphenylamino)-5-[4-(4-fluorophenyl)piperidine-1-carbonyl]-1-methylpyridin-2(1H)-one (compound 36); ESIMS m/z: 438 (M+H)$^+$ 4-(4-chloro-2-methylphenylamino)-5-[4-(4-fluorophenyl)piperidine-1-carbonyl]-1-methylpyridin-2(1H)-one (compound 37); ESIMS m/z: 454 (M+H)$^+$ 1-(cyclopropylmethyl)-3-fluoro-4-(4-fluoro-2-methylphenylamino)-5-[4-(4-fluorophenyl)piperidine-1-carbonyl]pyridin-2(1H)-one (compound 38); ESIMS m/z: 496 (M+H)$^+$ 3-chloro-4-(2-chloro-4-fluoro-5-methylphenylamino)-5-[4-(4-fluorophenyl)piperidine-1-carbonyl]-1-methylpyridin-2(1H)-one (compound 41); ESIMS m/z: 506 (M+H)$^+$ 3-chloro-5-[4-(4-fluorophenyl)piperidine-1-carbonyl]-4-(4-methoxyphenylamino)-1-methylpyridin-2(1H)-one (compound 44); ESIMS m/z: 470 (M+H)$^+$ 3-chloro-5-[4-(4-fluorophenyl)piperidine-1-carbonyl]-1-methyl-4-(pyridin-4-ylamino)pyridin-2(1H)-one (compound 45); ESIMS m/z: 441 (M+H)$^+$ 3-chloro-5-[4-(4-fluorophenyl)piperidine-1-carbonyl]-4-(3-methoxyphenylamino)-1-methylpyridin-2(1H)-one (compound 46); ESIMS m/z: 470 (M+H)$^+$ 3-chloro-5-[4-(4-fluorophenyl)piperidine-1-carbonyl]-4-(2-methoxyphenylamino)-1-methylpyridin-2(1H)-one (compound 47); ESIMS m/z: 470 (M+H)$^+$ 3-chloro-4-(cyclopropylamino)-5-[4-(4-fluorophenyl)piperidine-1-carbonyl]-1-methylpyridin-2(1H)-one (compound 48); ESIMS m/z: 404 (M+H)$^+$ 3-chloro-5-[4-(4-fluorophenyl)piperidine-1-carbonyl]-1-methyl-4-[4-(trifluoromethoxy)phenylamino]pyridin-2(1H)-one (compound 49); ESIMS m/z: 524 (M+H)$^+$ 3-chloro-4-(2,5-dimethoxyphenylamino)-5-[4-(4-fluorophenyl)piperidine-1-carbonyl]-1-methylpyridin-2(1H)-one (compound 51); ESIMS m/z: 500 (M+H)$^+$ 3-chloro-5-[4-(4-fluorophenyl)piperidine-1-carbonyl]-1-methyl-4-(pyridin-3-ylamino)pyridin-2(1H)-one (compound 52); ESIMS m/z: 441 (M+H)$^+$ 3-chloro-4-(4-chloro-2-methylphenylamino)-1-cyclopropyl-5-[4-(4-fluorophenyl)piperidine-1-carbonyl]pyridin-2(1H)-one (compound 53); ESIMS m/z: 514 (M+H)$^+$ 3-chloro-4-(2,4-difluorophenylamino)-5-[4-(4-fluorophenyl)piperidine-1-carbonyl]-1-methylpyridin-2(1H)-one (compound 54); ESIMS m/z: 476 (M+H)$^+$ 3-chloro-1-cyclopropyl-5-[4-(4-fluorophenyl)piperidine-1-carbonyl]-4-(4-methoxyphenylamino)pyridin-2(1H)-one (compound 55); ESIMS m/z: 496 (M+H)$^+$ 3-chloro-5-[4-(4-fluorophenyl)piperidine-1-carbonyl]-1-methyl-4-[2-(trifluoromethoxy)phenylamino]pyridin-2(1H)-one (compound 56); ESIMS m/z: 524 (M+H)$^+$ 3-chloro-4-(5-chloro-2-methoxyphenylamino)-5-[4-(4-fluorophenyl)piperidine-1-carbonyl]-1-methylpyridin-2(1H)-one (compound 57); ESIMS m/z: 504 (M+H)$^+$ 3-chloro-4-(2-chloro-5-methylphenylamino)-1-cyclopropyl-5-[4-(4-fluorophenyl)piperidine-1-carbonyl]pyridin-2(1H)-one (compound 58); ESIMS m/z: 514 (M+H)$^+$ 3-chloro-5-[4-(4-fluorophenyl)piperidine-1-carbonyl]-1-methyl-4-(2,4,5-trifluorophenylamino)pyridin-2(1H)-one (compound 59); ESIMS m/z: 494 (M+H)$^+$ 3-chloro-1-cyclopropyl-4-(2,5-dimethoxyphenylamino)-5-[4-(4-fluorophenyl)piperidine-1-carbonyl]pyridin-2(1H)-one (compound 60); ESIMS m/z: 526 (M+H)$^+$ 3-chloro-4-(5-chloro-2,4-dimethoxyphenylamino)-5-[4-(4-fluorophenyl)piperidine-1-carbonyl]-1-methylpyridin-2(1H)-one (compound 61); ESIMS m/z: 534 (M+H)$^+$ 4-{3-chloro-5-[4-(4-fluorophenyl)piperidine-1-carbonyl]-1-methyl-2-oxo-1,2-dihydropyridin-4-ylamino}benzonitrile (compound 62); ESIMS m/z: 465 (M+H)$^+$ 3-chloro-4-(2,4-dimethoxyphenylamino)-5-[4-(4-fluorophenyl)piperidine-1-carbonyl]-1-methylpyridin-2(1H)-one (compound 63); ESIMS m/z: 500 (M+H)$^+$ 3-chloro-4-{3-chloro-5-[4-(4-fluorophenyl)piperidine-1-carbonyl]-1-methyl-2-oxo-1,2-dihydropyridin-4-ylamino}benzonitrile (compound 64); ESIMS m/z: 499 (M+H)$^+$ 3-chloro-4-(4-chlorobenzylamino)-5-[4-(4-fluorophenyl)piperidine-1-carbonyl]-1-methylpyridin-2(1H)-one (compound 65); ESIMS m/z: 488 (M+H)$^+$ 4-{3-chloro-5-[4-(4-fluorophenyl)piperidine-1-carbonyl]-1-methyl-2-oxo-1,2-dihydropyridin-4-ylamino}-3-fluorobenzonitrile (compound 66); ESIMS m/z: 483 (M+H)$^+$ 2-chloro-4-{3-chloro-5-[4-(4-fluorophenyl)piperidine-1-carbonyl]-1-methyl-2-oxo-1,2-dihydropyridin-4-ylamino}benzonitrile (compound 67); ESIMS m/z: 499 (M+H)$^+$ 3-chloro-4-(3,4-dimethoxyphenylamino)-5-[4-(4-fluorophenyl)piperidine-1-carbonyl]-1-methylpyridin-2(1H)-one (compound 68); ESIMS m/z: 500 (M+H)$^+$ 3-chloro-4-(2-fluoro-4-methoxyphenylamino)-5-[4-(4-fluorophenyl)piperidine-1-carbonyl]-1-methylpyridin-2(1H)-one (compound 69); ESIMS m/z: 488 (M+H)$^+$ 3-chloro-1-cyclopropyl-5-[4-(4-fluorophenyl)piperidine-1-carbonyl]-4-(2,4,5-trifluorophenylamino)pyridin-2(1H)-one (compound 70); ESIMS m/z: 520 (M+H)$^+$ 3-chloro-1-cyclopropyl-4-(2,4-difluorophenylamino)-5-[4-(4-fluorophenyl)piperidine-1-carbonyl]pyridin-2(1H)-one (compound 71); ESIMS m/z: 502 (M+H)$^+$ 3-chloro-4-(5-chloro-2-methylphenylamino)-1-cyclopropyl-5-[4-(4-fluorophenyl)piperidine-1-carbonyl]pyridin-2(1H)-one (compound 72); ESIMS m/z: 514 (M+H)$^+$ 3-chloro-1-cyclopropyl-5-[4-(4-fluorophenyl)piperidine-1-carbonyl]-4-(4-methoxy-2-methylphenylamino)pyridin-2(1H)-one (compound 73); ESIMS m/z: 510 (M+H)$^+$ 3-chloro-4-(4-fluoro-3-methylphenylamino)-5-[4-(4-fluorophenyl)piperidine-1-carbonyl]-1-methylpyridin-2(1H)-one (compound 75); ESIMS m/z: 472 (M+H)$^+$ 3-chloro-4-(2,5-dimethylphenylamino)-5-[4-(4-fluorophenyl)piperidine-1-carbonyl]-1-methylpyridin-2(1H)-one (compound 76); ESIMS m/z: 468 (M+H)$^+$ 3-chloro-4-[4-(difluoromethoxy)phenylamino]-5-[4-(4-fluorophenyl)piperidine-1-carbonyl]-1-methylpyridin-2(1H)-one (compound 77); ESIMS m/z: 506 (M+H)$^+$ 3-chloro-5-[4-(4-fluorophenyl)piperidine-1-carbonyl]-4-(4-isopropoxyphenylamino)-1-methylpyridin-2(1H)-one (compound 78); ESIMS m/z: 498 (M+H)$^+$ 3-chloro-4-(4-ethoxyphenylamino)-5-[4-(4-fluorophenyl)piperidine-1-carbonyl]-1-methylpyridin-2(1H)-one (compound 79); ESIMS m/z: 484 (M+H)$^+$ 3-chloro-4-(2,4-dimethylphenylamino)-5-[4-(4-fluorophenyl)piperidine-1-carbonyl]-1-methylpyridin-2(1H)-one (compound 80); ESIMS m/z: 468 (M+H)$^+$ 3-chloro-4-(2,5-difluorophenylamino)-5-[4-(4-fluorophenyl)piperidine-1-carbonyl]-1-methylpyridin-2(1H)-one (compound 82); ESIMS m/z: 476 (M+H)$^+$ 3-chloro-5-[4-(4-fluorophenyl)piperidine-1-carbonyl]-4-(5-methoxy-2-methylphenylamino)-1-methylpyridin-2(1H)-one (compound 83); ESIMS m/z: 484 (M+H)$^+$ 3-chloro-4-(4-chloro-3-methoxyphenylamino)-1-(cyclopropylmethyl)-5-[4-(4-fluorophenyl)piperidine-1-carbonyl]pyridin-2(1H)-one (compound 84); ESIMS m/z: 544 (M+H)$^+$ 3-chloro-1-(cyclopropylmethyl)-4-(4-fluoro-2-methylphenylamino)-5-[4-(4-fluorophenyl)piperidine-1-carbonyl]pyridin-2(1H)-one (compound 85); ESIMS m/z: 512 (M+H)$^+$ 3-chloro-4-(3,4-difluorophenylamino)-5-[4-(4-fluorophenyl)piperidine-1-carbonyl]-1-methylpyridin-2(1H)-one (compound 86); ESIMS m/z: 476 (M+H)$^+$ 3-chloro-4-(3,4-dimethylphenylamino)-5-[4-(4-fluorophenyl)piperidine-1-carbonyl]-1-methylpyridin-2(1H)-one (compound 87); ESIMS m/z: 468 (M+H)$^+$ 3-chloro-4-(4-chloro-3-methoxyphenylamino)-5-[4-(4-fluorophenyl)piperidine-1-carbonyl]-1-methylpyridin-2(1H)-one (compound 88); ESIMS m/z: 504 (M+H)$^+$ 3-chloro-4-(4-fluoro-3-methoxyphenylamino)-5-[4-(4-fluorophenyl)piperidine-1-carbonyl]-1-methylpyridin-2(1H)-one (compound 89); ESIMS m/z: 488 (M+H)$^+$ 3-chloro-4-(2,3-difluorophenylamino)-5-[4-(4-fluorophenyl)piperidine-1-carbonyl]-1-methylpyridin-2(1H)-one (compound 90); ESIMS m/z: 476 (M+H)$^+$ 3-chloro-5-[4-(4-fluorophenyl)piperidine-1-carbonyl]-1-methyl-4-[4-(methylthio)phenylamino]pyridin-2(1H)-one (compound 91); ESIMS m/z: 486 (M+H)$^+$ 3-chloro-4-(3-fluoro-4-methoxyphenylamino)-5-[4-(4-fluorophenyl)piperidine-1-carbonyl]-1-methylpyridin-2(1H)-one (compound 92); ESIMS m/z: 488 (M+H)$^+$ 3-chloro-5-[4-(4-fluorophenyl)piperidine-1-carbonyl]-4-(4-methoxy-3-methylphenylamino)-1-methylpyridin-2(1H)-one (compound 93); ESIMS m/z: 484 (M+H)$^+$ 3-bromo-1-cyclopropyl-4-(4-fluoro-2-methylphenylamino)-5-[4-(4-fluorophenyl)piperidine-1-carbonyl]pyridin-2(1H)-one (compound 94); ESIMS m/z: 542 (M+H)$^+$ 3-{3-chloro-5-[4-(4-fluorophenyl)piperidine-1-carbonyl]-1-methyl-2-oxo-1,2-dihydropyridin-4-ylamino}benzonitrile (compound 95); ESIMS m/z: 465 (M+H)$^+$ 4-{3-chloro-5-[4-(4-fluorophenyl)piperidine-1-carbonyl]-1-methyl-2-oxo-1,2-dihydropyridin-4-ylamino}phthalonitrile (compound 96); ESIMS m/z: 490 (M+H)$^+$ 4-{3-chloro-5-[4-(4-fluorophenyl)piperidine-1-carbonyl]-1-methyl-2-oxo-1,2-dihydropyridin-4-ylamino}-2,5-difluorobenzonitrile (compound 97); ESIMS m/z: 501 (M+H)$^+$ 5-{3-chloro-5-[4-(4-fluorophenyl)piperidine-1-carbonyl]-1-methyl-2-oxo-1,2-dihydropyridin-4-ylamino}-2-methylbenzonitrile (compound 98); ESIMS m/z: 479 (M+H)$^+$ 2-{3-chloro-5-[4-(4-fluorophenyl)piperidine-1-carbonyl]-1-methyl-2-oxo-1,2-dihydropyridin-4-ylamino}benzonitrile (compound 99); ESIMS m/z: 465 (M+H)$^+$ 4-{3-chloro-5-[4-(4-fluorophenyl)piperidine-1-carbonyl]-1-methyl-2-oxo-1,2-dihydropyridin-4-ylamino}-3-ethylbenzonitrile (compound 101); ESIMS m/z: 493 (M+H)$^+$ 3-chloro-4-(2-fluoro-4-methylphenylamino)-5-[4-(4-fluorophenyl)piperidine-1-carbonyl]-1-methylpyridin-2(1H)-one (compound 102); ESIMS m/z: 472 (M+H)$^+$ 2-{3-chloro-5-[4-(4-fluorophenyl)piperidine-1-carbonyl]-1-methyl-2-oxo-1,2-dihydropyridin-4-ylamino}-4-methylbenzonitrile (compound 104); ESIMS m/z: 479 (M+H)$^+$ 3-chloro-4-(2,3-dimethylphenylamino)-5-[4-(4-fluorophenyl)piperidine-1-carbonyl]-1-methylpyridin-2(1H)-one (compound 105); ESIMS m/z: 468 (M+H)$^+$ 3-chloro-4-(2,2-difluorobenzo[d][1,3]dioxol-5-ylamino)-5-[4-(4-fluorophenyl)piperidine-1-carbonyl]-1-methylpyridin-2(1H)-one (compound 106); ESIMS m/z: 520 (M+H)$^+$ 3-chloro-4-(2,3-dihydro-1H-inden-5-ylamino)-5-[4-(4-fluorophenyl)piperidine-1-carbonyl]-1-methylpyridin-2(1H)-one (compound 107); ESIMS m/z: 480 (M+H)$^+$ 3-chloro-4-(4-ethylphenylamino)-5-[4-(4-fluorophenyl)piperidine-1-carbonyl]-1-methylpyridin-2(1H)-one (compound 108); ESIMS m/z: 468 (M+H)$^+$ 4-{3-chloro-5-[4-(4-fluorophenyl)piperidine-1-carbonyl]-1-methyl-2-oxo-1,2-dihydropyridin-4-ylamino}-2-fluorobenzonitrile (compound 109); ESIMS m/z: 483 (M+H)$^+$ 4-{3-chloro-5-[4-(4-fluorophenyl)piperidine-1-carbonyl]-1-methyl-2-oxo-1,2-dihydropyridin-4-ylamino}-2,6-difluorobenzonitrile (compound 110); ESIMS m/z: 501 (M+H)$^+$ 4-{3-chloro-5-[4-(4-fluorophenyl)piperidine-1-carbonyl]-1-methyl-2-oxo-1,2-dihydropyridin-4-ylamino}-2-(trifluoromethyl)benzonitrile (compound 112); ESIMS m/z: 533 (M+H)$^+$ 3-chloro-5-[4-(4-fluorophenyl)piperidine-1-carbonyl]-1-methyl-4-[4-(methylthio)-3-(trifluoromethyl)phenylamino]pyridin-2(1H)-one (compound 113); ESIMS m/z: 554 (M+H)$^+$ 3-chloro-5-[4-(4-fluorophenyl)piperidine-1-carbonyl]-1-methyl-4-[4-(trifluoromethyl)phenylamino]pyridin-2(1H)-one (compound 114); ESIMS m/z: 508 (M+H)$^+$ 3-chloro-5-[4-(4-fluorophenyl)piperidine-1-carbonyl]-4-(4-isopropylphenylamino)-1-methylpyridin-2(1H)-one (compound 115); ESIMS m/z: 482 (M+H)$^+$ 5-chloro-2-{3-chloro-5-[4-(4-fluorophenyl)piperidine-1-carbonyl]-1-methyl-2-oxo-1,2-dihydropyridin-4-ylamino}benzonitrile (compound 116); ESIMS m/z: 499 (M+H)$^+$ 4-chloro-3-{3-chloro-5-[4-(4-fluorophenyl)piperidine-1-carbonyl]-1-methyl-2-oxo-1,2-dihydropyridin-4-ylamino}benzonitrile (compound 117); ESIMS m/z: 499 (M+H)$^+$ 3-chloro-4-(2-fluoro-5-methylphenylamino)-5-[4-(4-fluorophenyl)piperidine-1-carbonyl]-1-methylpyridin-2(1H)-one (compound 118); ESIMS m/z: 472 (M+H)$^+$ 3-chloro-4-(5-chloro-2-fluorophenylamino)-5-[4-(4-fluorophenyl)piperidine-1-carbonyl]-1-methylpyridin-2(1H)-one (compound 119); ESIMS m/z: 492 (M+H)$^+$ 3-chloro-5-[4-(4-fluorophenyl)piperidine-1-carbonyl]-1-methyl-4-[4-(methylsulfonyl)-3-(trifluoromethyl)phenylamino]pyridin-2(1H)-one (compound 122); ESIMS m/z: 586 (M+H)$^+$ 3-chloro-4-[3-chloro-4-(methylsulfonyl)phenylamino]-5-[4-(4-fluorophenyl)piperidine-1-carbonyl]-1-methylpyridin-2(1H)-one (compound 123); ESIMS m/z: 552 (M+H)$^+$ 3-chloro-4-(5-fluoro-2-methylphenylamino)-5-[4-(4-fluorophenyl)piperidine-1-carbonyl]-1-methylpyridin-2(1H)-one (compound 126); ESIMS m/z: 472 (M+H)$^+$ 3-chloro-4-(2-chloro-5-fluorophenylamino)-5-[4-(4-fluorophenyl)piperidine-1-carbonyl]-1methylpyridin-2(1H)-one (compound 127); ESIMS m/z: 492 (M+H)$^+$ 3-chloro-4-[2-fluoro-4-(methylthio)phenylamino]-5-[4-(4-fluorophenyl)piperidine-1-carbonyl]-1methylpyridin-2(1H)-one (compound 128); ESIMS m/z: 504 (M+H)$^+$ 3-{3-chloro-5-[4-(4-fluorophenyl)piperidine-1-carbonyl]-1-methyl-2-oxo-1,2-dihydropyridin-4-ylamino}-4-methylbenzonitrile (compound 129); ESIMS m/z: 479 (M+H)$^+$ 2-{3-chloro-5-[4-(4-fluorophenyl)piperidine-1-carbonyl]-1-methyl-2-oxo-1,2-dihydropyridin-4-ylamino}-4-fluorobenzonitrile (compound 131); ESIMS m/z: 483 (M+H)$^+$ 2-{3-chloro-5-[4-(4-fluorophenyl)piperidine-1-carbonyl]-1-methyl-2-oxo-1,2-dihydropyridin-4-ylamino}-5-methylbenzonitrile (compound 132); ESIMS m/z: 479 (M+H)$^+$ 5-{3-chloro-5-[4-(4-fluorophenyl)piperidine-1-carbonyl]-1-methyl-2-oxo-1,2-dihydropyridin-4-ylamino}-2-(methylthio)benzonitrile (compound 133); ESIMS m/z: 511 (M+H)$^+$ 3-{3-chloro-5-[4-(4-fluorophenyl)piperidine-1-carbonyl]-1-methyl-2-oxo-1,2-dihydropyridin-4-ylamino}-4-(difluoromethoxy)benzonitrile (compound 134); ESIMS m/z: 531 (M+H)$^+$ 3-chloro-1-ethyl-4-(4-fluoro-2-methylphenylamino)-5-[4-(4-fluorophenyl)piperidine-1-carbonyl]pyridin-2(1H)-one (compound 135); ESIMS m/z: 486 (M+H)$^+$ 3-chloro-4-(4-chloro-2-methylphenylamino)-1-ethyl-5-[4-(4-fluorophenyl)piperidine-1-carbonyl]pyridin-2(1H)-one (compound 136); ESIMS m/z: 502 (M+H)$^+$ 3-chloro-4-(5-chloro-2-methylphenylamino)-1-ethyl-5-[4-(4-fluorophenyl)piperidine-1-carbonyl]pyridin-2(1H)-one (compound 137); ESIMS m/z: 502 (M+H)$^+$ 3-chloro-1-ethyl-5-[4-(4-fluorophenyl)piperidine-1-carbonyl]-4-(4-methoxy-2-methylphenylamino)pyridin-2(1H)- one (compound 138); ESIMS m/z: 498 (M+H)⁺3-chloro-4-(2,4-difluorophenylamino)-1-ethyl-5-[4-(4-fluorophenyl)piperidine-1-carbonyl]pyridin-2(1H)-one (compound 139); ESIMS m/z: 490 (M+H)⁺

3-chloro-4-(4-fluoro-2-methylphenylamino)-5-[4-(4-fluorophenyl)piperidine-1-carbonyl]-1-(2-methoxyethyl)pyridin-2(1H)-one (compound 140); ESIMS m/z: 516 (M+H)⁺

3-chloro-4-(4-chloro-2-methylphenylamino)-5-[4-(4-fluorophenyl)piperidine-1-carbonyl]-1-(2-methoxyethyl)pyridin-2(1H)-one (compound 141); ESIMS m/z: 532 (M+H)⁺

3-chloro-4-(5-chloro-2-methylphenylamino)-5-[4-(4-fluorophenyl)piperidine-1-carbonyl]-1-(2-methoxyethyl)pyridin-2(1H)-one (compound 142); ESIMS m/z: 532 (M+H)⁺

3-chloro-5-[4-(4-fluorophenyl)piperidine-1-carbonyl]-4-(4-methoxy-2-methylphenylamino)-1-(2-methoxyethyl)pyridin-2(1H)-one (compound 143); ESIMS m/z: 528 (M+H)⁺

3-chloro-4-[2-fluoro-4-(methylsulfonyl)phenylamino]-5-[4-(4-fluorophenyl)piperidine-1-carbonyl]-1-methylpyridin-2(1H)-one (compound 145); ESIMS m/z: 536 (M+H)⁺

5-{3-chloro-5-[4-(4-fluorophenyl)piperidine-1-carbonyl]-1-methyl-2-oxo-1,2-dihydropyridin-4-ylamino}-2-(methylsulfonyl)benzonitrile (compound 146); ESIMS m/z: 543 (M+H)⁺

2-chloro-5-{3-chloro-5-[4-(4-fluorophenyl)piperidine-1-carbonyl]-1-methyl-2-oxo-1,2-dihydropyridin-4-ylamino}benzonitrile (compound 147); ESIMS m/z: 499 (M+H)⁺

3-{3-chloro-5-[4-(4-fluorophenyl)piperidine-1-carbonyl]-1-methyl-2-oxo-1,2-dihydropyridin-4-ylamino}-4-fluorobenzonitrile (compound 148); ESIMS m/z: 483 (M+H)⁺

2-{3-chloro-5-[4-(4-fluorophenyl)piperidine-1-carbonyl]-1-methyl-2-oxo-1,2-dihydropyridin-4-ylamino}-4-(trifluoromethyl)benzonitrile (compound 149); ESIMS m/z: 533 (M+H)⁺

2-{3-chloro-5-[4-(4-fluorophenyl)piperidine-1-carbonyl]-1-methyl-2-oxo-1,2-dihydropyridin-4-ylamino}-5-fluorobenzonitrile (compound 150); ESIMS m/z: 483 (M+H)⁺

3-chloro-4-(4-fluoro-2-methylphenylamino)-5-[4-(4-fluorophenyl)piperidine-1-carbonyl]-1-(pyridin-3-ylmethyl)pyridin-2(1H)-one (compound 151); ESIMS m/z: 549 (M+H)⁺

3-chloro-4-(4-chloro-2-methylphenylamino)-5-[4-(4-fluorophenyl)piperidine-1-carbonyl]-1-(pyridin-3-ylmethyl)pyridin-2(1H)-one (compound 152); ESIMS m/z: 565 (M+H)⁺

3-chloro-4-(5-chloro-2-methylphenylamino)-5-[4-(4-fluorophenyl)piperidine-1-carbonyl]-1-(pyridin-3-ylmethyl)pyridin-2(1H)-one (compound 153); ESIMS m/z: 565 (M+H)⁺

3-chloro-4-(2,4-difluorophenylamino)-5-[4-(4-fluorophenyl)piperidine-1-carbonyl]-1-(pyridin-3-ylmethyl)pyridin-2(1H)-one (compound 155); ESIMS m/z: 553 (M+H)⁺

2-{3-chloro-5-[4-(4-fluorophenyl)piperidine-1-carbonyl]-1-methyl-2-oxo-1,2-dihydropyridin-4-ylamino}-5-(trifluoromethoxy)benzonitrile (compound 156); ESIMS m/z: 549 (M+H)⁺

3-chloro-4-(4-fluoro-2-methylphenylamino)-1-(2-fluoroethyl)-5-[4-(4-fluorophenyl)piperidine-1-carbonyl]pyridin-2(1H)-one (compound 158); ESIMS m/z: 504 (M+H)⁺

3-chloro-4-(4-chloro-2-methylphenylamino)-1-(2-fluoroethyl)-5-[4-(4-fluorophenyl)piperidine-1-carbonyl]pyridin-2(1H)-one (compound 159); ESIMS m/z: 520 (M+H)⁺

3-chloro-1-(2-fluoroethyl)-5-[4-(4-fluorophenyl)piperidine-1-carbonyl]-4-(4-methoxy-2-methylphenylamino)pyridin-2(1H)-one (compound 161); ESIMS m/z: 516 (M+H)⁺

3-chloro-4-(2,4-difluorophenylamino)-1-(2-fluoroethyl)-5-[4-(4-fluorophenyl)piperidine-1-carbonyl]pyridin-2(1H)-one (compound 162); ESIMS m/z: 508 (M+H)⁺

3-chloro-4-(5-chloro-2-methylphenylamino)-5-[4-(4-fluorophenyl)piperidine-1-carbonyl]-1-(pyridin-2-ylmethyl)pyridin-2(1H)-one (compound 163); ESIMS m/z: 565 (M+H)⁺

5-{3-chloro-5-[4-(4-fluorophenyl)piperidine-1-carbonyl]-1-methyl-2-oxo-1,2-dihydropyridin-4-ylamino}-2-fluorobenzonitrile (compound 164); ESIMS m/z: 483 (M+H)⁺

2-{3-chloro-5-[4-(4-fluorophenyl)piperidine-1-carbonyl]-1-methyl-2-oxo-1,2-dihydropyridin-4-ylamino}-5-(trifluoromethyl)benzonitrile (compound 165); ESIMS m/z: 533 (M+H)⁺

5-{3-chloro-5-[4-(4-fluorophenyl)piperidine-1-carbonyl]-1-methyl-2-oxo-1,2-dihydropyridin-4-ylamino}-2-methylisoindoline-1,3-dione (compound 171); ESIMS m/z: 523 (M+H)⁺

3-chloro-4-(2,4-difluorophenylamino)-5-[4-(4-fluorophenyl)piperidine-1-carbonyl]-1-(pyridin-2-ylmethyl)pyridin-2(1H)-one (compound 172); ESIMS m/z: 553 (M+H)⁺

4-(benzo[c][1,2,5]oxadiazol-4-ylamino)-3-chloro-5-[4-(4-fluorophenyl)piperidine-1-carbonyl]-1-methylpyridin-2(1H)-one (compound 174); ESIMS m/z: 482 (M+H)⁺

3-chloro-4-(2,2-dimethyl-2,3-dihydrobenzofuran-7-ylamino)-5-[4-(4-fluorophenyl)piperidine-1-carbonyl]-1-methylpyridin-2(1H)-one (compound 176); ESIMS m/z: 510 (M+H)⁺

3-chloro-4-(3,4-dihydro-2H-benzo[b][1,4]dioxepin-7-ylamino)-5-[4-(4-fluorophenyl)piperidine-1-carbonyl]-1-methylpyridin-2(1H)-one (compound 180); ESIMS m/z: 512 (M+H)⁺

3-chloro-4-(2,3-dihydrobenzo[b][1,4]dioxin-6-ylamino)-5-[4-(4-fluorophenyl)piperidine-1-carbonyl]-1-methylpyridin-2(1H)-one (compound 181); ESIMS m/z: 498 (M+H)⁺

3-chloro-4-(5-chloro-2-methylphenylamino)-1-methyl-5-[3H-spiro(isobenzofuran-1,4'-piperidine)-1'-ylcarbonyl]pyridin-2(1H)-one (compound 201); ESIMS m/z: 498 (M+H)⁺

3-chloro-4-(5-chloro-2-methylphenylamino)-5-[4-(2-chlorophenyl)piperazine-1-carbonyl]-1-methylpyridin-2(1H)-one (compound 202); ESIMS m/z: 505 (M+H)⁺

3-chloro-4-(2,6-dimethylpyridin-3-ylamino)-5-[4-(4-fluorophenyl)piperidine-1-carbonyl]-1-vinylpyridin-2(1H)-one (compound 210); ESIMS m/z: 481 (M+H)⁺

3-chloro-1-cyclopentyl-4-(2,6-dimethylpyridin-3-ylamino)-5-[4-(4-fluorophenyl)piperidine-1-carbonyl]pyridin-2(1H)-one (compound 214); ESIMS m/z: 523 (M+H)⁺

3-chloro-1-cyclopropyl-4-(1,3-dihydroisobenzofuran-5-ylamino)-5-[4-(4-fluorophenyl)piperidine-1-carbonyl]pyridin-2(1H)-one (compound 215); ESIMS m/z: 508 (M+H)⁺

Example 59

The following compounds were synthesized based on Example 15.

4-(4-fluoro-2-methylphenylamino)-5-[4-(4-fluorophenyl)piperidine-1-carbonyl]-1,3-dimethylpyridin-2(1H)-one (compound 120); ESIMS m/z: 452 (M+H)⁺

4-(5-chloro-2-methylphenylamino)-5-[4-(4-fluorophenyl)piperidine-1-carbonyl]-1,3-dimethylpyridin-2(1H)-one (compound 121); ESIMS m/z: 468 (M+H)$^+$ 4-{5-[4-(4-fluorophenyl)piperidine-1-carbonyl]-1,3-dimethyl-2-oxo-1,2-dihydropyridin-4-ylamino}-3-methylbenzonitrile (compound 124); ESIMS m/z: 459 (M+H)$^+$ 4-(4-chloro-2-fluorophenylamino)-5-[4-(4-fluorophenyl)piperidine-1-carbonyl]-1,3-dimethylpyridin-2(1H)-one (compound 193); ESIMS m/z: 472 (M+H)$^+$ 4-(1,3-dihydroisobenzofuran-5-ylamino)-5-[4-(4-fluorophenyl)piperidine-1-carbonyl]-3-methyl-1-(pyridin-3-ylmethyl)pyridin-2(1H)-one (compound 207); ESIMS m/z: 539 (M+H)$^+$ 1-cyclobutyl-4-(1,3-dihydroisobenzofuran-5-ylamino)-5-[4-(4-fluorophenyl)piperidine-1-carbonyl]-3-methylpyridin-2(1H)-one (compound 211); ESIMS m/z: 502 (M+H)$^+$ 1-cyclopentyl-5-[4-(4-fluorophenyl)piperidine-1-carbonyl]-3-methyl-4-(1-methyl-1H-indazol-5-ylamino)pyridin-2(1H)-one (compound 212); ESIMS m/z: 528 (M+H)$^+$ Example 60

The following compounds were synthesized based on Example 21.

3-chloro-4-(5-chloro-2-methylphenylamino)-5-[4-(4-fluorophenyl)piperidine-1-carbonyl]-1-(2-propynyl)pyridin-2(1H)-one (compound 167); ESIMS m/z: 512 (M+H)$^+$ 3-chloro-4-(2,4-difluorophenylamino)-5-[4-(4-fluorophenyl)piperidine-1-carbonyl]-1-(2-morpholinoethyl)pyridin-2(1H)-one (compound 182); ESIMS m/z: 575 (M+H)$^+$ 3-chloro-4-(5-chloro-2-methylphenylamino)-5-[4-(4-fluorophenyl)piperidine-1-carbonyl]-1-(2-morpholinoethyl)pyridin-2(1H)-one (compound 185); ESIMS m/z: 587 (M+H)$^+$ Example 61

The following compounds were synthesized based on Example 39.

4-(benzylamino)-5-[4-(4-fluorophenyl)piperidine-1-carbonyl]-1-methyl-3-nitropyridin-2(1H)-one (compound 216); ESIMS m/z: 465 (M+H)$^+$ 5-[4-(4-fluorophenyl)piperidine-1-carbonyl]-1-methyl-3-nitro-4-(o-tolylamino)pyridin-2(1H)-one (compound 222); ESIMS m/z: 465 (M+H)$^+$ Example 62

The following compounds were synthesized based on Example 41.

3-amino-4-(benzylamino)-5-[4-(4-fluorophenyl)piperidine-1-carbonyl]-1-methylpyridin-2(1H)-one (compound 218); ESIMS m/z: 435 (M+H)$^+$ 3-amino-5-[4-(4-fluorophenyl)piperidine-1-carbonyl]-1-methyl-4-(phenylamino)pyridin-2(1H)-one (compound 219); ESIMS m/z: 421 (M+H)$^+$ Example 63

The following compounds were synthesized based on Example 50.

3-chloro-5-[4-(4-fluorophenyl)piperidine-1-carbonyl]-1-(2-hydroxyethoxy)-4-(1-phenylcyclopropylamino)pyridin-2(1H)-one (compound 231); ESIMS m/z: 526 (M+H)$^+$ 3-chloro-5-[4-(4-fluorophenyl)piperidine-1-carbonyl]-1-(2-hydroxyethoxy)-4-(pyridin-3-ylmethylamino)pyridin-2(1H)-one (compound 232); ESIMS m/z: 501 (M+H)$^+$ 3-chloro-5-[4-(4-fluorophenyl)piperidine-1-carbonyl]-1-(2-hydroxyethoxy)-4-[1-(pyridin-2-yl)cyclopropylamino]pyridin-2(1H)-one (compound 236); ESIMS m/z: 527 (M+H)$^+$ Example 64

The following compounds were synthesized based on Example 55.

5-[4-(4-fluorophenyl)piperidine-1-carbonyl]-1-(2-hydroxyethoxy)-3-methyl-4-(6-methylpyridin-3-ylamino)pyridin-2(1H)-one (compound 227); ESIMS m/z: 481 (M+H)$^+$ 4-{5-[4-(4-fluorophenyl)piperidine-1-carbonyl]-3-methyl-2-oxo-1-(pyridin-2-ylmethoxy)-1,2-dihydropyridin-4-ylamino}-3-methylbenzonitrile (compound 230); ESIMS m/z: 552 (M+H)$^+$

INDUSTRIAL APPLICABILITY

The pyridone compound or the pharmaceutically acceptable salt thereof of the present invention is useful as, for example, a prophylactic and/or therapeutic agent for skin diseases and the like.

According to the present invention, a pyridone compound or a pharmaceutically acceptable salt thereof, which is useful as, for example, a prophylactic and/or therapeutic agent for skin diseases and the like are provided.

SEQUENCE LISTING FREE TEXT

SEQ ID NO: 1-explanation of artificial sequence: synthetic DNA
SEQ ID NO: 2-explanation of artificial sequence: synthetic DNA
SEQ ID NO: 3-explanation of artificial sequence: synthetic DNA
SEQ ID NO: 4-explanation of artificial sequence: synthetic DNA

The invention claimed is:

1. A pyridone compound represented by the formula (I)

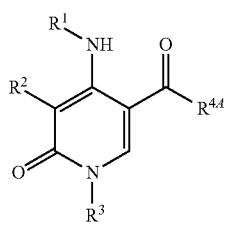

wherein
$R^1$ represents cycloalkyl optionally having substituent(s), aryl optionally having substituent(s), an aromatic heterocyclic group optionally having substituent(s), an aliphatic heterocyclic group optionally having substituent(s), aralkyl optionally having substituent(s), or heterocyclic alkyl optionally having substituent(s), $R^2$ represents a hydrogen atom, cyano, nitro, halogen, lower alkyl optionally having substituent(s), or $NR^{1a}R^{1b}$ (wherein, $R^{1a}$ and $R^{1b}$ are the same or different and each represents a hydrogen atom, lower alkanoyl optionally having substituent(s), or lower alkylcarbamoyl optionally having substituent(s)), $R^3$ represents hydroxy, lower alkyl optionally having substituent(s), lower alkenyl optionally having substituent(s), lower alkynyl optionally having substituent(s), lower alkoxy optionally having substituent(s), cycloalkyl optionally having substituent(s), heterocyclic alkyl optionally having substituent(s), or $-NR^{3a}R^{3b}$ (wherein, $R^{3a}$ and $R^{3b}$ are the same or different and each represents a hydrogen atom, lower alkyl optionally having substituent(s), cycloalkyl optionally having substituent(s), aryl optionally having substituent(s), or aralkyl optionally having substituent(s), or $R^{3a}$ and $R^{3b}$ form, together with the adjacent nitrogen atom, a nitrogen-containing heterocyclic group optionally having substituent(s)), $R^{4A}$ represents any one of the groups represented by the formula ($R^{4A}$-1)

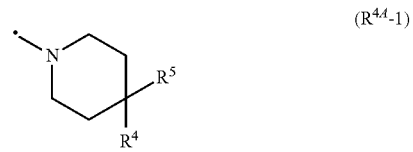

wherein $R^4$ and $R^5$ are the same or different and each represents a hydrogen atom or aryl optionally having substituent(s), or a pharmaceutically acceptable salt thereof.

2. The pyridone compound or the pharmaceutically acceptable salt thereof according to claim 1, wherein $R^1$ is aryl optionally having substituent(s), an aromatic heterocyclic group optionally having substituent(s), or an aliphatic heterocyclic group optionally having substituent(s).

3. The pyridone compound or the pharmaceutically acceptable salt thereof according to claim 1, wherein $R^1$ is aryl optionally having substituent(s).

4. The pyridone compound or the pharmaceutically acceptable salt thereof according to claim 1, wherein $R^1$ is an aromatic heterocyclic group optionally having substituent(s).

5. The pyridone compound or the pharmaceutically acceptable salt thereof according to claim 1, wherein $R^2$ is a hydrogen atom, halogen or lower alkyl optionally having substituent(s).

6. The pyridone compound or the pharmaceutically acceptable salt thereof according to claim 1, wherein $R^2$ is lower alkyl optionally having substituent(s).

7. The pyridone compound or the pharmaceutically acceptable salt thereof according to claim 1, wherein $R^2$ is halogen.

8. The pyridone compound or the pharmaceutically acceptable salt thereof according to claim 1, wherein $R^3$ is lower alkyl optionally having substituent(s), lower alkoxy optionally having substituent(s), or —$NR^{3a}R^{3b}$ (wherein, $R^{3a}$ and $R^{3b}$ are each as defined above).

9. The pyridone compound or the pharmaceutically acceptable salt thereof according to claim 1, wherein $R^3$ is lower alkyl optionally having substituent(s).

10. The pyridone compound or the pharmaceutically acceptable salt thereof according to claim 1, wherein $R^3$ is lower alkoxy optionally having substituent(s).

11. The pyridone compound or the pharmaceutically acceptable salt thereof according to claim 1, wherein $R^3$ is —$NR^{3a}R^{3b}$ (wherein, $R^{3a}$ and $R^{3b}$ are each as defined above).

12. A pharmaceutical composition comprising (a) the pyridone compound or the pharmaceutically acceptable salt thereof of claim 1 and (b) a pharmaceutically acceptable carrier.

13. A method for the treatment of a skin disease, comprising a step of administering an effective amount of the pyridone compound or the pharmaceutically acceptable salt thereof described in claim 1.

14. The method according to claim 13, wherein the skin disease is a skin disease selected from acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

15. The method according to claim 13, wherein the skin disease is a skin disease selected from contact dermatitis and atopic dermatitis.

* * * * *

SEQUENCE LISTING

```
<160> NUMBER OF SEQ ID NOS: 4

<210> SEQ ID NO 1
<211> LENGTH: 61
<212> TYPE: DNA
<213> ORGANISM: Artificial Sequence
<220> FEATURE:
<223> OTHER INFORMATION: synthetic DNA

<400> SEQUENCE: 1
```

```
cagtcaagct tccaccatgg ggacggaggc cacagagcag gtttcctggg gccatttact c    61

<210> SEQ ID NO 2
<211> LENGTH: 37
<212> TYPE: DNA
<213> ORGANISM: Artificial Sequence
<220> FEATURE:
<223> OTHER INFORMATION: synthetic DNA

<400> SEQUENCE: 2
gttatagcgg ccgcagcctg cccctcctc tagattc                              37

<210> SEQ ID NO 3
<211> LENGTH: 25
<212> TYPE: DNA
<213> ORGANISM: Artificial Sequence
<220> FEATURE:
<223> OTHER INFORMATION: synthetic DNA

<400> SEQUENCE: 3
cggagactct agagggtata taatg                                          25

<210> SEQ ID NO 4
<211> LENGTH: 21
<212> TYPE: DNA
<213> ORGANISM: Artificial Sequence
<220> FEATURE:
<223> OTHER INFORMATION: synthetic DNA

<400> SEQUENCE: 4
ctaatacgac tcactatagg g                                              21
```